US012674177B2

(12) United States Patent
Kupatt et al.

(10) Patent No.: US 12,674,177 B2
(45) Date of Patent: Jul. 7, 2026

(54) AAV VECTORS FOR VASCULAR GENE THERAPY IN CORONARY HEART DISEASE AND PERIPHERAL ISCHEMIA

(71) Applicant: Christian Kupatt, Munich (DE)

(72) Inventors: Christian Kupatt, Munich (DE); Rabea Hinkel, Munich (DE)

(73) Assignee: Christian Kupatt, Munich (DE)

( * ) Notice: Subject to any disclaimer, the term of this patent is extended or adjusted under 35 U.S.C. 154(b) by 0 days.

(21) Appl. No.: 17/720,369

(22) Filed: Apr. 14, 2022

(65) Prior Publication Data

US 2024/0167053 A1     May 23, 2024

Related U.S. Application Data

(63) Continuation of application No. 15/303,823, filed as application No. PCT/EP2015/057987 on Apr. 13, 2015, now abandoned.

(30) Foreign Application Priority Data

Apr. 14, 2014    (DE) ........................ 10 201 207 153.4

(51) Int. Cl.
| | |
|---|---|
| *A01N 63/00* | (2020.01) |
| *A61K 38/18* | (2006.01) |
| *A61K 48/00* | (2006.01) |
| *C12N 7/00* | (2006.01) |
| *C12N 15/86* | (2006.01) |

(52) U.S. Cl.
CPC .............. *C12N 15/86* (2013.01); *A61K 38/18* (2013.01); *A61K 48/005* (2013.01); *C12N 7/00* (2013.01); *C12N 2750/14143* (2013.01)

(58) Field of Classification Search
None
See application file for complete search history.

(56) References Cited

PUBLICATIONS

Luchsinger (Thesis, 2011, p. 1-269).*
Kupatt (J Am Clin Cardiol, 2010, vol. 56, p. 414-422).*
Prasad (J. Gene Med., 2011, vol. 13, p. 333-341).*
Forsayeth (Mol. Therapy, 2011, vol. 19, No. 6, p. 1006-1007).*
Andoh et al., J Biochem, 2006, 140:483-9.
Bednarek et al., J. Biol. Chem, 2008, 283:1534-44.
Bell et al., J Clin Invest, 2011, 121:2427-35.
Bish et al., Hum. Gene Ther, 2008, 19:1359-68.
Bito et al., Circ Res, 2007, 100:229-37.
Dor et al., EMBO J., 2002, 21:1939-47.
Franco et al., Development, 2013, 2321-33.
Geneste et al., J Cell Biol, 2002, 157:831-8.
Grant et al., J Cell Sci, 1995, 108:3685-94.
Hall-Glenn et al., PLoS ONE, 2012, 7:e30562.
Hanna et al., J. Biol. Chem., 2009, 284:23125-36.
Heusch, J Mol Cell Cardiol, 1996, 28:2359-72.
Huff et al., Ann. N. Y. Acad. Sci., 2007, 1112:451-7.
Jain, Nat Med, 2003, 9:685-693.
Kupatt et al., J Am Coll Cardiol, 2007, 49:1575-84.
Kupatt et al., J Am Coll Cardiol, 2010, 56:414-22.
Lebherz et al., Endothelium, 2003, 10:257-65.
Leitner et al., J Cell Sci, 2011, 124:4318-31.
Levy et al., N Engl J Med, 2002, 347:1397-402.
Limbourg et al., Nat. Protocols, 2009, 4:1737-48.
Lloyd-Jones et al., Circulation, 2010, 121:e46-e215.
Miralles et al., Cell, 2003, 113:329-42.
Muzumdar et al., Genesis, 2007, 45:593-605.
Nagueh et al., Circulation, 1999, 100:490-6.
Pfosser et al., Cardiovasc. Res., 2005, 65:728-736.
Posern et al., Mol. Biol. Cell, 2002, 13:4167-78.
Potente et al., Cell, 2011, 146:873-887.
Qin et al., PLoS ONE, 2013, 8:e61831.
Renner et al., Diabetes, 2013, 62:1505-1511.
Rissanen et al., Mol Ther 2007, 15:1233-47.
Schierling et al., J Vasc Res, 2009, 46:365-374.
Smart et al., Nature, 2007, 445:177-82.
Smith et al., J Am Coll Cardiol, 2012, 59:1320-8.
St. Louis et al., Ann Thoracic Surg, 2000, 69:1351-7.
Suero et al., J Am Coll. Cardiol, 2001, 38:409-14.
Thein et al., Comput. Methods Programs Biomed., 2000, 61:11-21.
Tirziu et al., Circulation, 2012, 126:2589-600.
Van Royen et al., Circulation, 2005, 112:1040-6.
Vartiainen et al., Science, 2007, 316:1749-52.
Von Degenfeld et al., J. Am. Coll. Cardiol., 2003, 42:1120-8.
Weinl et al., J Clin Invest, 2013, 123:2193-206.
Ziegler et al., J Clin Invest, 2013, 123:3436-45.
Lehrke et al., Cell Metab, 2005, 1:297-308.

* cited by examiner

*Primary Examiner* — Michael C Wilson

(74) *Attorney, Agent, or Firm* — Stacey J. Farmer; Grund IP Group

(57) ABSTRACT

The invention relates to the provision of a gene therapy for coronary heart disease and peripheral ischemia in mammals. One embodiment is an adeno-associated viral vector (AAV vector) comprising a first gene encoding a myocardin-related transcription factor A (MRTF-A). The invention further also relates to a pharmaceutical composition comprising an AAV vector of the invention and a pharmaceutically acceptable carrier. Methods for preparing the vector of the invention are also disclosed.

14 Claims, 43 Drawing Sheets

Specification includes a Sequence Listing.

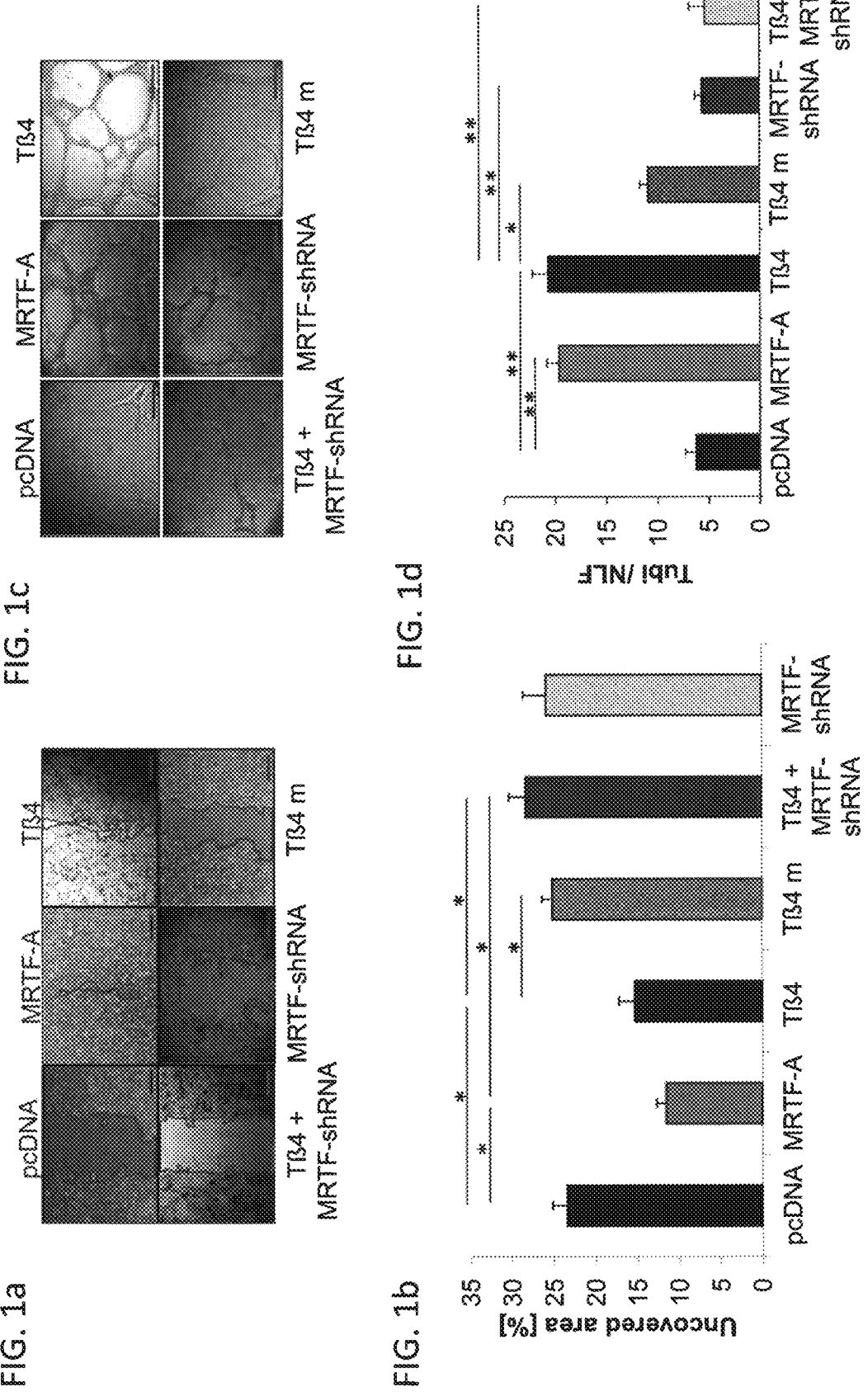

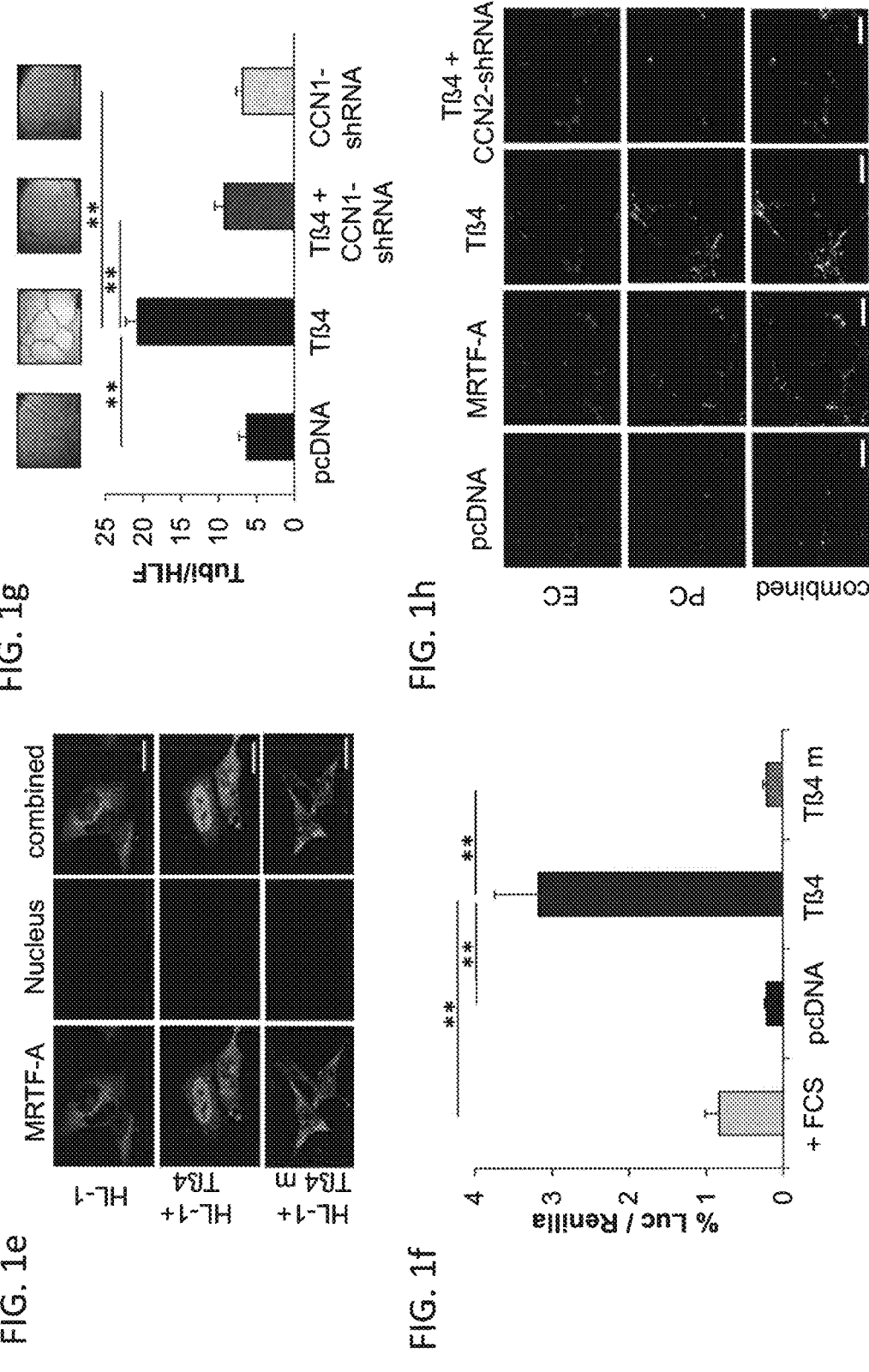

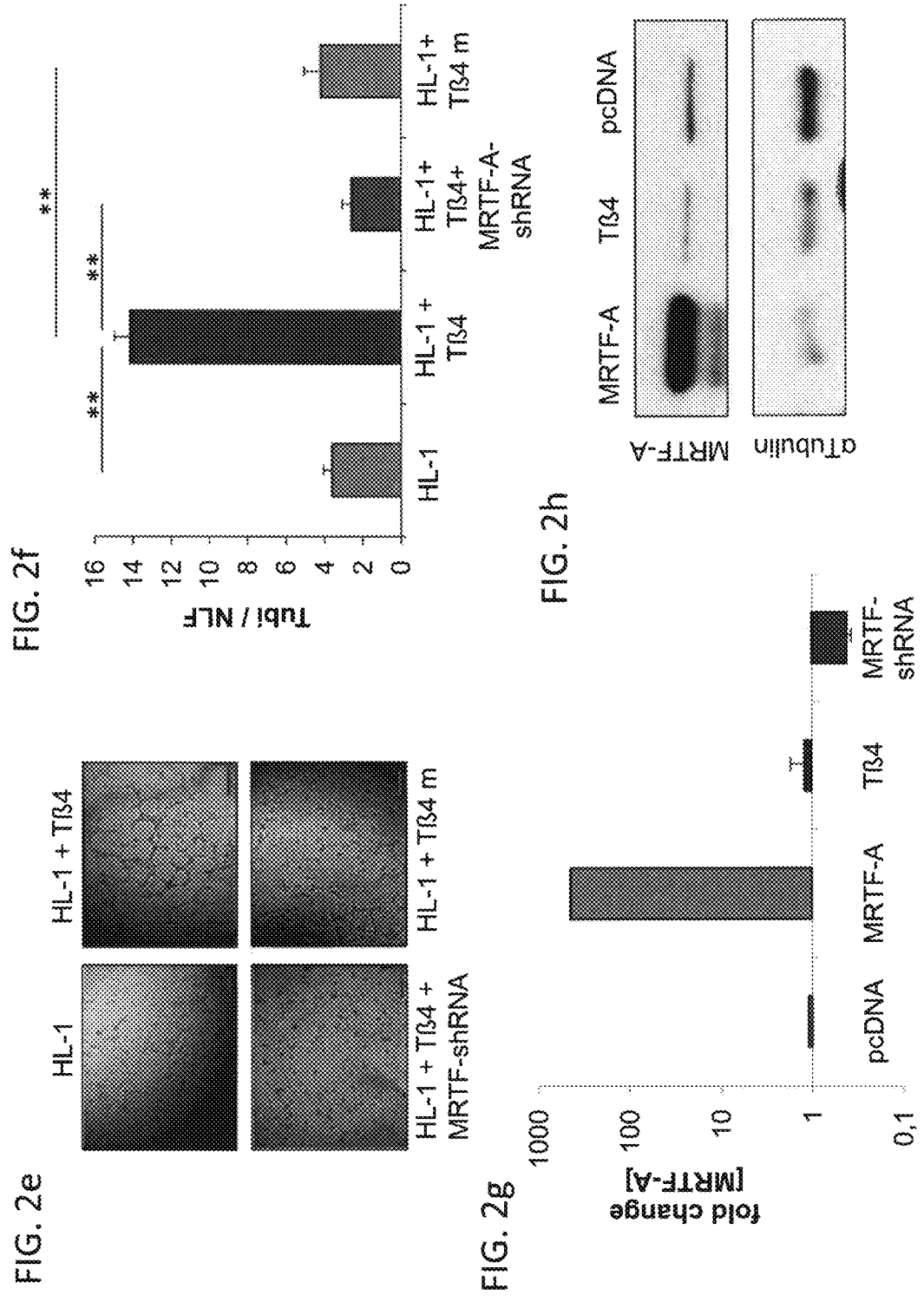

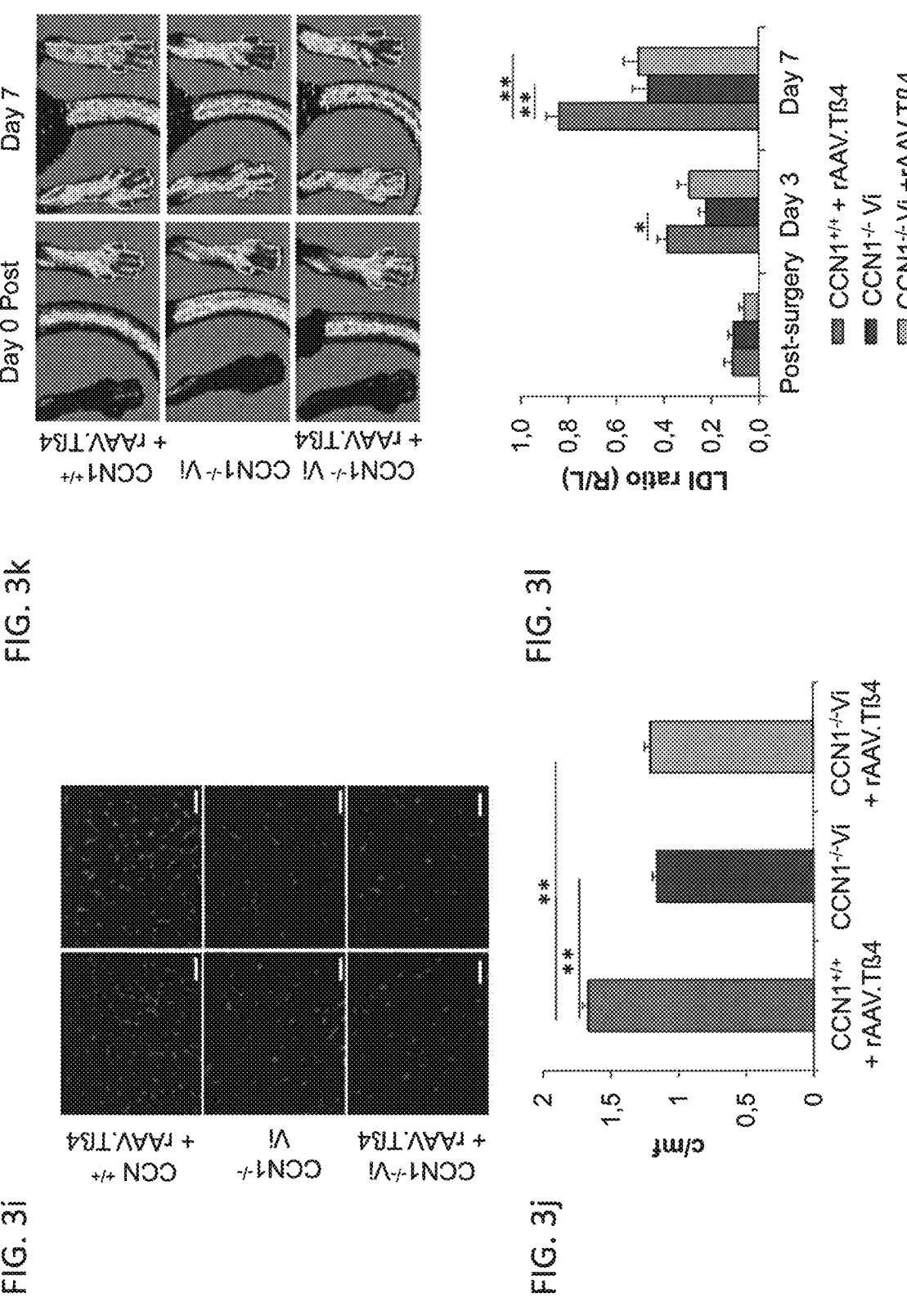

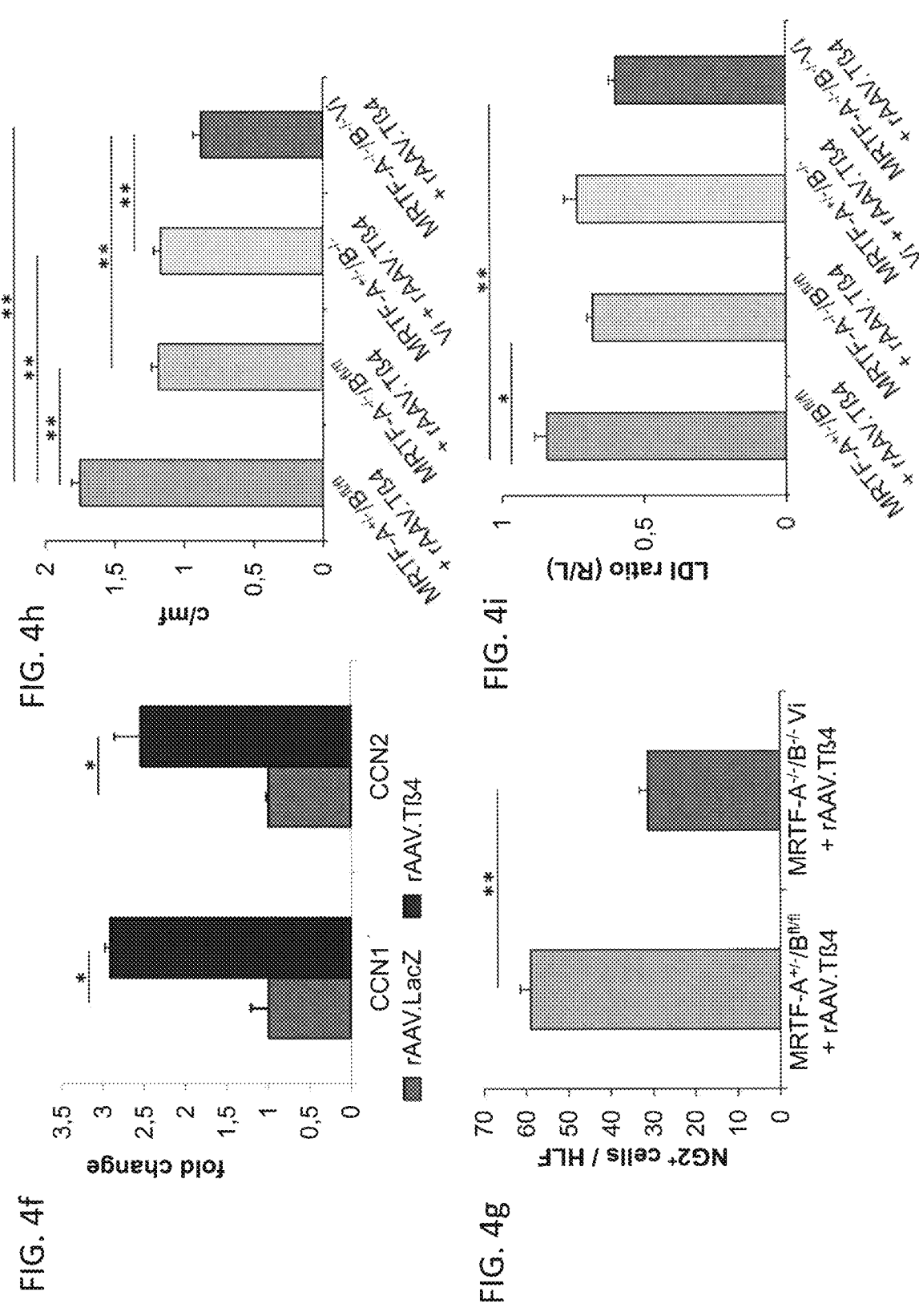

FIG. 6a    Rabbit hind limb ischemia protocol

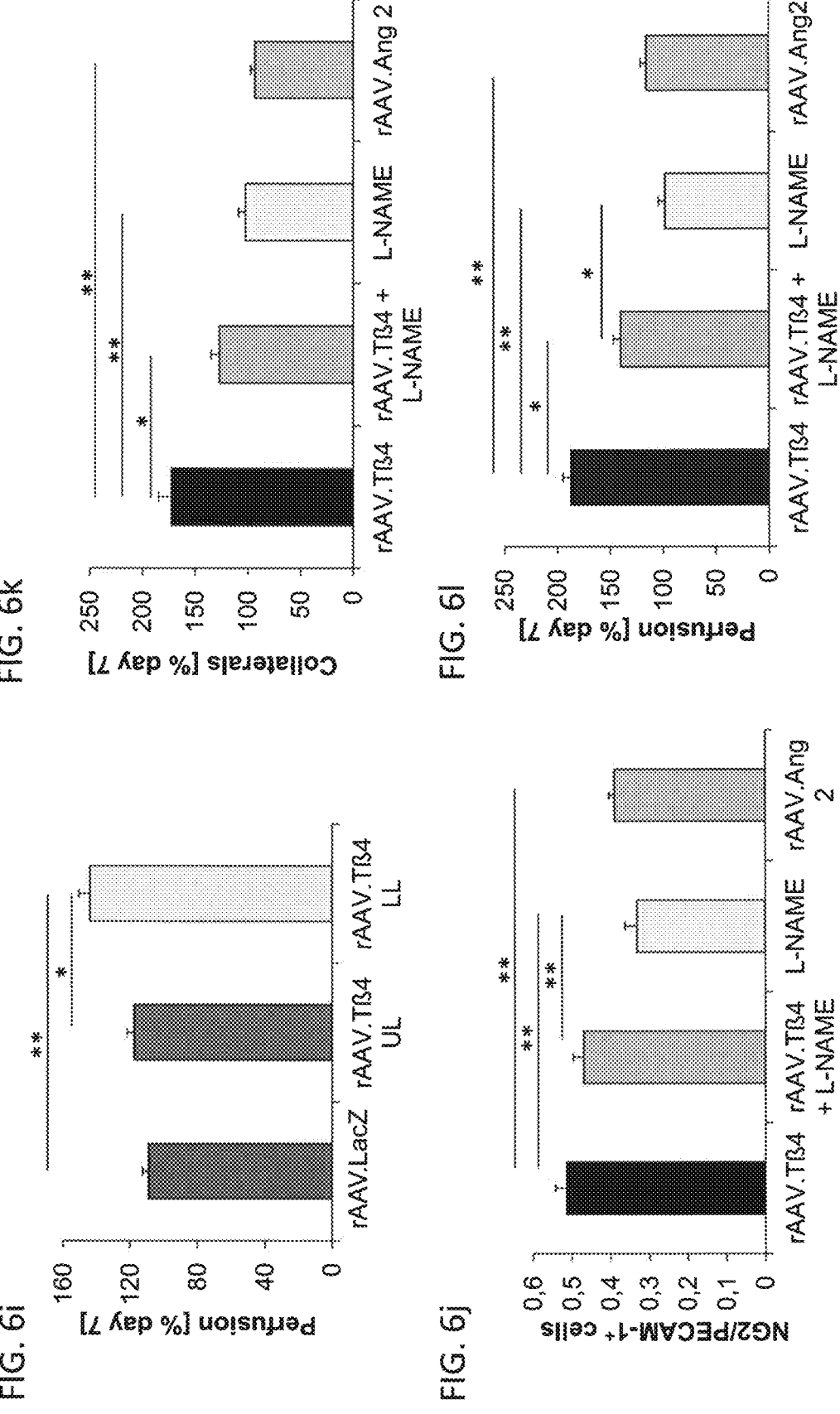

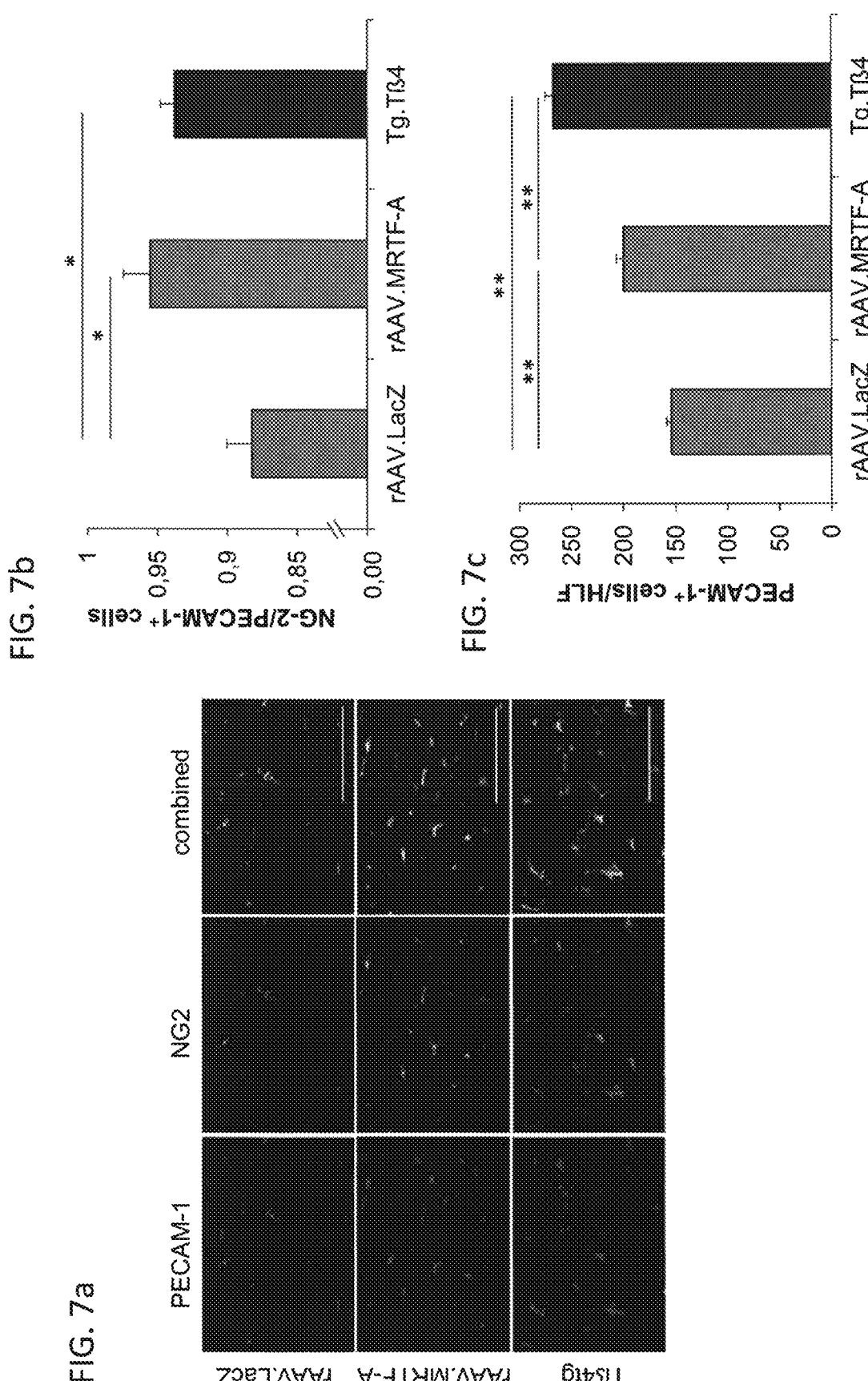

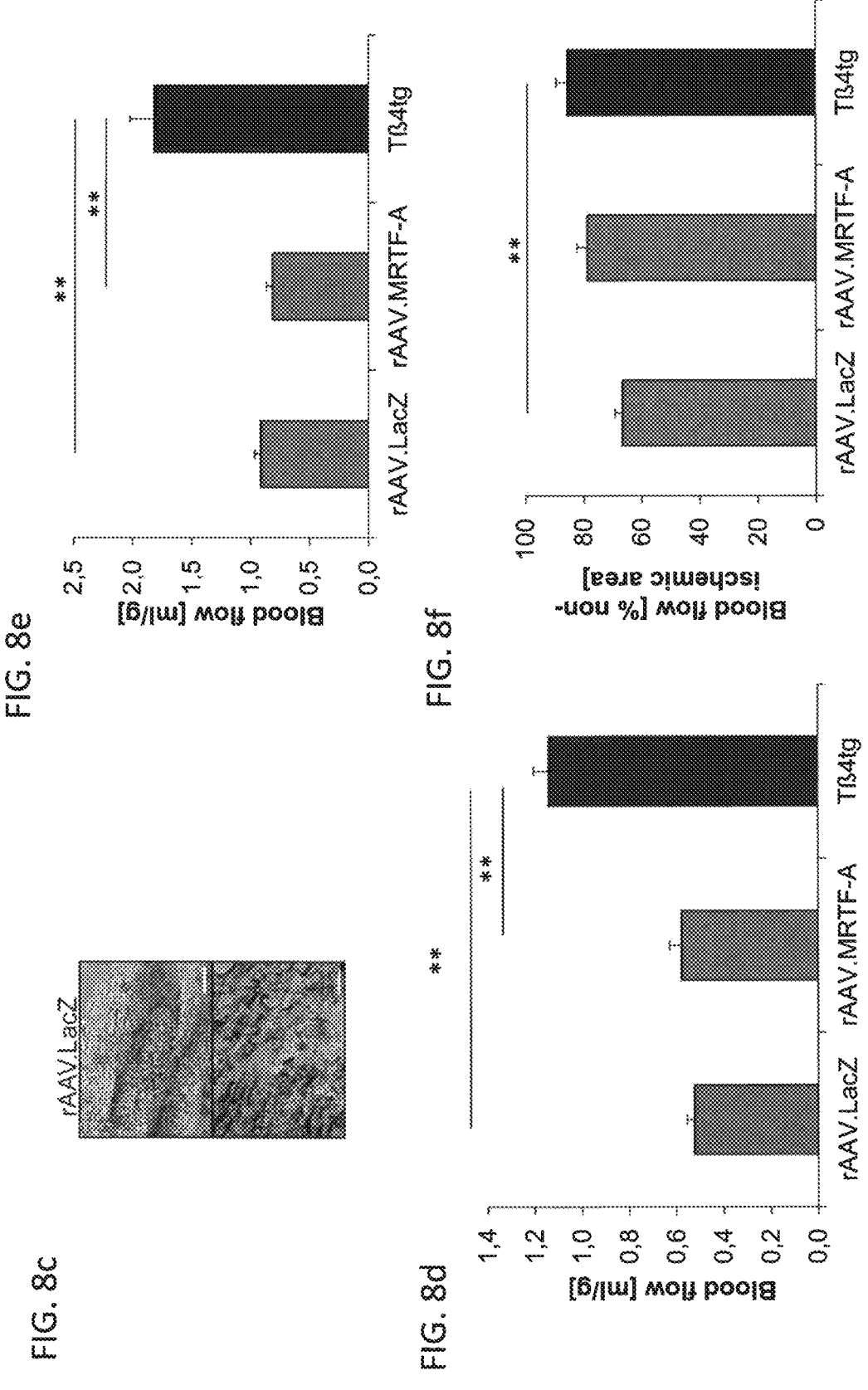

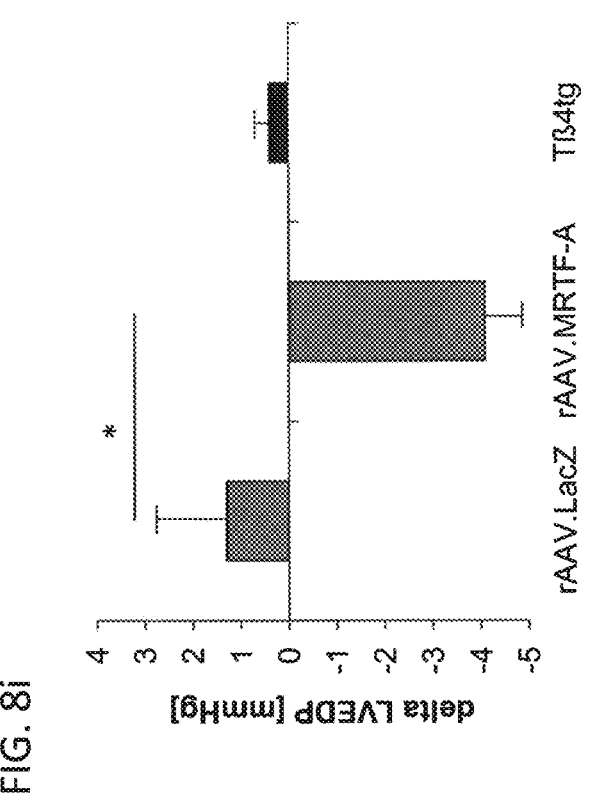
FIG. 8i
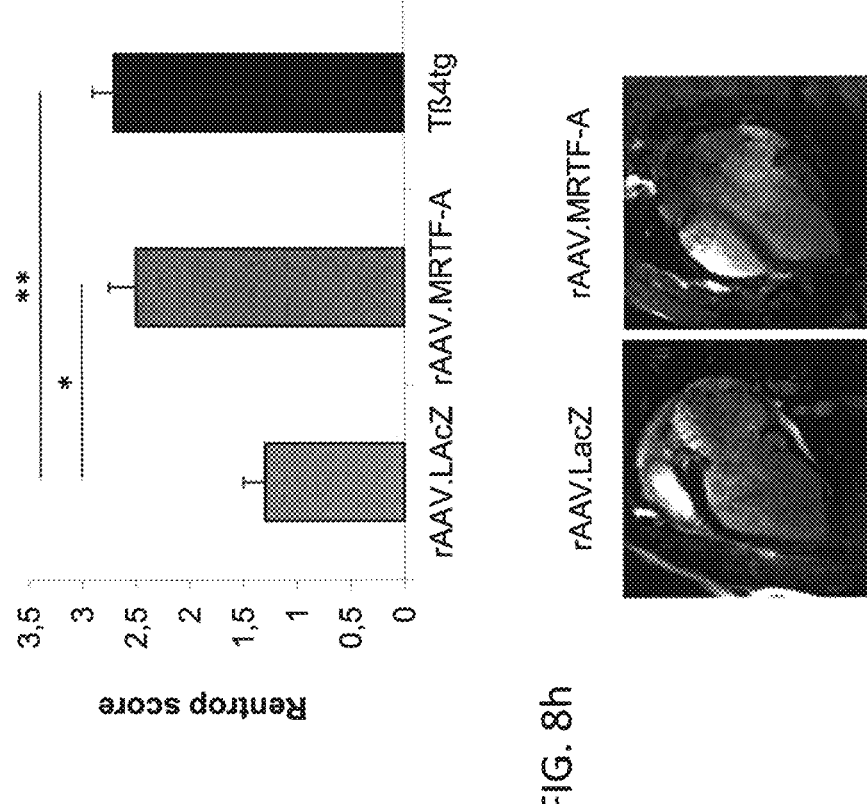
FIG. 8g
FIG. 8h

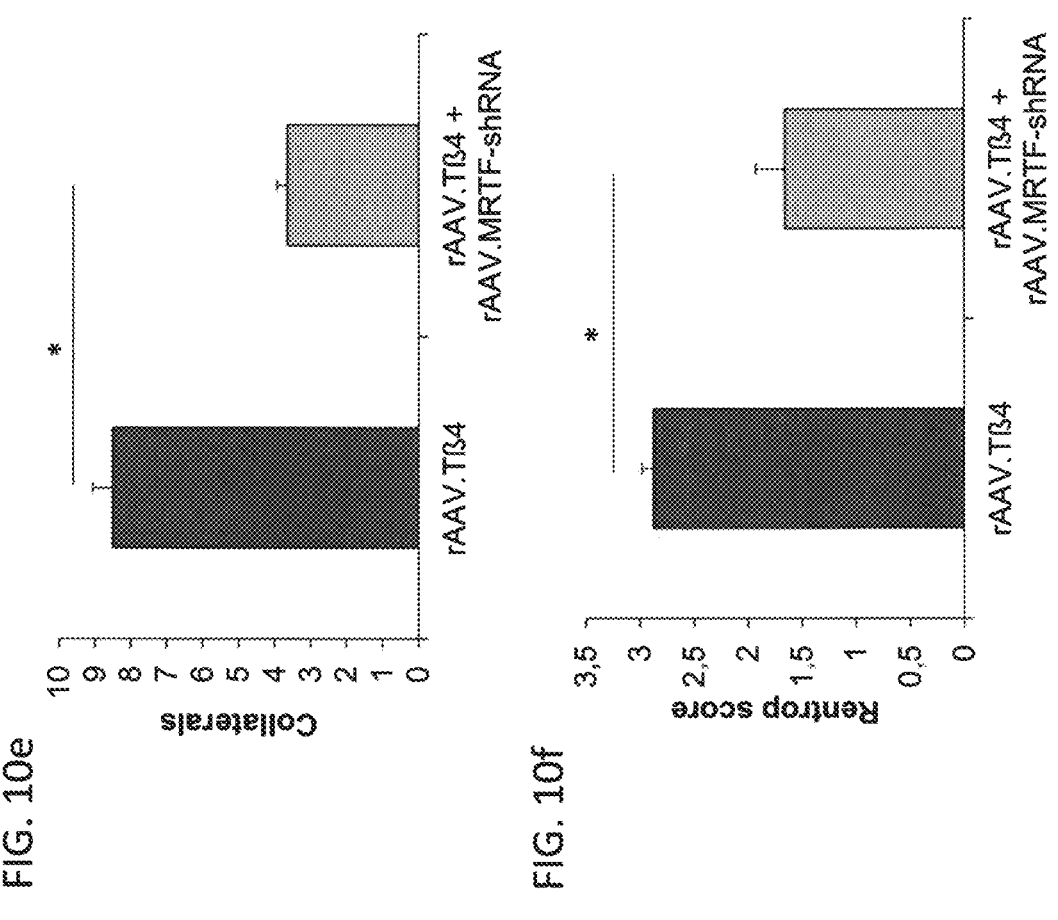
FIG. 10e
FIG. 10f
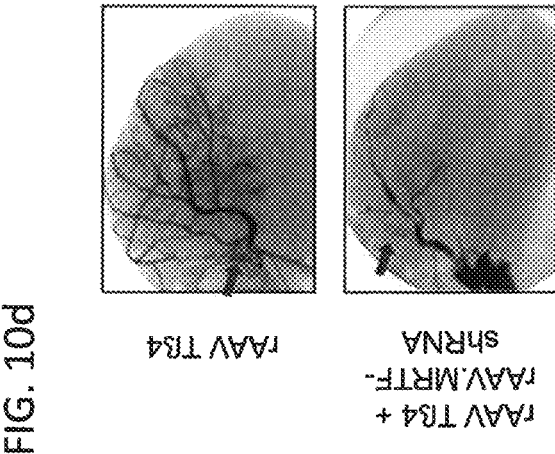
FIG. 10d

INS^C94y transgenic pigs

*Renner et al. Diabetes 2013*

FIG. 11b
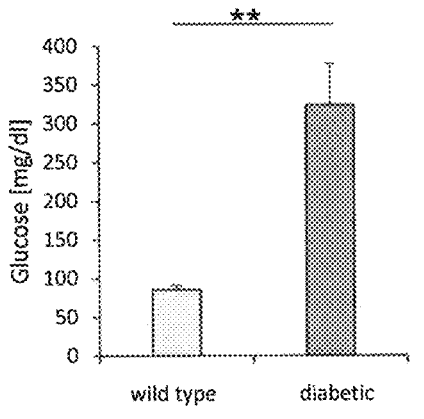
FIG. 11c
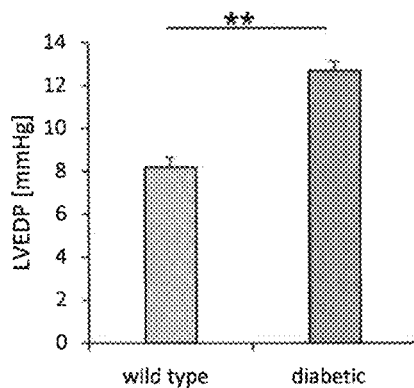
FIG. 11d
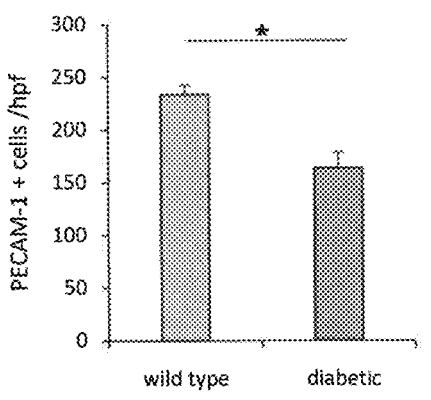
FIG. 11e day 28     day 56 day 28     day 56 hyperchol. control     hyperchol. rAAV.Tß4

FIG. 17a
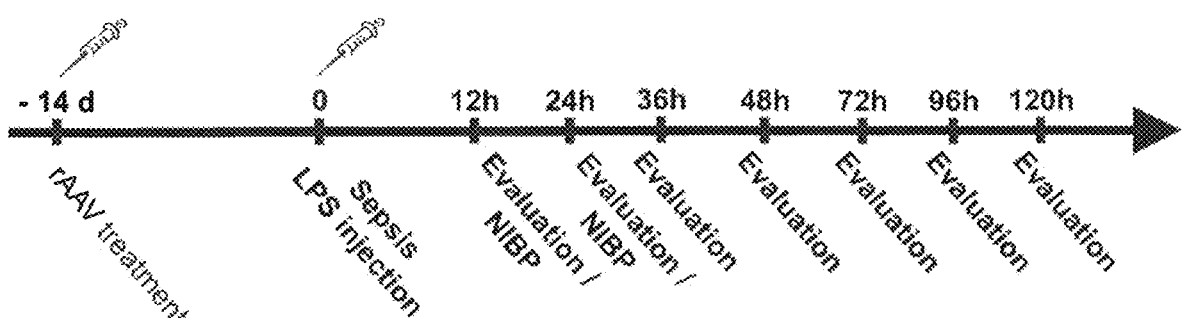
FIG. 17b
| Score | 0 | 5 | 10 | 20 |
|---|---|---|---|---|
| Behavior/ Impairment | normal | light | moderate | comatose |
| Weight loss | 0 - 5 % | 5 - 10% | 10 - 15% | > 15% |
| Pain | none | low | medium | high |
| Ascites | none | low | Medium | high |
| Dyspnoe | none | low | medium | high |
FIG. 17c
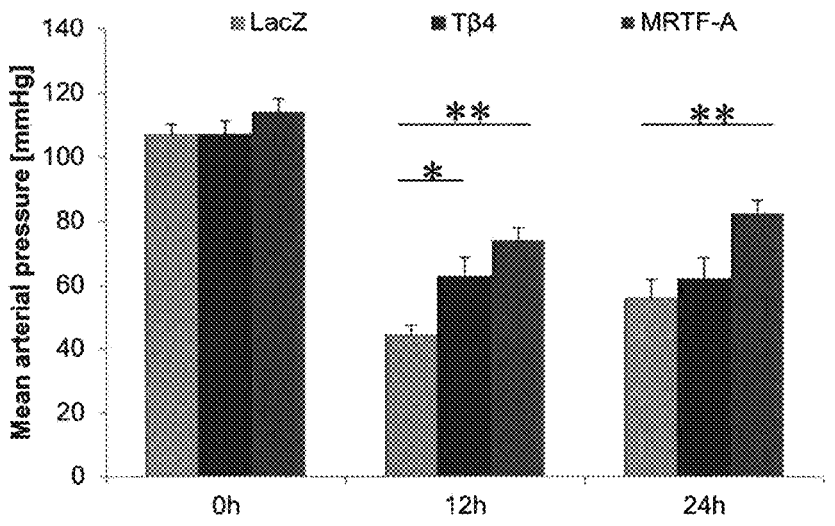

■ Tβ4  ▨ LacZ

Tβ4    LacZ

SEQUENCE LISTING

```
<160> NUMBER OF SEQ ID NOS: 17

<210> SEQ ID NO 1
<211> LENGTH: 69
<212> TYPE: RNA
<213> ORGANISM: Artificial Sequence
<220> FEATURE:
<223> OTHER INFORMATION: MRTF shRNA

<400> SEQUENCE: 1
gauccccgca uggagcuggu ggagaagaau ucaagagauu cuucuccacc agcuccaugu        60
uuuuggaaa                                                                69

<210> SEQ ID NO 2
<211> LENGTH: 23
<212> TYPE: DNA
<213> ORGANISM: Artificial Sqeuence
<220> FEATURE:
<223> OTHER INFORMATION: BGH Forward Primer

<400> SEQUENCE: 2
tctagttgcc agccatctgt tgt                                                23
```

```
<210> SEQ ID NO 3
<211> LENGTH: 18
<212> TYPE: DNA
<213> ORGANISM: Artificial Sequence
<220> FEATURE:
<223> OTHER INFORMATION: BGH Reverse Primer

<400> SEQUENCE: 3
tgggagtggc accttcca                                                        18

<210> SEQ ID NO 4
<211> LENGTH: 20
<212> TYPE: DNA
<213> ORGANISM: Artificial Sequence
<220> FEATURE:
<223> OTHER INFORMATION: GAPDH Forward Primer

<400> SEQUENCE: 4
aattcaacgg cacagtcaag                                                      20

<210> SEQ ID NO 5
<211> LENGTH: 20
<212> TYPE: DNA
<213> ORGANISM: Artificial Sequence
<220> FEATURE:
<223> OTHER INFORMATION: GADPH Reverse Primer

<400> SEQUENCE: 5
atggtggtga agacaccagt                                                      20

<210> SEQ ID NO 6
<211> LENGTH: 21
<212> TYPE: DNA
<213> ORGANISM: Artificial Sequence
<220> FEATURE:
<223> OTHER INFORMATION: TB4 Forward Primer

<400> SEQUENCE: 6
tcatcgatat gtctgacaaa c                                                    21

<210> SEQ ID NO 7
<211> LENGTH: 21
<212> TYPE: DNA
<213> ORGANISM: Artificial Sequence
<220> FEATURE:
<223> OTHER INFORMATION: TB4 Reverse Primer

<400> SEQUENCE: 7
cagcttgctt ctcttgttca a                                                    21

<210> SEQ ID NO 8
<211> LENGTH: 24
<212> TYPE: DNA
<213> ORGANISM: Artificial Sequence
<220> FEATURE:
<223> OTHER INFORMATION: MRTF-A Forward Primer

<400> SEQUENCE: 8
aatccatggg tcgacggtat cgat                                                 24

<210> SEQ ID NO 9
<211> LENGTH: 24
<212> TYPE: DNA
<213> ORGANISM: Artificial Sequence
<220> FEATURE:
<223> OTHER INFORMATION: MRTF-A Reverse Primer
```

-continued

<400> SEQUENCE: 9
ataccatggt caggcaccgg gctt                                          24

<210> SEQ ID NO 10
<211> LENGTH: 20
<212> TYPE: DNA
<213> ORGANISM: Artificial Sequence
<220> FEATURE:
<223> OTHER INFORMATION: CCN1 Forward Primer

<400> SEQUENCE: 10
gctaaacaac tcaacgagga                                               20

<210> SEQ ID NO 11
<211> LENGTH: 21
<212> TYPE: DNA
<213> ORGANISM: Artificial Sequence
<220> FEATURE:
<223> OTHER INFORMATION: CCN1 Reverse Primer

<400> SEQUENCE: 11
ggctgcaact gcgctcctct g                                             21

<210> SEQ ID NO 12
<211> LENGTH: 19
<212> TYPE: DNA
<213> ORGANISM: Artificial Sequence
<220> FEATURE:
<223> OTHER INFORMATION: CCN2 Reverse Primer

<400> SEQUENCE: 12
ccctagctgc ctaccgact                                                19

<210> SEQ ID NO 13
<211> LENGTH: 23
<212> TYPE: DNA
<213> ORGANISM: Artificial Sequence
<220> FEATURE:
<223> OTHER INFORMATION: CCN2 Reverse Primer

<400> SEQUENCE: 13
cattccacag gtcttagaac agg                                           23

<210> SEQ ID NO 14
<211> LENGTH: 20
<212> TYPE: DNA
<213> ORGANISM: Artificial Sequence
<220> FEATURE:
<223> OTHER INFORMATION: Angiopoietin 2 Forward Primer

<400> SEQUENCE: 14
tcgaatacga tgactcggtg                                               20

<210> SEQ ID NO 15
<211> LENGTH: 19
<212> TYPE: DNA
<213> ORGANISM: Artificial Sequence
<220> FEATURE:
<223> OTHER INFORMATION: Angiopoietin 2 Reverse Primer

<400> SEQUENCE: 15
gtttgtccct atttctatc                                                19

<210> SEQ ID NO 16
<211> LENGTH: 7890

```
<212> TYPE: DNA
<213> ORGANISM: Artificial Sequence
<220> FEATURE:
<223> OTHER INFORMATION: pAAV-CMV-mMRTFA (murine)

<400> SEQUENCE: 16
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccagattta     240
attaaggctg cgcgctcgct cgctcactga ggccgcccgg gcaaagcccg ggcgtcgggc     300
gacctttggt cgcccggcct cagtgagcga gcgagcgcgc agagagggag tggccaactc     360
catcactagg ggttccttgt agttaatgat taacccgcca tgctacttat ctacgtagcc     420
atgctctagg aagatcggaa ttcgccctta agctagctag ttattaatag taatcaatta     480
cggggtcatt agttcatagc ccatatatgg agttccgcgt tacataactt acggtaaatg     540
gcccgcctgg ctgaccgccc aacgaccccc gcccattgac gtcaataatg acgtatgttc     600
ccatagtaac gccaataggg actttccatt gacgtcaatg ggtggagtat ttacggtaaa     660
ctgcccactt ggcagtacat caagtgtatc atatgccaag tacgccccct attgacgtca     720
atgacggtaa atggcccgcc tggcattatg cccagtacat gaccttatgg gactttccta     780
cttggcagta catctacgta ttagtcatcg ctattaccat ggtgatgcgg ttttggcagt     840
acatcaatgg gcgtggatag cggtttgact cacggggatt tccaagtctc caccccattg     900
acgtcaatgg gagtttgttt tggcaccaaa atcaacggga ctttccaaaa tgtcgtaaca     960
actccgcccc attgacgcaa atgggcggta ggcgtgtacg gtgggaggtc tatataagca    1020
gagctggttt agtgaaccgt cagatcctgc agaagttggt cgtgaggcac tgggcaggta    1080
agtatcaagg ttacaagaca ggtttaagga ccaatagaa actgggctt gtcgagacag      1140 agaagactct tgcgtttctg ataggcacct attggtctta ctgacatcca ctttgccttt    1200
ctctccacag gtgtccaggc ggccgctcaa acagacacca taacatgctg ccccccttccg   1260 tcattgctgt gaatgggctg gacggaggag gggctggcga aaatgacgac gagccagtgc    1320
tcctgtctct gtctgcggcc cccagccccc agagcgaagc tgttgccaat gaactgcagg    1380
agctgtccct gcagcccgag ctgactctag gcctccatcc tgggaggaac cccaatttac    1440
ctccacttag tgagcggaag aatgtgctgc agttgaagct ccagcagcgg cggacccggg    1500
aggaactggt gagccaaggg atcatgccgc ctttgaaaag ccccgctgca tttcatgagc    1560
agagaagaag cctggagcgg gccaggaccg aggactattt gaaacggaag atccgttccc    1620
ggcccgagag agcagagctg gtcaggatgc acattctgga agagacctcg gctgagcctt    1680
cgctccaggc caagcagctg aagctgaaga gagccaggct ggctgatgac ctcaatgaaa    1740
agattgcaca gaggcctggc cccatggagc tggtggagaa gaatatcctg cctgtggagt    1800
ccagcctgaa ggaggctatc attgtgggcc aggtaaatta cccaaaggta gcagacagtt    1860
cctccttcga cgaggacagc agcgatgccc tgtctcctga gcagcctgcc agccatgagt    1920
cccagggttc agtgccatca cccttggagt cccgagtcag tgatccactg cccagtgcca    1980
cctccatatc acccactcag gttctttctc aactcccaat ggctccggat cctggagaga    2040
cgctttttct ggcagagcag cctcctctgc ctcccgcacc tctgctgccc caagcctag    2100 ccaatggaag catcgtcccc actgccaagc ctgctcccac actcatcaag caaagccaac   2160
```

-continued

```
ccaagtctgc cagcgagaaa tcacagcgca gcaagaaggc caaggagctg aagccaaagg   2220
tgaagaagct caagtaccac cagtacatcc ccccggacca gaagcaggac aagggggcgc   2280
ccgccatgga ctcctcctat gccaagatcc tgcagcagca gcagctcttc ctgcagctgc   2340
agatcctcaa ccagcagcag cagcagcagc agcaacagca ctacaactac caggccatcc   2400
tgcctgcccc tcccaagccc tcggctgaga ctcctggaag cagtgcccct accccatcac   2460
gcagcctctc caccagtagc agccccagct caggcacccc agggcccagc gggctggcac   2520
gccagagcag caccgcacta gctgccaaac caggagccct gccagccaac ctggatgaca   2580
tgaaggtggc agagctgaag caagaactga agttgcggtc ccttcccgtc tcaggcacca   2640
agacagagct gatagaacgc ctgcgtgcct accaagacca agtcagccca gctccaggag   2700
cccccaaggc ccctgccacc acctctgtgc tgtccaaggc tggtgaggta gtggtcgcct   2760
tccctgcggc cctgctaagc acagggtcag ctcttgtaac agcaggcctt gcaccagctg   2820
agatggtggt ggccacagta accagcaatg gcatggtgaa gtttggcagc acaggctcca   2880 cacccccgt gtctcccacc ccttcagagc gctcactgct cagcacgggt gatgagaatt   2940
ccacacctgg ggatgccttt ggtgaaatgg tgacatcgcc gctgacacag ctcaccctgc   3000
aggcctcccc actgcagatc gtgaaggagg agggtgcccg tgctgcgtcc tgctgtctaa   3060
gccctggtgc tcgggctgag ctggagggac tggacaagga ccagatgctg caggagaagg   3120
acaagcagat tgaggagctg acccgaatgc tccaacagaa gcagcagctg gttgagctgc   3180
tgcggctaca gctggagcag cagaagcggg cccagcagcc agccccagcc agcagccctg   3240
tgaagaggga aagtggtttc tccagttgcc agctgagctg ccagccccag ggctctgccc   3300
atgcttttgg ctctggccta gtggttccca ctaccaacca tggagacact caggccccag   3360
cgccagagtc cccacctgtg gtggtgaagc aggaagctgg gccacctgag ccagatctgg   3420
cccccagctc ccagctgctc ttgggctccc agggcaccag cttcctcaag agggtcagcc   3480
ctcctaccct ggtcactgac tctacaggga ctcacctcat cctcactgtg accaataaga   3540
gtgctgatgg ccctggcttg cctgcaggga gcccccagca gcccttgtcc cagcctggtt   3600
ctccagcccc tggtccacct gcccagatgg acctggagca cccacctcag cctccgtttg   3660
caacccccac atctctgctg aagaaggagc cccctggtta tgaagagact gtgacccagc   3720
agcctaagca gcaggaaaat ggctcctcca gtcagcacat ggatgatctg tttgatattc   3780
ttattcagag tggagagatt tcagcagatt tcaaagagcc accatcccta ccaggcaagg   3840
aaaagtcacc tccagcagca gcagcgtatg ggcctccatt gacaccacaa ccctcgcctt   3900
tgagtgaact cccccaagct gctcctccac caggttcccc caccctccca gggcgccttg   3960
aagacttcct ggagagcagc acagggctgc ccctgctgac aagtgggcac gagggaccag   4020
aacccctttc cctcattgat gacctccaca gccagatgct gagcagctcc gccatcctgg   4080 accaccccc atcacccatg gacacctctg aattgcactt tgctcctgag cccagcagtg   4140
gtatgggcct ggacctggct gttggccacc tggacagcat ggactggctg gagctgtcgt   4200
ctggtggccc tgtgctcagc ctggctcccc tcagcactgc agcccccagc ctcttctcga   4260
tggacttcct ggatggacac gacttgcagc tccactggga ttcctgcttg tacccatacg   4320
acgtgccaga ctagaagctt ggatccaatc aacctctgga ttacaaaatt tgtgaaagat   4380
tgactggtat tcttaactat gttgctcctt ttacgctatg tggatacgct gctttaatgc   4440
ctttgtatca tgctattgct tcccgtatgg ctttcatttt ctcctccttg tataaatcct   4500
ggttgctgtc tctttatgag gagttgtggc ccgttgtcag gcaacgtggc gtggtgtgca   4560
```

```
ctgtgtttgc tgacgcaacc cccactggtt ggggcattgc caccacctgt cagctccttt    4620
ccgggacttt cgctttcccc ctccctattg ccacggcgga actcatcgcc gcctgccttg    4680
cccgctgctg gacaggggct cggctgttgg gcactgacaa ttccgtggtg ttgtcgggga    4740
agctgacgtc ctttccatgg ctgctcgcct gtgttgccac ctggattctg cgcgggacgt    4800
ccttctgcta cgtcccttcg gccctcaatc cagcggacct tccttcccgc ggcctgctgc    4860
cggctctgcg gcctcttccg cgtcttcgag atctgcctcg actgtgcctt ctagttgcca    4920
gccatctgtt gtttgcccct cccccgtgcc ttccttgacc ctggaaggtg ccactcccac    4980
tgtcctttcc taataaaatg aggaaattgc atcgcattgt ctgagtaggt gtcattctat    5040
tctggggggt ggggtggggc aggacagcaa gggggaggat tgggaagaca atagcaggca    5100
tgctggggac tcgagttaag ggcgaattcc cgattaggat cttcctagag catggctacg    5160
tagataagta gcatggcggg ttaatcatta actacaagga acccctagtg atggagttgg    5220
ccactccctc tctgcgcgct cgctcgctca ctgaggccgg gcgaccaaag gtcgcccgac    5280
gcccgggctt tgcccgggcg gcctcagtga gcgagcgagc gcgcagcctt aattaaccta    5340
attcactggc cgtcgtttta caacgtcgtg actgggaaaa ccctggcgtt acccaactta    5400
atcgccttgc agcacatccc cctttcgcca gctggcgtaa tagcgaagag gcccgcaccg    5460
atcgcccttc ccaacagttg cgcagcctga atggcgaatg ggacgcgccc tgtagcggcg    5520
cattaagcgc ggcgggtgtg gtggttacgc gcagcgtgac cgctacactt gccagcgccc    5580
tagcgcccgc tcctttcgct ttcttccctt cctttctcgc cacgttcgcc ggctttcccc    5640
gtcaagctct aaatcggggg ctccctttag ggttccgatt tagtgcttta cggcacctcg    5700
accccaaaaa acttgattag ggtgatggtt cacgtagtgg gccatcgccc cgatagacgg    5760
ttttttcgcc tttgacgctg gagttcacgt tcctcaatag tggactcttg ttccaaactg    5820
gaacaacact caaccctatc tcggtctatt cttttgattt ataagggatt tttccgattt    5880
cggcctattg gttaaaaaat gagctgattt aacaaaaatt taacgcgaat tttaacaaaa    5940
tattaacgtt tataatttca ggtggcatct ttcggggaaa tgtgcgcgga acccctattt    6000
gtttattttt ctaaatacat tcaaatatgt atccgctcat gagacaataa ccctgataaa    6060
tgcttcaata atattgaaaa aggaagagta tgagtattca acatttccgt gtcgccctta    6120
ttcccttttt tgcggcattt tgccttcctg ttttttgctca cccagaaacg ctggtgaaag    6180
taaaagatgc tgaagatcag ttgggtgcac gagtgggtta catcgaactg gatctcaata    6240
gtggtaagat ccttgagagt tttcgccccg aagaacgttt tccaatgatg agcacttttta    6300 aagttctgct atgtggcgcg gtattatccc gtattgacgc cgggcaagag caactcggtc    6360
gccgcataca ctattctcag aatgacttgg ttgagtactc accagtcaca gaaaagcatc    6420
ttacggatgg catgacagta agagaattat gcagtgctgc cataaccatg agtgataaca    6480
ctgcggccaa cttacttctg acaacgatcg gaggaccgaa ggagctaacc gcttttttgc    6540
acaacatggg ggatcatgta actcgccttg atcgttggga accggagctg aatgaagcca    6600
taccaaacga cgagcgtgac accacgatgc ctgtagtaat ggtaacaacg ttgcgcaaac    6660
tattaactgg cgaactactt actctagctt cccggcaaca attaatagac tggatggagg    6720
cggataaagt tgcaggacca cttctgcgct cggcccttcc ggctggctgg tttattgctg    6780
ataaatctgg agccggtgag cgtgggtctc gcggtatcat tgcagcactg gggccagatg    6840
gtaagccctc ccgtatcgta gttatctaca cgacggggag tcaggcaact atggatgaac    6900
```

-continued

```
gaaatagaca gatcgctgag ataggtgcct cactgattaa gcattggtaa ctgtcagacc     6960
aagtttactc atatatactt tagattgatt taaaacttca ttttttaattt aaaaggatct    7020 aggtgaagat cctttttgat aatctcatga ccaaaatccc ttaacgtgag ttttcgttcc     7080
actgagcgtc agacccgta gaaaagatca aaggatcttc ttgagatcct ttttttctgc     7140
gcgtaatctg ctgcttgcaa acaaaaaaac caccgctacc agcggtggtt tgtttgccgg     7200
atcaagagct accaactctt tttccgaagg taactggctt cagcagagcg cagataccaa     7260
atactgtcct tctagtgtag ccgtagttag gccaccactt caagaactct gtagcaccgc     7320
ctacatacct cgctctgcta atcctgttac cagtggctgc tgccagtggc gataagtcgt     7380
gtcttaccgg gttggactca agacgatagt taccggataa ggcgcagcgg tcgggctgaa     7440
cggggggttc gtgcacacag cccagcttgg agcgaacgac ctacaccgaa ctgagatacc     7500
tacagcgtga gctatgagaa agcgccacgc ttcccgaagg gagaaaggcg gacaggtatc     7560
cggtaagcgg cagggtcgga acaggagagc gcacgaggga gcttccaggg ggaaacgcct     7620
ggtatcttta tagtcctgtc gggtttcgcc acctctgact tgagcgtcga ttttgtgat      7680 gctcgtcagg gggcggagc ctatggaaaa acgccagcaa cgcggccttt ttacggttcc      7740
tggccttttg ctgcggtttt gctcacatgt tctttcctgc gttatcccct gattctgtgg     7800
ataaccgtat taccgccttt gagtgagctg ataccgctcg ccgcagccga acgaccgagc     7860
gcagcgagtc agtgagcgag gaagcggaag                                       7890
```

```
<210> SEQ ID NO 17
<211> LENGTH: 7596
<212> TYPE: DNA
<213> ORGANISM: Artificial Sequence
<220> FEATURE:
<223> OTHER INFORMATION: pAAV-CMV-hMRTF-A (human)

<400> SEQUENCE: 17
```

```
agcgcccaat acgcaaaccg cctctccccg cgcgttggcc gattcattaa tgcagctggc       60
acgacaggtt tcccgactgg aaagcgggca gtgagcgcaa cgcaattaat gtgagttagc      120
tcactcatta ggcaccccag gctttacact ttatgcttcc ggctcgtatg ttgtgtggaa      180
ttgtgagcgg ataacaattt cacacaggaa acagctatga ccatgattac gccagattta     240
attaaggctg cgcgctcgct cgctcactga ggccgcccgg gcaaagcccg ggcgtcgggc      300
gacctttggt cgcccggcct cagtgagcga gcgagcgcgc agagagggag tggccaactc      360
catcactagg ggttccttgt agttaatgat taacccgcca tgctacttat ctacgtagcc      420
atgctctagg aagatcggaa ttcgccctta agctagctag ttattaatag taatcaatta     480
cggggtcatt agttcatagc ccatatatgg agttccgcgt tacataactt acggtaaatg      540
gcccgcctgg ctgaccgccc aacgaccccc gcccattgac gtcaataatg acgtatgttc      600
ccatagtaac gccaataggg actttccatt gacgtcaatg ggtggagtat ttacggtaaa      660
ctgcccactt ggcagtacat caagtgtatc atatgccaag tacgccccct attgacgtca      720
atgacggtaa atggcccgcc tggcattatg cccagtacat gaccttatgg gactttccta     780
cttggcagta catctacgta ttagtcatcg ctattaccat ggtgatgcgg ttttggcagt     840
acatcaatgg gcgtggatag cggtttgact cacggggatt tccaagtctc cacccattg      900 acgtcaatgg gagtttgttt tggcaccaaa atcaacggga ctttccaaaa tgtcgtaaca     960
actccgcccc attgacgcaa atgggcggta ggcgtgtacg gtgggaggtc tatataagca    1020
gagctggttt agtgaaccgt cagatcctgc agaagttggt cgtgaggcac tgggcaggta    1080
```

-continued

```
agtatcaagg ttacaagaca ggtttaagga gaccaataga aactgggctt gtcgagacag   1140
agaagactct tgcgtttctg ataggcacct attggtctta ctgacatcca cttttgccttt  1200 ctctccacag gtgtccaggc ggccgctcaa acagacacca taacatgccg cctttgaaaa   1260
gtccagccgc atttcatgag cagagaagga gcttggagcg ggccaggaca gaggactatc   1320
tcaaacggaa gattcgttcc cggccggaga gatcggagct ggtcaggatg cacattttgg   1380
aagagacctc ggctgagcca tccctccagg ccaagcagct gaagctgaag agagccagac   1440
tagccgatga cctcaatgag aagattgcac agaggcctgg ccccatggag ctggtggaga   1500
agaacatcct tcctgttgag tccagcctga aggaagccat cattgtgggc caggtgaact   1560
atcccaaagt agcagacagc tcttccttcg atgaggacag cagcgatgcc ttatcccccg   1620
agcagcctgc cagccatgag tcccagggtt ctgtgccgtc acccctggag gcccgagtca   1680
gcgaaccact gctcagtgcc acctctgcat cccccaccca ggttgtgtct caacttccga   1740
tgggccggga ttccagagaa atgctttttcc tggcagagca gcctcctctg cctcccccac   1800
ctctgctgcc tcccagcctc accaatggaa ccactatccc cactgccaag tccacccca    1860 cactcattaa gcaaagccaa cccaagtctg ccagtgagaa gtcacagcgc agcaagaagg   1920
ccaaggagct gaagccaaag gtgaagaagc tcaagtacca ccagtacatc cccccggacc   1980
agaagcagga caggggggca cccccccatgg actcatccta cgccaagatc ctgcagcagc   2040
agcagctctt cctccagctg cagatcctca accagcagca gcagcagcac cacaactacc   2100
aggccatcct gcctgccccg ccaaagtcag caggcgaggc cctgggaagc agcgggaccc   2160
ccccagtacg cagcctctcc actaccaata gcagctccag ctcgggcgcc cctgggccct   2220
gtgggctggc acgtcagaac agcacctcac tgactggcaa gccgggagcc ctgccggcca   2280
acctggacga catgaaggtg gcagagctga agcaggagct gaagttgcga tcactgcctg   2340
tctcgggcac caaaactgag ctgattgagc gccttcgagc ctatcaagac caaatcagcc   2400
ctgtgccagg agcccccaag gcccctgccg ccacctctat cctgcacaag gctggcgagg   2460
tggtggtagc cttcccagcg gcccggctga gcacggggcc agccctggtg gcagcaggcc   2520
tggctccagc tgaggtggtg gtggccacgg tggccagcag tggggtggtg aagtttggca   2580
gcacgggctc cacgcccccc gtgtctccca cccctcgga gcgctcactg ctcagcacgg    2640
gcgatgaaaa ctccaccccc ggggacacct ttggtgagat ggtgacatca cctctgacgc   2700
agctgaccct gcaggcctcg ccactgcaga tcctcgtgaa ggaggagggc ccccgggccg   2760
ggtcctgttg cctgagccct gggggggcggg cggagctaga ggggcgcgac aaggaccaga   2820
tgctgcagga gaaagacaag cagatcgagg cgctgacgcg catgctccgg cagaagcagc   2880
agctggtgga gcggctcaag ctgcagctgg agcaggagaa gcgagcccag cagcccgccc   2940
ccgcccccgc cccccctcggc accccgtga agcaggagaa cagcttctcc agctgccagc   3000
tgagccagca gcccctgggc cccgctcacc cattcaaccc cagcctggcg ccccagcca    3060 ccaaccacat agacccttgt gctgtggccc cggggccccc gtccgtggtg gtgaagcagg   3120
aagccttgca gcctgagccc gagccggtcc ccgccccca gttgcttctg gggcctcagg    3180
gccccagcct catcaagggg gttgcacctc ccaccctcat caccgactcc acagggaccc   3240
accttgtcct caccgtgacc aataagaatg cagacagccc tggcctgtcc agtgggagcc   3300 cccagcagc ctcgtcccag cctggctctc cagcgcctgc cccctctgcc cagatggacc    3360
tggagcaccc actgcagccc ctctttggga cccccacttc tctgctgaag aaggaaccac   3420
```

```
ctggctatga ggaagccatg agccagcagc ccaaacagca ggaaaatggt tcctcaagcc   3480
agcagatgga cgacctgttt gacattctca ttcagagcgg agaaatttca gcagatttca   3540
aggagccgcc atccctgcca gggaaggaga agccatcccc gaagacagtc tgtgggtccc   3600
ccctggcagc acagccatca ccttctgctg agctcccccca ggctgcccca cctcctccag   3660
gctcaccctc cctccctgga cgcctggagg acttcctgga gagcagcacg gggctgcccc   3720
tgctgaccag tgggcatgac gggccagagc cccctttccct cattgacgac ctccatagcc   3780
agatgctgag cagcactgcc atcctggacc acccccgtc acccatggac acctcggaat   3840
tgcactttgt tcctgagccc agcagcacca tgggcctgga cctggctgat ggccacctgg   3900
acagcatgga ctggctggag ctgtcgtcag gtggtcccgt gctgagccta gcccccctca   3960
gcaccacagc ccccagcctc ttctccacag acttcctcga tggccatgat ttgcagctgc   4020
actgggattc ctgcttgtag aagcttggat ccaatcaacc tctggattac aaaatttgtg   4080
aaagattgac tggtattctt aactatgttg ctccttttac gctatgtgga tacgctgctt   4140
taatgccttt gtatcatgct attgcttccc gtatggcttt cattttctcc tccttgtata   4200
aatcctggtt gctgtctctt tatgaggagt tgtggcccgt tgtcaggcaa cgtggcgtgg   4260
tgtgcactgt gtttgctgac gcaacccccca ctggttgggg cattgccacc acctgtcagc   4320
tcctttccgg gactttcgct ttccccctcc ctattgccac ggcggaactc atcgccgcct   4380
gccttgcccg ctgctggaca ggggctcggc tgttgggcac tgacaattcc gtggtgttgt   4440
cggggaagct gacgtccttt ccatggctgc tcgcctgtgt tgccacctgg attctgcgcg   4500
ggacgtcctt ctgctacgtc ccttcggccc tcaatccagc ggaccttcct tcccgcggcc   4560
tgctgccggc tctgcggcct cttccgcgtc ttcgagatct gcctcgactg tgccttctag   4620
ttgccagcca tctgttgttt gcccctcccc cgtgccttcc ttgaccctgg aaggtgccac   4680
tcccactgtc ctttcctaat aaaatgagga aattgcatcg cattgtctga gtaggtgtca   4740
ttctattctg ggggtgggg tggggcagga cagcaagggg gaggattggg aagacaatag   4800
caggcatgct ggggactcga gttaagggcg aattcccgat taggatcttc ctagagcatg   4860
gctacgtaga taagtagcat ggcgggttaa tcattaacta caaggaaccc ctagtgatgg   4920
agttggccac tccctctctg cgcgctcgct cgctcactga ggccgggcga ccaaaggtcg   4980
cccgacgccc gggctttgcc cgggcggcct cagtgagcga gcgagcgcgc agccttaatt   5040
aacctaattc actggccgtc gttttacaac gtcgtgactg ggaaaaccct ggcgttaccc   5100
aacttaatcg ccttgcagca catccccctt cgccagctg gcgtaatagc gaagaggccc   5160
gcaccgatcg cccttcccaa cagttgcgca gcctgaatgg cgaatgggac gcgccctgta   5220
gcggcgcatt aagcgcggcg ggtgtggtgg ttacgcgcag cgtgaccgct acacttgcca   5280
gcgccctagc gcccgctcct ttcgctttct cccttcctt tctcgccacg ttcgccggct   5340
ttccccgtca agctctaaat cggggggctcc ctttagggtt ccgatttagt gctttacggc   5400
acctcgaccc caaaaaactt gattagggtg atggttcacg tagtgggcca tcgccccgat   5460
agacggtttt tcgccctttg acgctggagt tcacgttcct caatagtgga ctcttgttcc   5520
aaactggaac aacactcaac cctatctcgg tctattcttt tgatttataa gggattttc   5580 cgatttcggc ctattggtta aaaaatgagc tgatttaaca aaaatttaac gcgaattta   5640 acaaaatatt aacgtttata atttcaggtg gcatctttcg gggaaatgtg cgcggaaccc   5700
ctatttgttt attttctaa atacattcaa atatgtatcc gctcatgaga caataaccct   5760
gataaatgct tcaataatat tgaaaaagga agagtatgag tattcaacat ttccgtgtcg   5820
```

-continued

```
cccttattcc cttttttgcg gcattttgcc ttcctgtttt tgctcaccca gaaacgctgg    5880
tgaaagtaaa agatgctgaa gatcagttgg gtgcacgagt gggttacatc gaactggatc    5940
tcaatagtgg taagatcctt gagagttttc gccccgaaga acgttttcca atgatgagca    6000
cttttaaagt tctgctatgt ggcgcggtat tatcccgtat tgacgccggg caagagcaac    6060
tcggtcgccg catacactat tctcagaatg acttggttga gtactcacca gtcacagaaa    6120
agcatcttac ggatggcatg acagtaagag aattatgcag tgctgccata accatgagtg    6180
ataacactgc ggccaactta cttctgacaa cgatcggagg accgaaggag ctaaccgctt    6240
ttttgcacaa catgggggat catgtaactc gccttgatcg ttgggaaccg gagctgaatg    6300
aagccatacc aaacgacgag cgtgacacca cgatgcctgt agtaatggta acaacgttgc    6360
gcaaactatt aactggcgaa ctacttactc tagcttcccg gcaacaatta atagactgga    6420
tggaggcgga taaagttgca ggaccacttc tgcgctcggc ccttccggct ggctggttta    6480
ttgctgataa atctggagcc ggtgagcgtg ggtctcgcgg tatcattgca gcactggggc    6540
cagatggtaa gccctcccgt atcgtagtta tctacacgac ggggagtcag gcaactatgg    6600
atgaacgaaa tagacagatc gctgagatag gtgcctcact gattaagcat tggtaactgt    6660
cagaccaagt ttactcatat atactttaga ttgatttaaa acttcatttt taatttaaaa    6720
ggatctaggt gaagatcctt tttgataatc tcatgaccaa aatcccttaa cgtgagtttt    6780
cgttccactg agcgtcagac cccgtagaaa agatcaaagg atcttcttga tcctttttt    6840 ttctgcgcgt aatctgctgc ttgcaaacaa aaaaaccacc gctaccagcg gtggtttgtt    6900
tgccggatca gagctacca actctttttc cgaaggtaac tggcttcagc agagcgcaga    6960
taccaaatac tgtccttcta gtgtagccgt agttaggcca ccacttcaag aactctgtag    7020
caccgcctac atacctcgct ctgctaatcc tgttaccagt ggctgctgcc agtggcgata    7080
agtcgtgtct taccgggttg gactcaagac gatagttacc ggataaggcg cagcggtcgg    7140
gctgaacggg gggttcgtgc acacagccca gcttggagcg aacgacctac accgaactga    7200
gatacctaca gcgtgagcta tgagaaagcg ccacgcttcc cgaagggaga aaggcggaca    7260
ggtatccggt aagcggcagg gtcggaacag gagagcgcac gagggagctt ccaggggaa    7320 acgcctggta tctttatagt cctgtcgggt ttcgccacct ctgacttgag cgtcgatttt    7380
tgtgatgctc gtcagggggg cggagcctat ggaaaaacgc cagcaacgcg gcctttttac    7440
ggttcctggc cttttgctgc ggttttgctc acatgttctt tcctgcgtta tcccctgatt    7500
ctgtggataa ccgtattacc gcctttgagt gagctgatac cgctcgccgc agccgaacga    7560
ccgagcgcag cgagtcagtg agcgaggaag cggaag                                7596
```

AAV VECTORS FOR VASCULAR GENE THERAPY IN CORONARY HEART DISEASE AND PERIPHERAL ISCHEMIA

CROSS-REFERENCE TO RELATED APPLICATIONS

This application is a continuation of U.S. Ser. No. 15/303,823, filed on Oct. 13, 2016, which is a national phase entry under 35 U.S.C. § 371 of International Patent Application PCT/EP2015/057987, filed Apr. 13, 2015, published as International Patent Publication WO 2015/158667 on Oct. 22, 2015, which claims the benefit of German Patent Application DE 10 2014 207 153.4, filed on Apr. 14, 2014; a, the contents of all are hereby incorporated by reference.

REFERENCE TO A SEQUENCE LISTING

This application contains a Sequence Listing in computer readable form. The computer readable form is incorporated herein by reference.

FIELD OF THE INVENTION

The invention is the field of gene therapy. In particular, the invention is directed to providing gene therapy for coronary heart disease and peripheral ischemia in mammals.

BACKGROUND OF THE INVENTION

In industrialized countries, coronary heart disease remains the most common cause of death, in spite of improved treatments such as revascularization of an occluded coronary vessel (Lloyd-Jones et al., *Circulation* 2010, 121:e46-e215). Besides the manifestation of coronary heart disease as an acute heart attack, myocardial ischemia may occur through a slow, chronic occlusion of a coronary vessel, which can progress to heart insufficiency and even to cardiac failure (Suero et al., *J Am Coll Cardiol* 2001, 38:409-14).

Chronic ischemic disease of the heart or peripheral muscle is presently treated using surgical or interventional measures in order to revascularize constricted or occluded vascular networks. Although drug therapy following the re-opening of an occluded vessel, and thus event-free survival of patients, has been greatly improved in the last years, a number of patients still develop heart insufficiency (Levy et al., *N Engl J Med* 2002, 347:1397-402). In a growing population of patients, conventional therapeutic strategies become exhausted and clinical benefit is then expected from adjuvant neovascularization therapies (angiogenesis/arteriogenesis).

Previous pre-clinical (Kupatt et al., *J Am Coll Cardiol* 2010, 56:414-22) and clinical studies (Rissanen and Ylä-Herttuala, *Mol Ther* 2007, 15:1233-47) failed to reveal any increase in perfusion, if angiogenesis (capillary growth) was reinforced in the absence of microvessel maturation, i.e. recruiting of pericytes and smooth muscle cells (Jain, *Nat Med* 2003, 9:685-693; Potente et al., *Cell* 2011, 146:873-887). Furthermore, angiogenesis (collateral growth), a substantial element of improvement in flow-through, did not prolong walking time in patients afflicted with limb ischemia when supporting GM-CSF treatment was applied without induction of microvessel growth and stabilization (van Royen et al., *Circulation* 2005, 112:1040-6). In contrast, adaptive collateralization (Schierling et al., *J Vasc Res* 2009, 46:365-374) occurred when a proangiogenic factor like VEGF-A was combined with the maturation factors PDGF-B (Kupatt et al., *J Am Coll Cardiol* 2010, 56:414-22) or angiopoietin-1 (Smith et al., *J Am Coll Cardiol* 2012, 59:1320-8). On the other hand, inhibition of NF-κB signaling, hampering VEGF-A and PDGF-B expression led to a hyper-branched and immature collateral network (Tirziu et al., *Circulation* 2012, 126:2589-600). Consequently, an increase in stable and regulated microvessels is necessary for a successful induction of functional neovascularization.

Event-free survival of patients might be improved significantly using gene therapy in cases of angiogenesis, arteriogenesis, in addition to improved heart function. However, for these purposes, it is necessary to select the correct gene therapy vector and target cells. The present invention advantageously solves these problems through the use of AAV vectors in vascular gene therapy strategies against coronary heart disease.

SUMMARY OF THE INVENTION

In one embodiment, the invention relates to an adeno-associated viral vector (AAV vector) comprising a gene encoding a myocardin-related transcription factor A (MRTF-A).

In another embodiment, the invention relates to an adeno-associated viral vector (AAV vector) comprising a gene encoding a thymosin β4 (Tβ4).

The AAV vector can be an AAV2/9 or an AAV vector pseudotyped with envelope proteins of AAV9, preferably AAV2.9, AAV1.9, or AAV6.9.

In one embodiment, the AAV vector comprises a gene encoding an MRTF-A.

In one embodiment, the invention relates to an adeno-associated viral vector (AAV vector) comprising a gene encoding a myocardin-related transcription factor A (MRTF-A), and a second gene encoding a thymosin β4 (Tβ4) and/or a third gene encoding an MRTF-A.

In one embodiment, the first gene is under the control of a cardio-specific promoter. In one embodiment, the first gene is under the control of a CMV promoter, an MRC2 promoter, a MyoD promoter, or a troponin promoter.

Furthermore, the invention also relates to a pharmaceutical composition comprising an AAV vector of the invention and a pharmaceutically acceptable carrier.

The invention further relates to an AAV vector of the invention or a pharmaceutical composition of the invention for use as a medicament. In one embodiment, the AAV vector of the invention or the pharmaceutical composition of the invention is for use in the treatment of coronary heart disease or peripheral ischemia in a mammal, preferably in a human, a mouse, a rabbit, or a pig. The coronary heart disease can be an acute heart attack, myocardial ischemia, stable angina pectoris, and/or hibernating myocardium.

In one embodiment, the mammal is a human No-Option-Patient.

BRIEF DESCRIPTION OF THE DRAWINGS

Angiogenesis Induced by MRTF Activation and Translocation into the Nucleus Via CCN1 and CCN2 Activation FIG. 1*a* and FIG. 1*b* show MRTF-A transfection increased endothelial cell migration in a wound scratch assay in vitro (bordered area=uncovered area); FIG. 1*c* and FIG. 1*d*, show tubus formation of human microvascular endothelial cells (HMECs) in vitro (Ipf=low power field). Overexpression of Tβ4 showed similar effects if no MRTF shRNA was co-administered or a Tβ4 mutant (Tβ4m) lacking the G actin binding motif KLKKTET was used (scale bar: 200 μm). FIG. 1e shows how Tβ4 transfection of myocytic HL-1 cells enabled translocation of MRTF-A (green fluorescence) into the nucleus (blue fluorescence), an effect which was absent if the Tβ4m construct without the G actin binding site was used (scale bar: 20 μm). FIG. 1f shows that Tβ4 transfection of HL-1 cells induced an MRTF-SRF-sensitive luciferase reporter (comprising three copies of the SRF binding site c-fos=p3DA.Luc, see Posern et al., *Mol. Biol. Cell* 2002, 13:4167-78), in contrast to transfection with the Tβ4 mutant. FIG. 1h and FIG. 1i show Tubus maturation, evaluated as pericyte recruiting (PC, green fluorescence) on endothelial rings (EC rings, red fluorescence; scale bar: 200 μm), was induced by MRTF-A and Tβ4. Co-transfection of shRNA against the MRTF target gene CCN2 (CTGF) abolished the Tβ4 effect (mean±standard deviation, n=5, * p<0.05, ** p<0.001).

The Tβ4-MRTF-A Signaling Cascade Induces Angiogenesis In Vitro

Figure 2B:
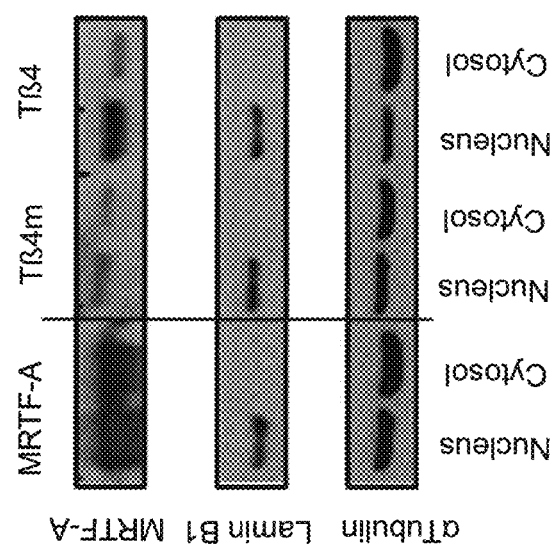
Figure 2A:
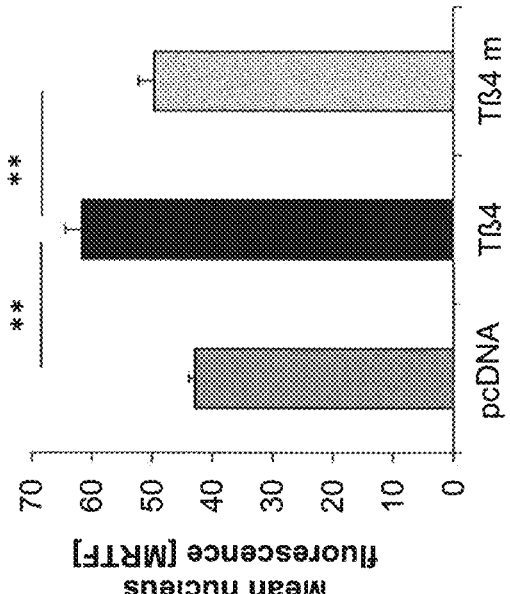
Figures 2C, 2D:
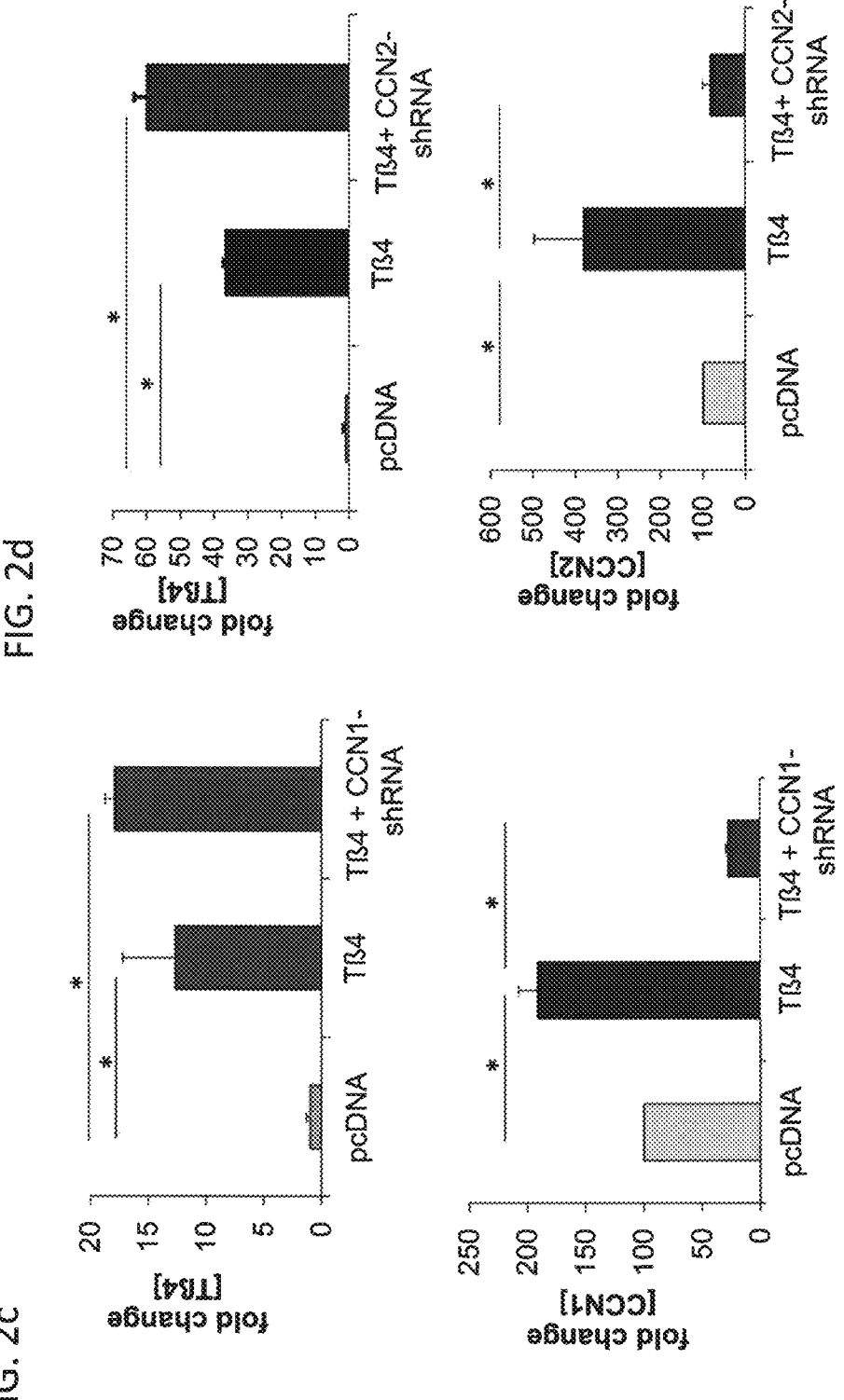
Figures 2I, 2J, 2K, 2L:
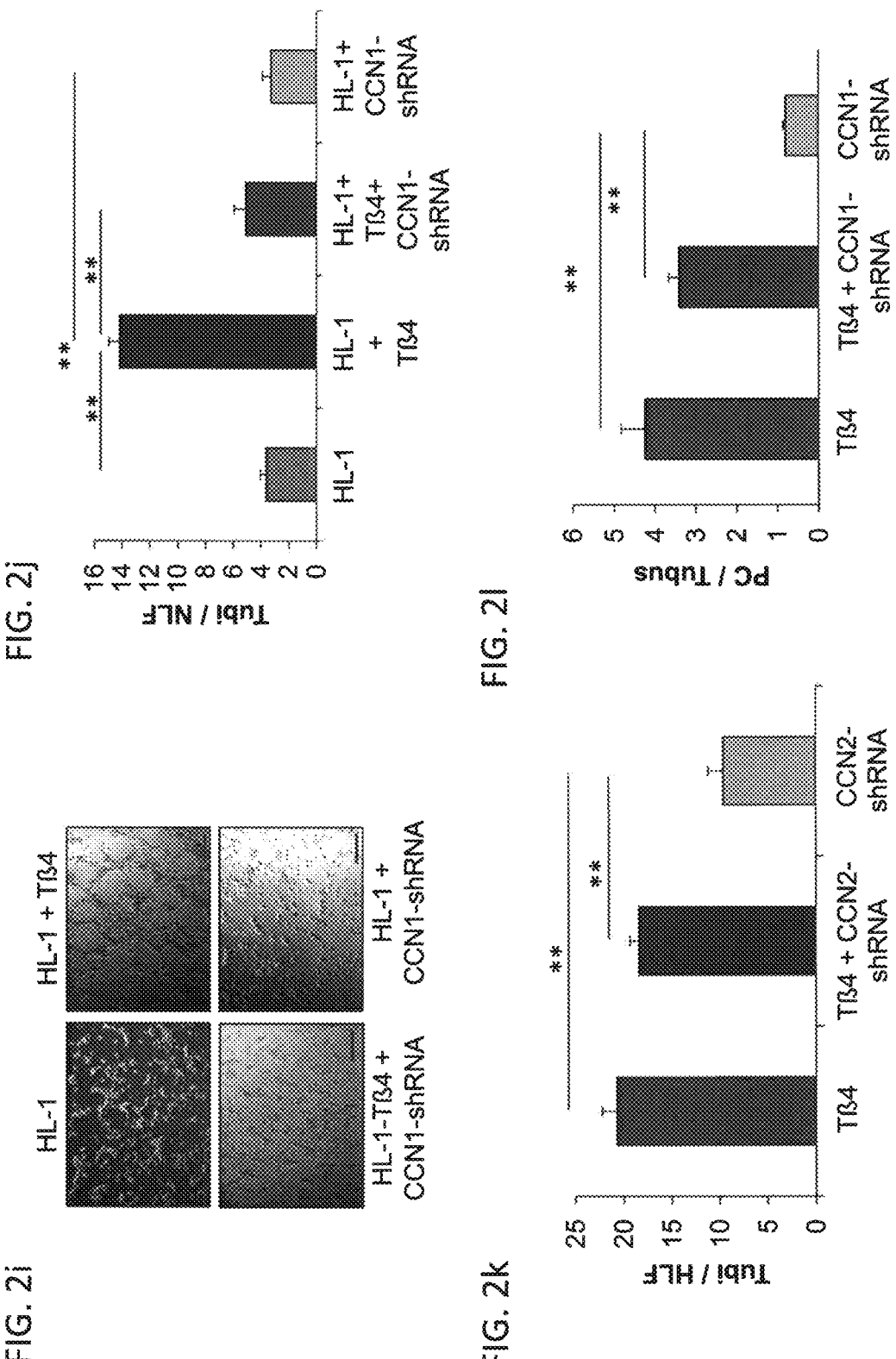

FIG. 2a shows that Tβ4 transfection of cardiomyocytic HL-1 cells enables the translocation of MRTF into the nucleus, an effect lacking when a Tβ4m construct without acting binding site was used. FIG. 2b Analysis of the MRTF-A protein level in the nucleus by Western blot showed an elevated MRTF-A protein level after Tβ4 over-expression in HL-1 cells. Tβ4m did not increase the MRTF-A level. FIG. 2c and FIG. 2d: qRT-PCR show that CCN1/2 shRNA prevented accumulation of CCN1/2 transcripts after Tβ4 expression. FIG. 2e and FIG. 2f: rAAV.Tβ4-transduced cardiomyocytic HL-1 cells induced angiogenesis (tubus formation) in endothelial cells co-cultured with HL-1 cells, if no MRTF shRNA was co-transduced, whereas rAAV.Tβ4m had no effect (scale bar: 200 μm). FIG. 2g and FIG. 2h: MRTF-A mRNA expression levels (g) and MRTF-A protein level (h) were not influenced by Tβ4 overexpression, but were significantly elevated after MRTF-A transfection. FIG. 2i, FIG. 2j: Tubus formation after Tβ4 release from rAAV.Tβ4-transduced HL-1 cells was disrupted by CCN1 shRNA (scale bar: 200 μm). FIG. 2k and FIG. 2l: Co-transfection of rAAV.Tβ4 and CCN2 shRNA did not influence Tβ4-induced tubus formation. Furthermore, CCN1 shRNA did not influence recruitment of pericyte-like cells (mean±standard deviation, n=5, * p<0.05, ** p<0.001).

Importance of MRTF Signaling for Neovascularization In Vivo

Figure 3B:
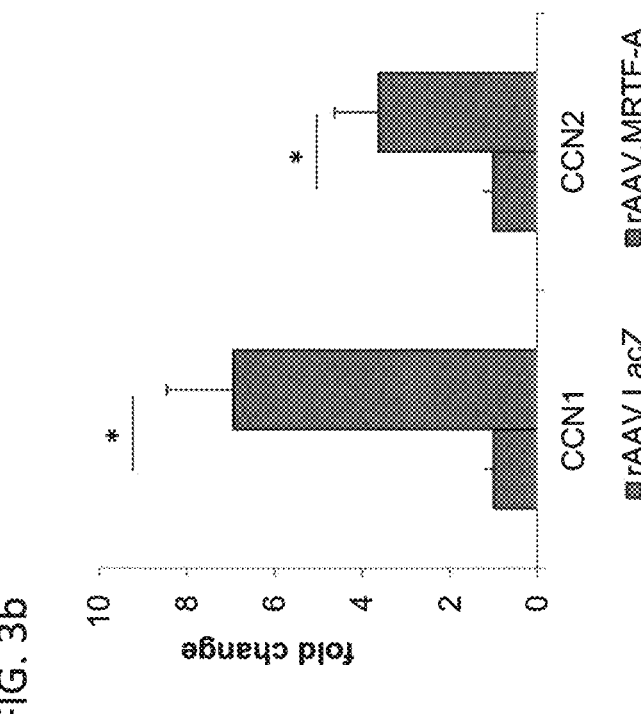
Figure 3A:
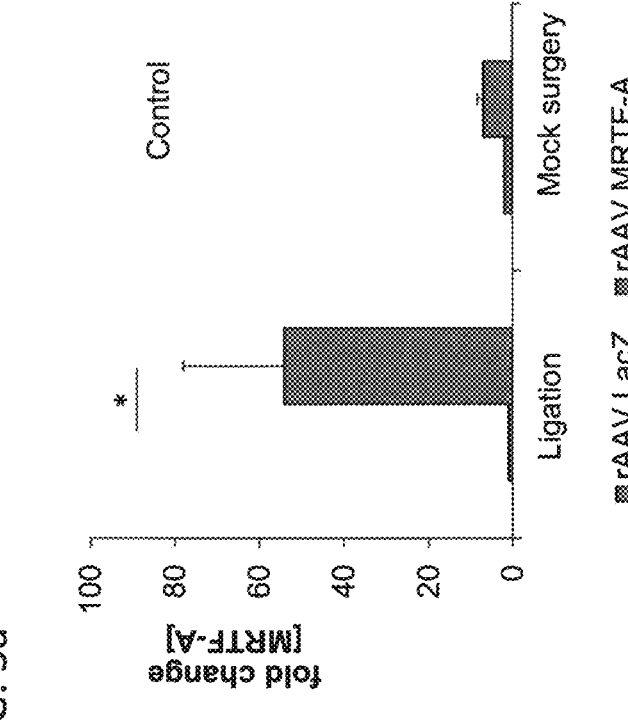
Figure 3D:
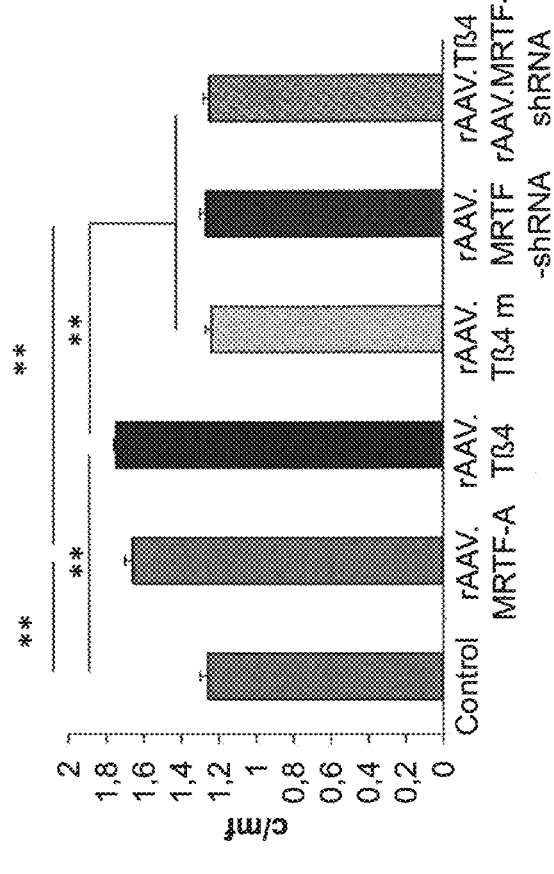
Figure 3C:
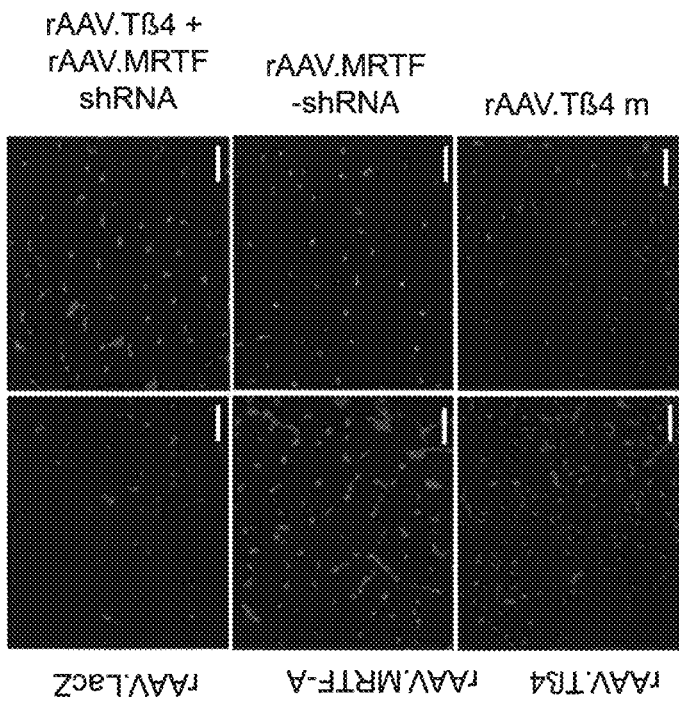
Figures 3E, 3F:
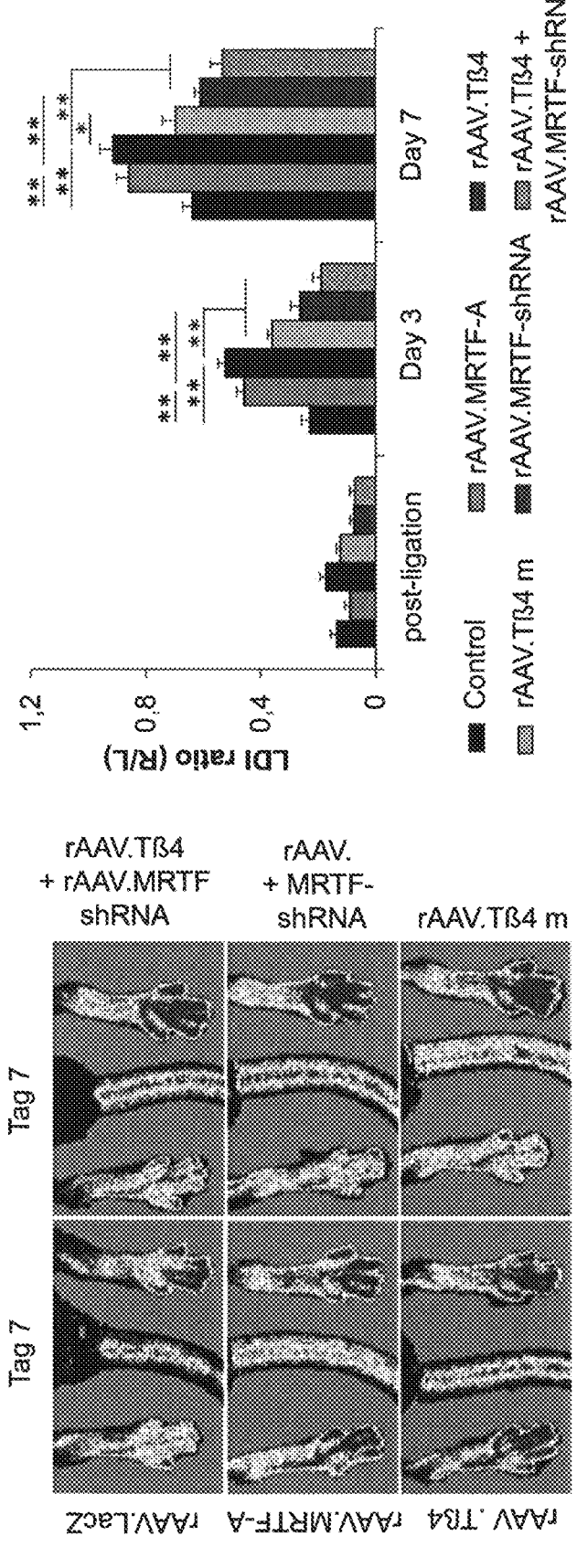
Figure 3H:
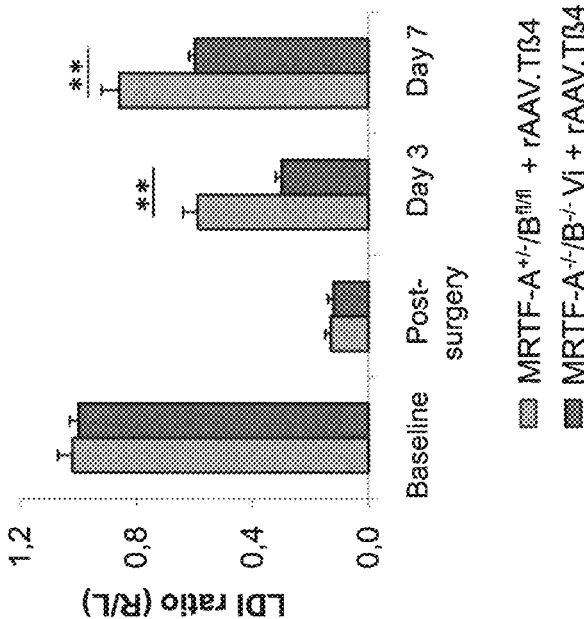
Figure 3G:
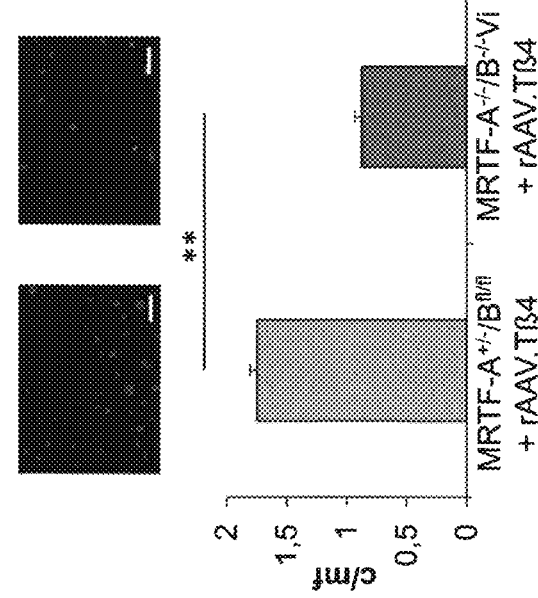

FIG. 3a qRT-PCR analysis showed an increase in MRTF-A in the ischemic hind limb transduced with rAAV.MRTF-A. FIG. 3b rAAV.MRTF-A induced MRTF/SRF target genes CCN1 and CCN2 in vivo. FIG. 3c and FIG. 3d: rAAV.MRTF-A transduction increased the capillary/muscle fiber ratio (c/mf) in a manner similar to MRTF activator Tβ4. rAAV.Tβ4m, a mutant without the G actin binding domain, or co-application of Tβ4 and rAAV.MRTF-A-shRNA, had no effect (PECAM-1 staining, scale bar 100 μm). FIG. 3e and FIG. 3f: Functionally, transduction with rAAV.MRTF-A and -Tβ4, but not rAAV.Tβ4m or rAAV.Tβ4+MRTF-shRNA, improved the perfusion of the hind limb on day 3 and day 7. FIG. 3g: After rAAV.Cre vector-induced MRTF-B deletion in MRTF-A-deficient mice (Mrtfa$^{-/-}$/b$^{flox/flox}$+rAAV.Cre=MRTF-A/B$^{-/-}$ Vi), Tβ4 transduction could not induce angiogenesis, in contrast to Mrtfa$^{+/-}$/b$^{flox/flox}$ mice (=MRTF-A/B$^{+/-}$). FIG. 3h Perfusion increased by rAAV.Tβ4 was suppressed in MRTF-A/B$^{-/-}$Vi mice. FIG. 3i and FIG. 3j In CCN1$^{-/-}$Vi mice (=CCN1$^{flox/flox}$+rAAV.Cre), both the increase of the capillary/muscle fiber ratio (PECAM-1 staining, scale bar 100 μm) and the increase of hind limb perfusion shown in FIG. 3k and FIG. 3l were suppressed (mean±standard deviation, n=5, * p<0.05, ** p<0.001).

MRTF-A Induced Vessel Growth in Mouse Hind Limb Ischemia

Figure 4A:
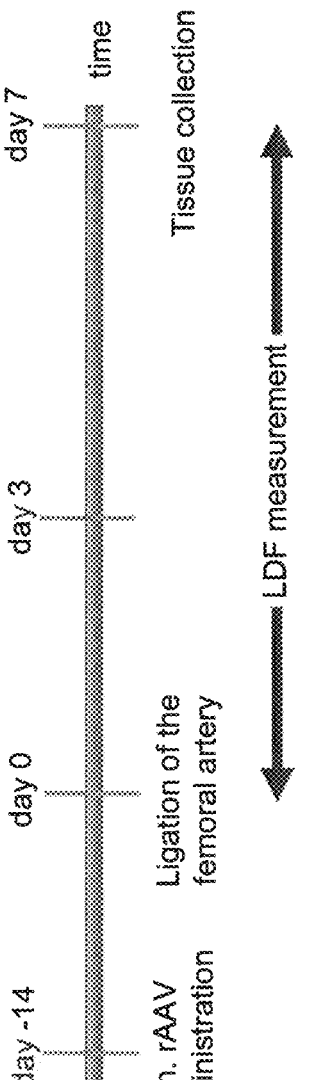
Figure 4D:
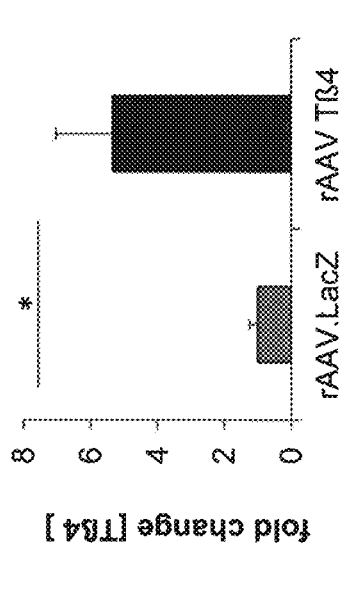
Figure 4E:
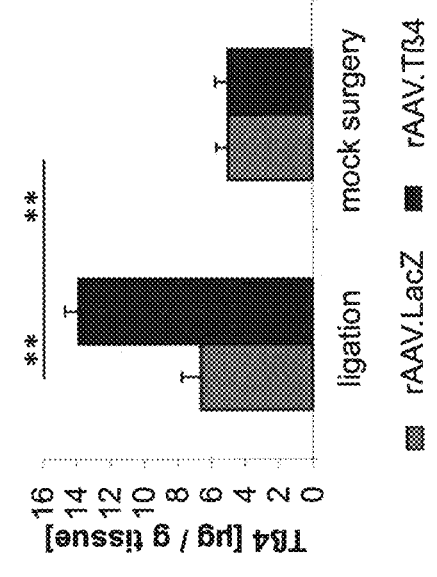
Figure 4B:
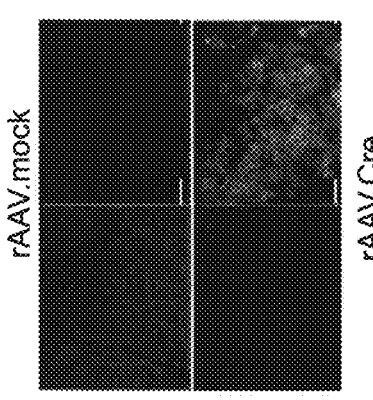
Figure 4C:
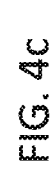
Figure 4C:
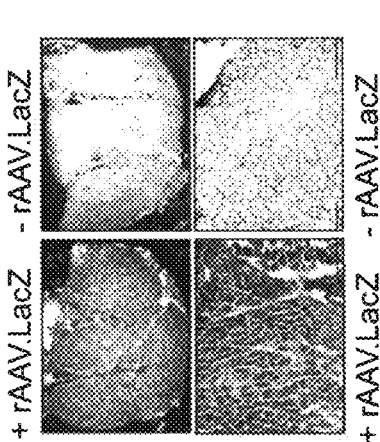

FIG. 4a Protocol for mouse hind limb ischemia. Intra-muscular (i.m.) rAAV administration was performed on day −14 and the femoral artery was ligated on day 0. Subsequent laser Doppler flowthrough measurements (LDF) were per-formed on days 0, 3, and 7. FIG. 4b: i.m. injection of rAAV.Cre induced homogenous muscle transduction, shown by a change of Tomato fluorescence (red) to GFP fluores-cence (green) in Tomato reporter gene mice. FIG. 4c: i.m. injection of rAAV.LacZ ($3 \times 10^{12}$ virus particles) led to a homogenous transduction (blue staining) of the targeted hind limb, but not of the opposite one. FIG. 4d qRT-PCR detection of Tβ4 in the rAAV.Tβ4-transduced ischemic hind limbs, but not in the rAAV.LacZ-transduced hind limbs. FIG. 4e: HPLC analysis showed an increase of Tβ4 protein concentration in the rAAV.Tβ4-transduced ischemic hind limbs. FIG. 4f: rAAV.Tβ4 induced MRTF target genes CCN1 and CCN2 in vivo. FIG. 4g: Tβ4-induced maturation of capillaries (pericyte investment, NG2 staining) was sup-pressed in MRTF-A/B$^{-/-}$Vi hind limbs. FIG. 4h and FIG. 4i In both MRTF-A$^{-/-}$/B$^{flox/flox}$ mice (MRTF-A knockout) and MRTF-A$^{+/-}$/B$^{-/-}$Vi mice (MRTF-B knockout) rAAV.Tβ4 transduction induced an increase of capillary density (h) and perfusion (i). However, the rAAV.Tβ4 effect was largest in wild type mice (MRTF-A$^{+/-}$/B$^{flox/flox}$). Furthermore, there was no significant difference between MRTF-A and MRTF-B knockout mice (mean±standard deviation, n=4, * p<0.05 vs. control).

Figures 5A, 5B:
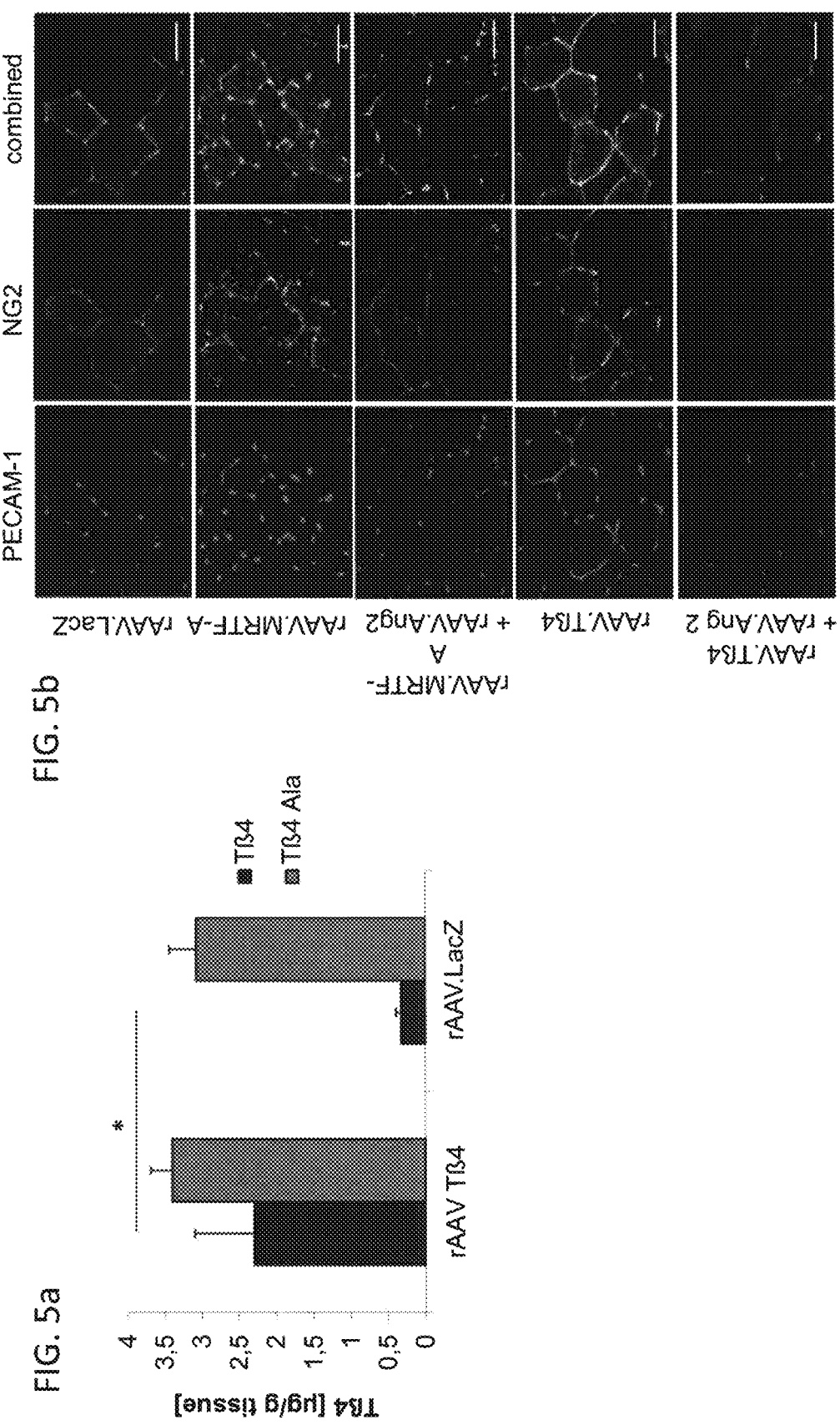
FIG. 5g Tβ4-induced tubus formation was abolished in the case of shRNA co-transfection of the MRTF-SRF target gene CCN1 (Cyr61) (scale bar: 200 μm).
Figures 5C, 5D, 5E:
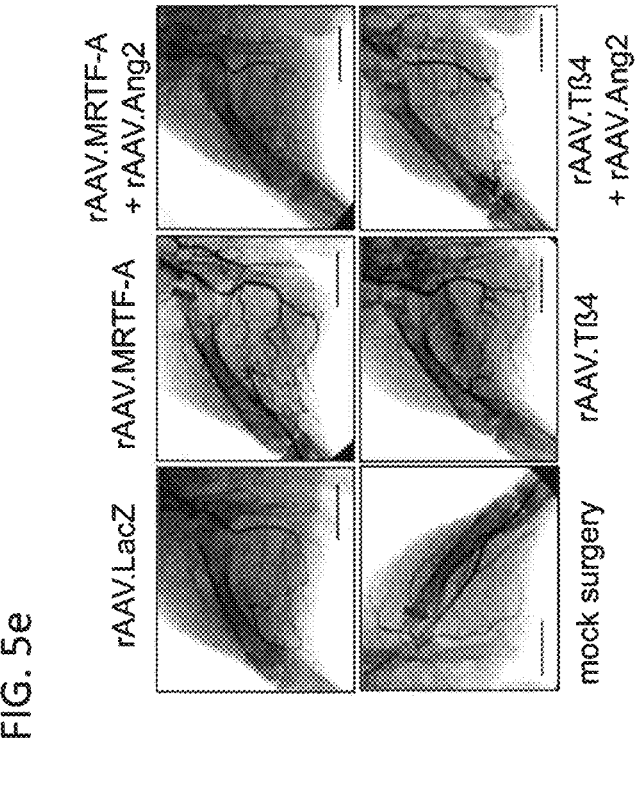
Figure 5G:
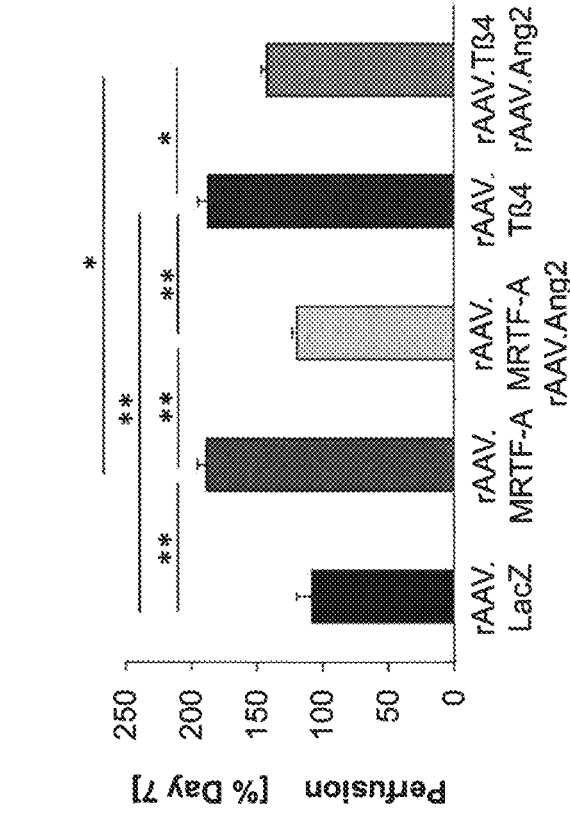
Figure 5F:
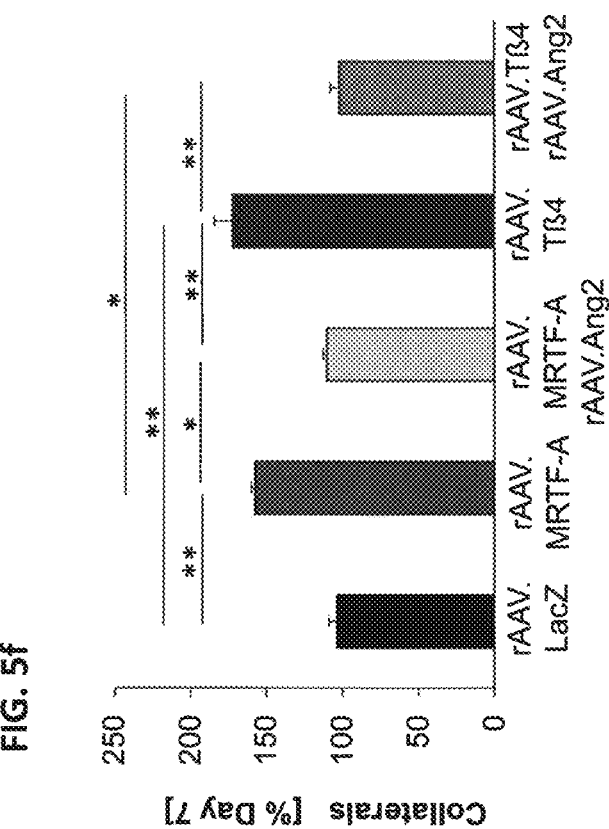

Tβ4/MRTF-A-Induced Microvessel Maturation: Essential Role for Collateral Growth and Improved Perfusion FIG. 5a: HPLC analysis showed a significant increase of Tβ4 protein after rAAV.Tβ4 transduction of ischemic rabbit hind limbs, whereas rabbit-specific Tβ4-Ala remained unchanged. FIG. 5b, FIG. 5c and FIG. 5d: rAAV.MRTF-A or rAAV.Tβ4 administration increased capillary density (PE-CAM-1 staining) and pericyte investment (NG2 staining, scale bar: 50 μm), both of which were abolished by co-application of angiopoietin 2 (rAAV.Ang2). FIG. 5e and FIG. 5f: Angiographies of ischemic hind limbs on day 35 showed an increased collateral formation in rAAV.MRTF-A- and rAAV.Tβ4-treated animals (arrows show site of excision of the femoral artery). Co-application of rAAV.Ang2 abol-ished this effect. FIG. 5g rAAV.MRTF-A and rAAV.Tβ4 induced an increase of perfusion in ischemic hind limbs, unless rAAV.Ang2 or L-NAME, which inhibits nitrogen oxide formation, were co-applied (mean±standard deviation, n=5, * p<0.05, ** p<0.001).

Tβ4-MRTF-A-Induced Vessel Growth in Rabbits

Figures 6B, 6C, 6D:
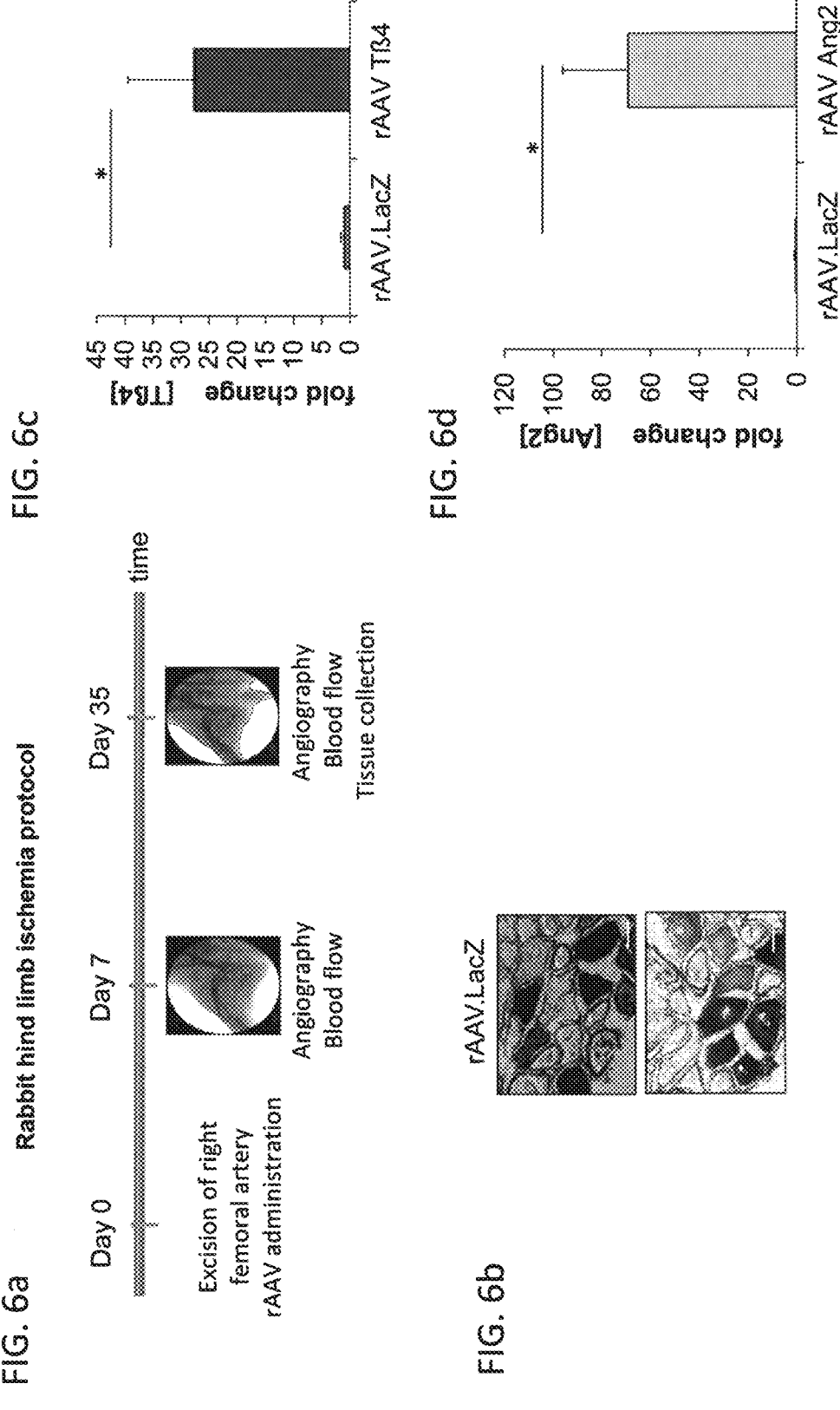
Figures 6E, 6F, 6G, 6H:
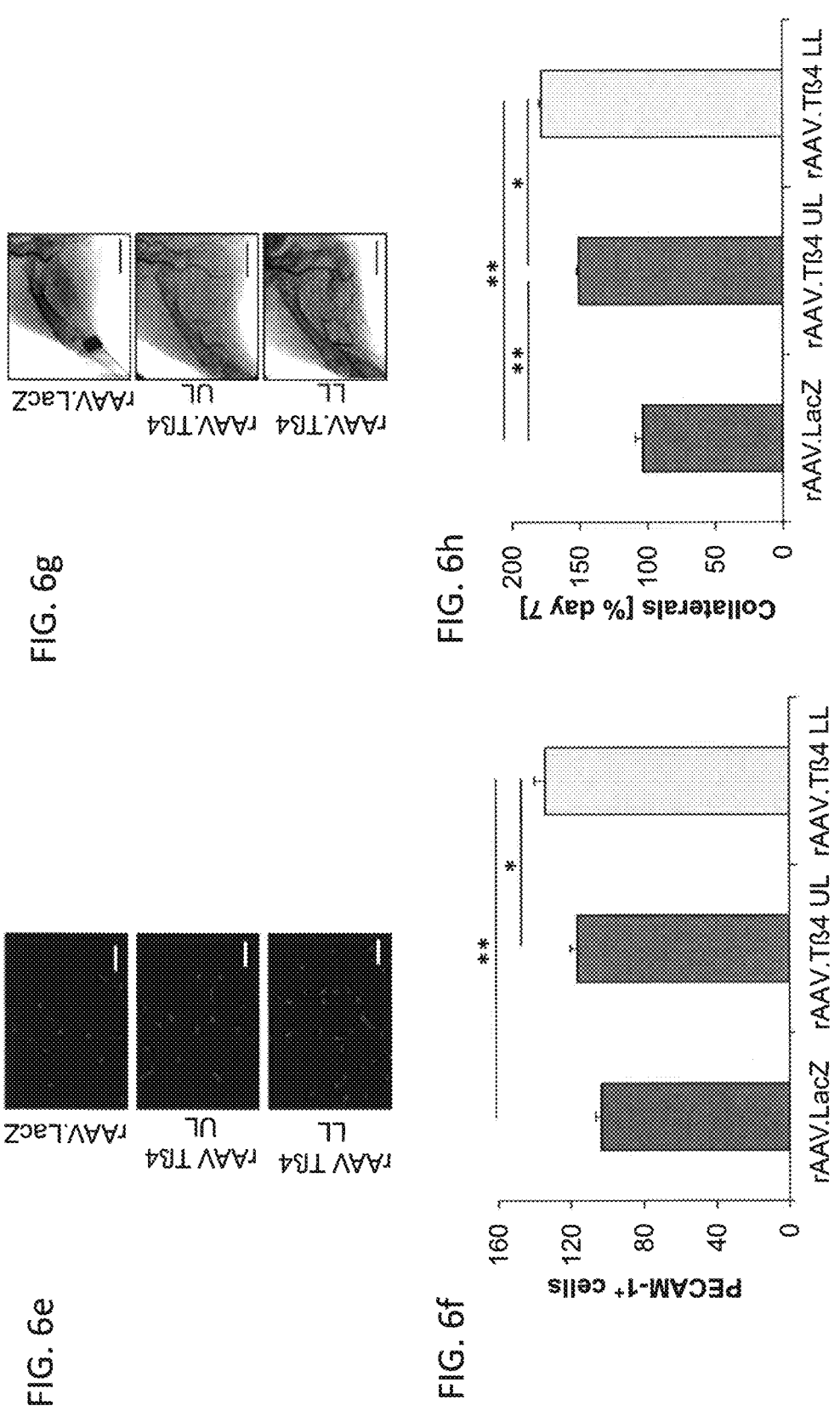

FIG. 6a: Protocol of a model for rabbit hind limb ischemia (femoral artery excision). FIG. 6b: @-galactosidase staining 5 weeks after i.m. injection of rAAV.LacZ into the rabbit hind limb. FIG. 6c and FIG. 6d: qRT-PCR of Tβ4 (c) and angiopoietin 2 (d), normalized to GAPDH, in control and treated animals (n=3). FIG. 6e and FIG. 6f Tβ4 overexpres-sion only in the lower limb (rAAV.Tβ4 LL) increased capillary density (PECAM-1 staining) in the lower limb, whereas Tβ4 transduction only in the upper limb (rAAV.Tβ4 UL) did not influence the capillarization in the lower limb (scale bar: 50 μm). FIG. 6g and FIG. 6h: Collateralization was increased in the rAAV.Tβ4 UL group, and to an even greater extent in the rAAV.Tβ4 LL group, whereas perfusion FIG. 6i was increased only in the rAAV.Tβ4 LL group and not in the rAAV.Tβ4 UL group. FIG. 6*j* Compared to rAAV.Tβ4-transduced rabbits, the co-administration of L-NAME did not decrease the NG2/PECAM-1 ratio, indicating robust and balanced microvessel growth. In contrast, L-NAME or rAAV.Ang2 treatment alone was not able to increase the NG2/PECAM-1 ratio as strongly as rAAV.Tβ4. FIG. 6*k* and FIG. 6*l*: Tβ4-dependent increase of collateralization and perfusion was significantly reduced if L-NAME was co-administered (mean±standard deviation, n=5, ** p<0.01).

Figures 7D, 7E, 7F:
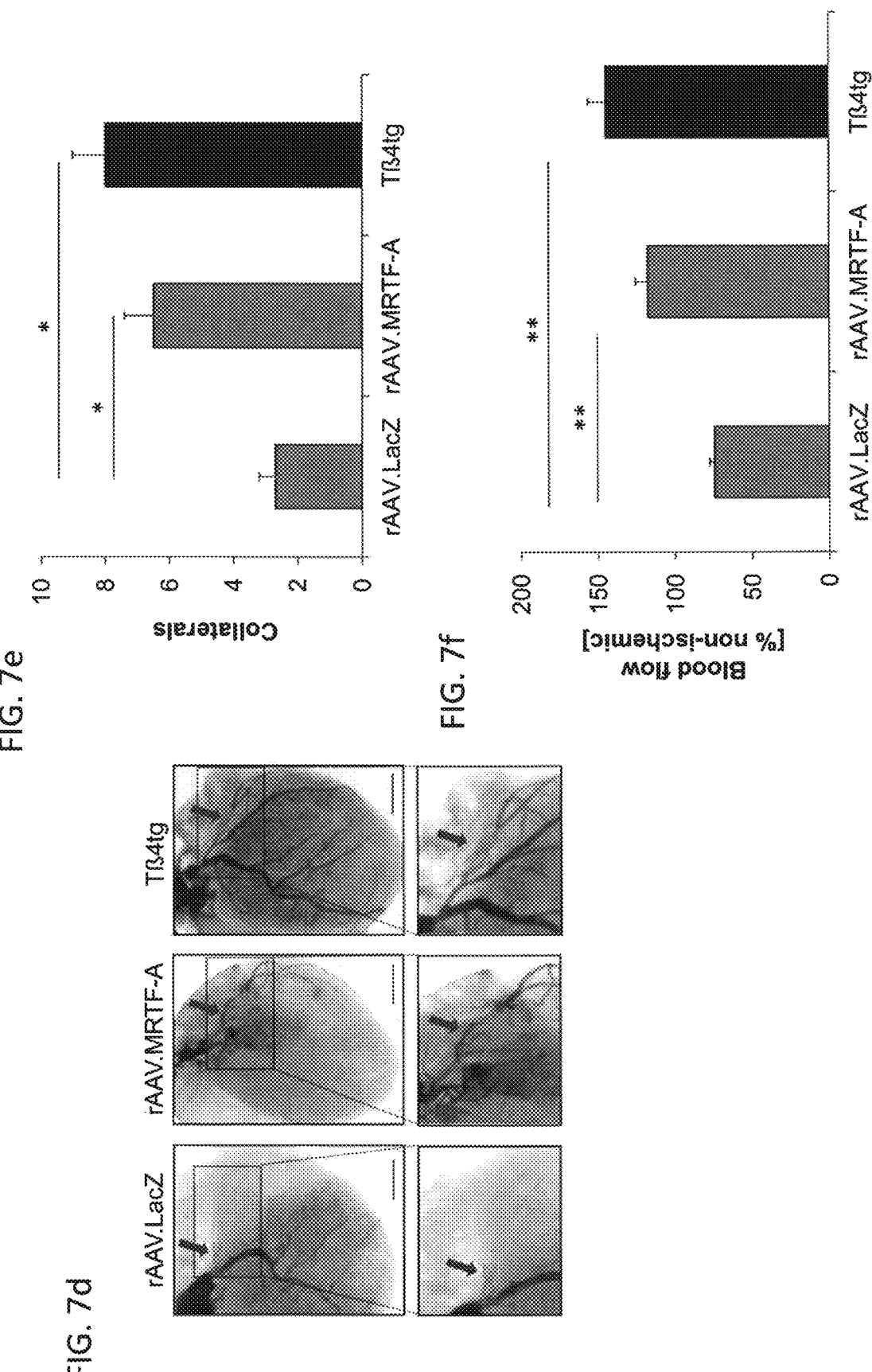
Figure 7H:
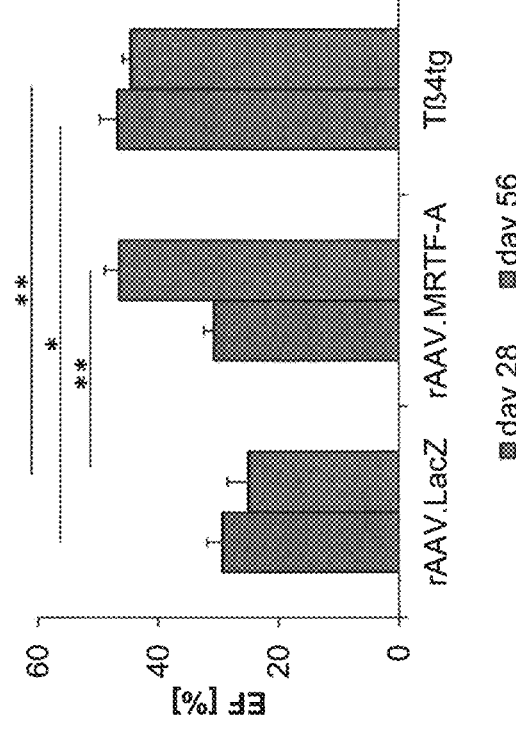
Figure 7G:
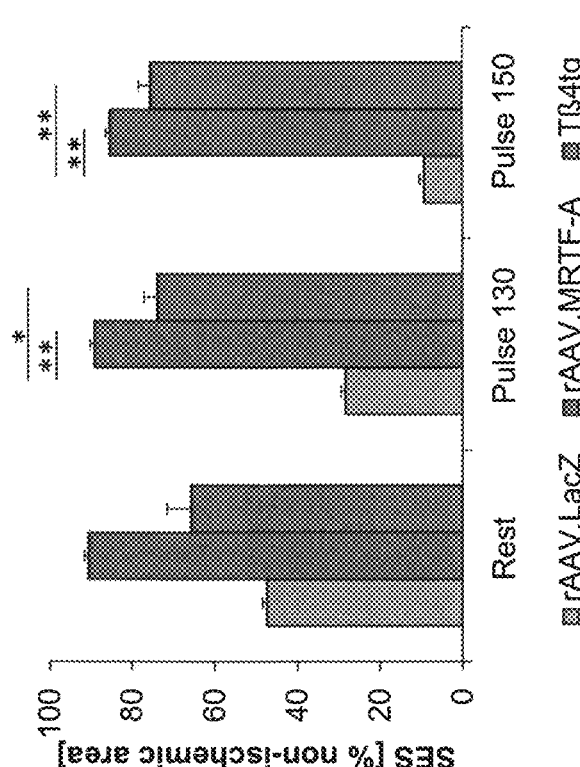
Figure 7J:
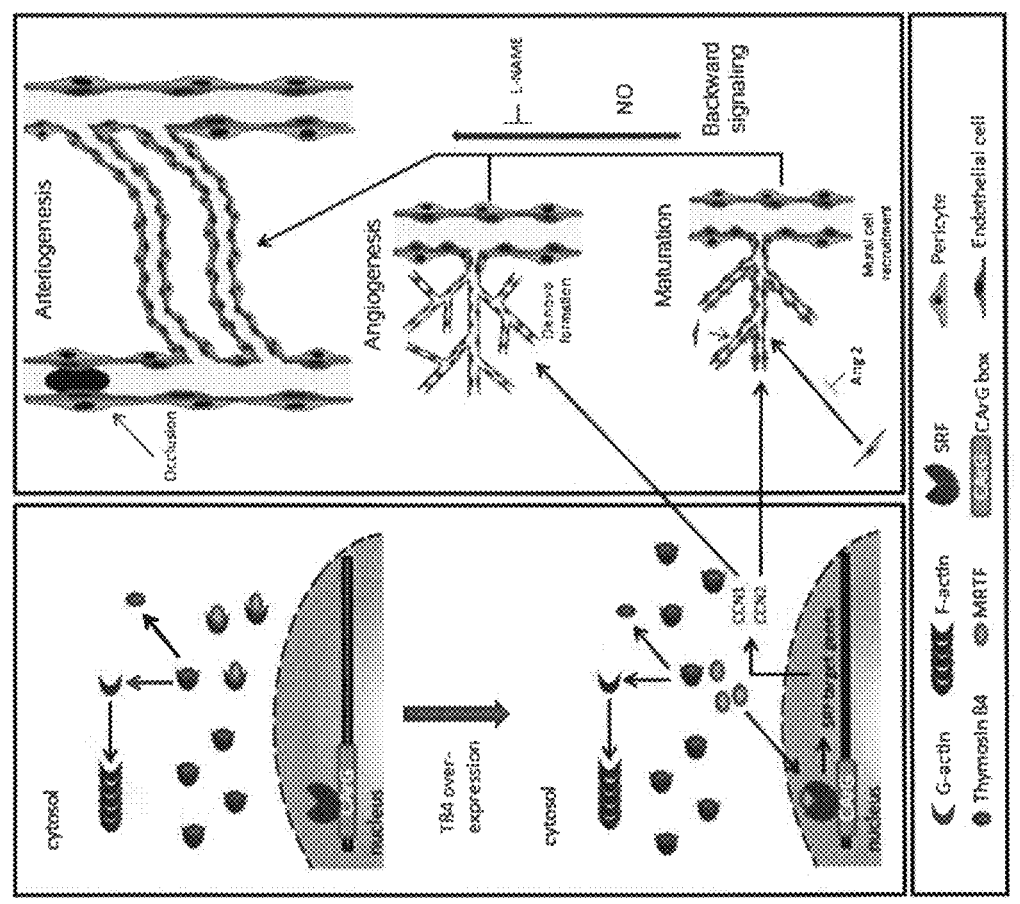

MRTF-A Improves Collateral Formation and Perfusion in Hibernating Myocardium of Pigs FIG. 7*a*-FIG. 7*c*: In hibernating pig myocardium (see FIG. 8*a*), rAAV.MRTF-A transduction and ubiquitous overexpression of Tβ4 (Tβ4tg, see FIG. 9) induced capillary sprouting (PECAM-1 staining, scale bar: 50 μm) and pericyte investment (NG2 staining). FIG. 7*d* and FIG. 7*e*: Moreover, collateral growth was detected in rAAV.MRTF-A-transduced hearts, similarly to Tβ4tg hearts. FIG. 7*f*: The regional flow reserve, obtained by fast atrial stimulation (130 beats per minute), was increased in rAAV-MRTF-A-transduced and Tβ4-transgenic hearts. FIG. 7*g* Regional myocardium function, measured by subendocardial segment shortening at rest and under atrial stimulation (130 and 150 beats per minute), showed improved functional reserve either by rAAV.MRTF-A transduction or in Tβ4tg hearts. FIG. 7*h*: The ejection fraction, a parameter of global myocardium function, was improved in rAAV.MRTF-A-transduced animals on day 56, compared with day 28. Constitutively overexpressing animals (Tβ4tg), however, showed no loss of function on day 28. FIG. 7*i*: Mechanisms of MRTF-mediated therapeutic neovascularization: MRTF-A or Tβ4 transduction induces an increased amount of MRTF-A not bound to G actin that interacts with SRF upon translocation into the nucleus and induces e.g., CCN1 and CCN2 as target genes. CCN1 enables capillary growth (angiogenesis), whereas CCN2 increases pericyte investment (vascular maturation). Together, these mechanisms induce collateral growth in a nitrogen oxide-dependent manner, leading to therapeutic neovascularization (mean±standard deviation, n=5, * p<0.05, ** p<0.001).

Functional Efficiency of the Tβ4-MRTF-A Axis in Chronically Ischemic Pig Hearts

Figures 8A, 8B:
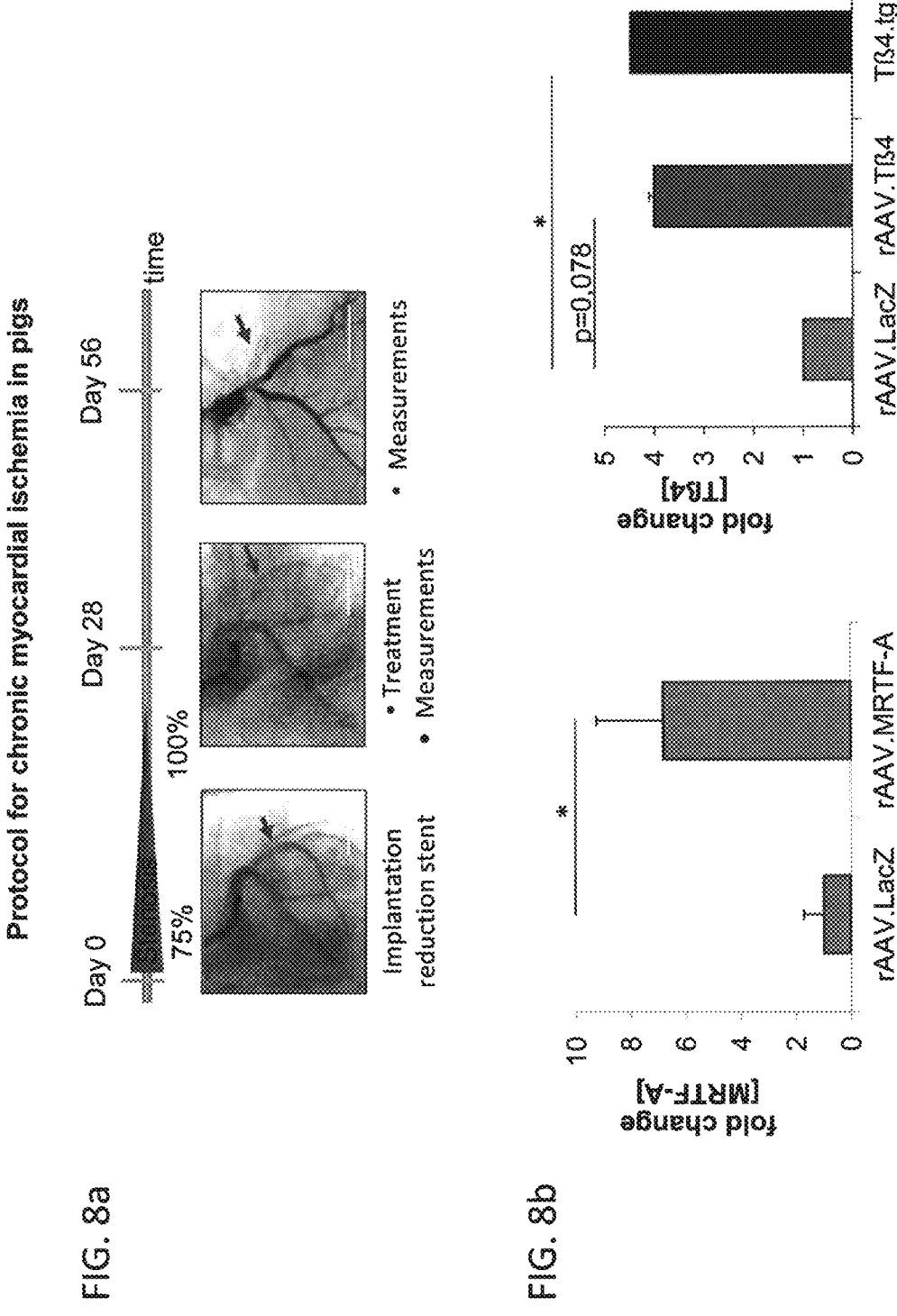

FIG. 8*a*: Protocol of the pig model for hibernating myocardium. FIG. 8*b*: RT-PCR-detection of MRTF-A and Tβ4 in control pigs compared with rAAV.Tβ4 and Tβ4-transgenic (Tβ4tg) pig hearts. FIG. 8*c*: Examples of LacZ staining (blue) after rAAV.LacZ retroinfusion ($5×10^{12}$ virus particles) into the pig heart. FIG. 8*d*: Before treatment (on day 28), retention analysis of fluorescent microbeads at rest showed a reduced blood flow in the ischemic area of rAAV.LacZ und rAAV.MRTF-A hearts, but not of Tβ4tg hearts, similarly to the flow reserve FIG. 8*e*: at fast heart rate (130 bpm). FIG. 8*f*: 4 weeks after treatment (on day 56), the regional myocardial blood flow in rAAV.MRTF-A und Tβ4tg animals improved. FIG. 8*g*: Furthermore, the Rentrop score showed an increased collateralization on day 56 in rAAV.MRTF-A-transduced or Tβ4tg hearts. FIG. 8*h*: Examples of MRT analysis on day 56 for control (left) and rAAV.MRTF-A-treated pig hearts. FIG. 8*i*: The left ventricular end-diastolic pressure (LVEDP) increased in ischemic hearts from day 28 to day 56 if MRTF-A was not overexpressed. Tβ4tg constitutively overexpressing Tβ4 showed no change from day 28 to day 56 (mean±standard deviation, n=5, * p<0.05, ** p<0.001).

Production of Tβ4-Transgenic Pigs

Figure 9:
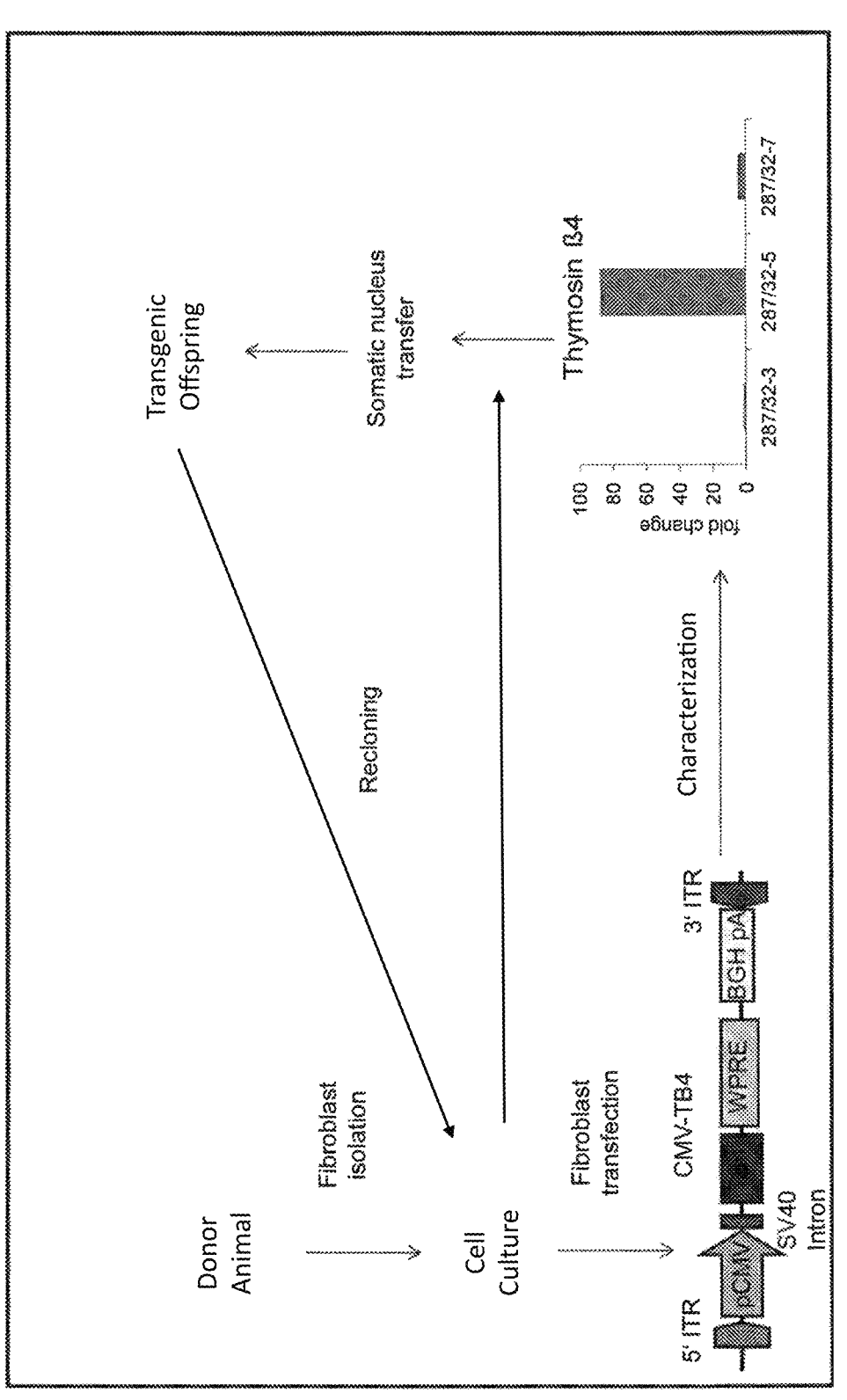

FIG. 9 provides a schematic for the production of TB4-transgenic pigs. Fibroblasts of donor pigs were isolated and cultured. pCMV-Tβ4 was transfected by electroporation and the cells were cultured for 14 days. After detection of stable transfection of Tβ4, a somatic nuclear transfer into pig oocytes was performed. Offspring were analyzed for Tβ4 expression and fibroblasts of Tβ4-expressing animals were cultured and subsequently used for a second somatic nuclear transfer. After genotyping, animals of this generation were used for the pig model of chronic ischemia.

MRTFs are Necessary for Tβ4-Induced Cardioprotection

Figures 10A, 10B, 10C:
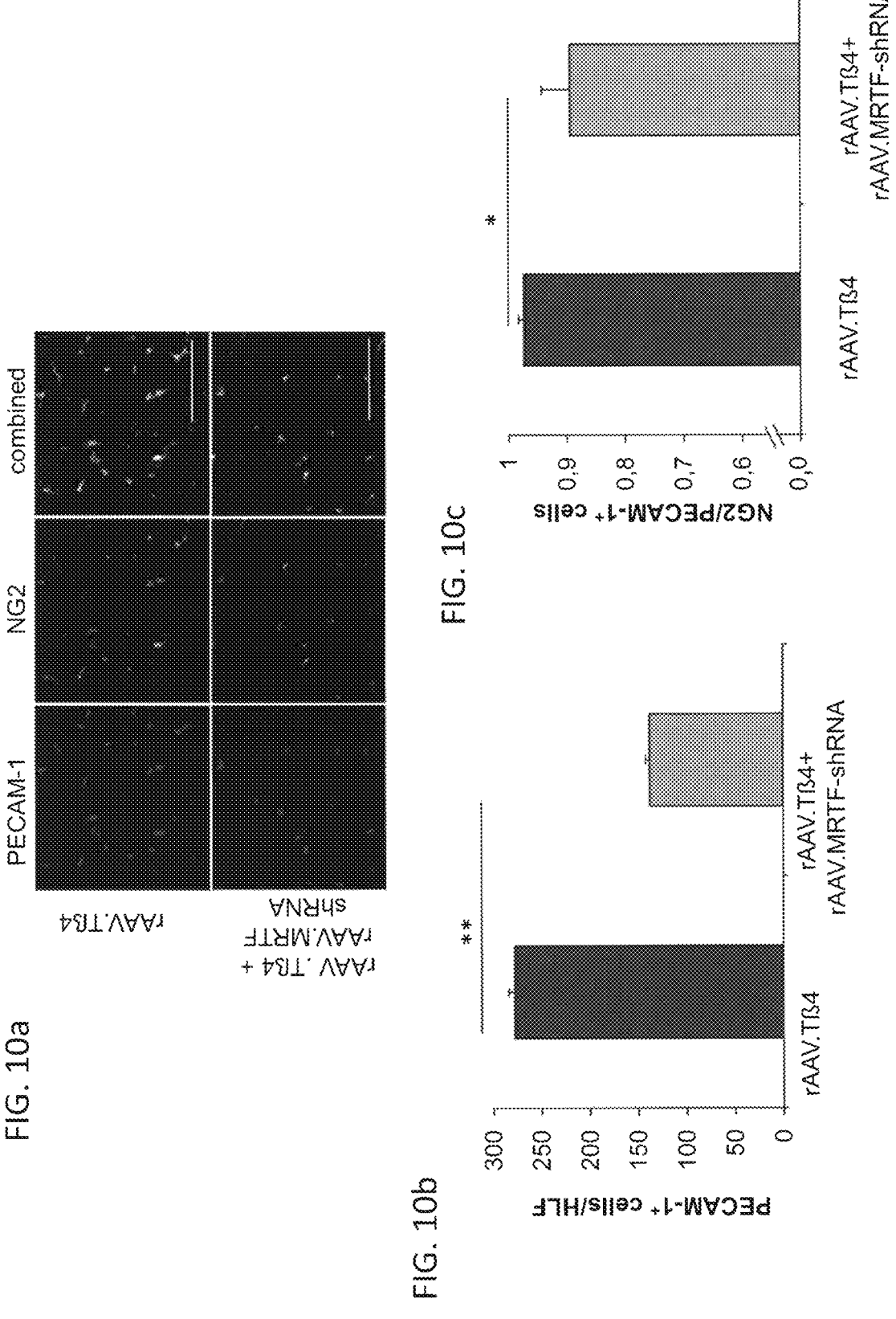
Figures 10G, 10H, 10I, 10J:
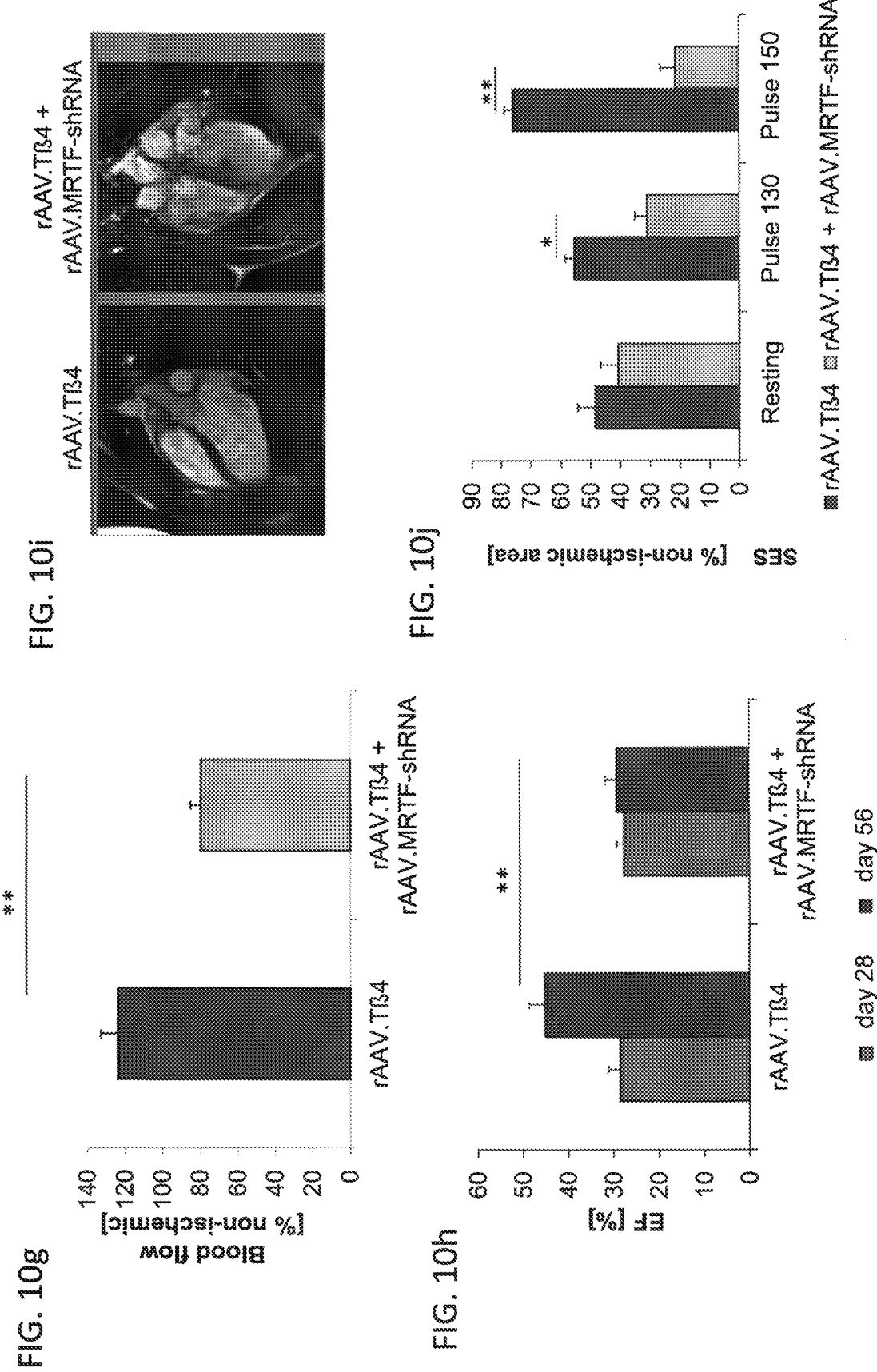

FIG. 10*a* and FIG. 10*b*: rAAV.Tβ4 induced capillary growth (PECAM-1 staining) and FIG. 10*c* pericyte investment (NG2 staining, scale bar 50 μm), unless co-administration of rAAV.MRTF-shRNA prevented both processes. FIG. 10*d* and FIG. 10*e*: Collateral growth was detected in rAAV.Tβ4-transduced animals, but not after co-administration of rAAV.MRTF-shRNA. FIG. 10*f*: Rentrop scores showed increased collateralization after rAAV.Tβ4 transduction, except in the case of co-administration of MRTF-A shRNA. FIG. 10*g*: Regional myocardial blood flow at flow reserve (atrial stimulation 130/min) improved in rAAV.Tβ4-treated animals, but not in rAAV.Tβ4+MRTF-shRNA hearts. FIG. 10*h*: Analysis of the ejection fraction showed improved systolic myocardium function in rAAV.Tβ4-transduced animals (day 56), as compared with day 28 (day of transduction). No improvement of the ejection fraction was observed in rAAV.Tβ4+MRTF-shRNA-treated hearts. FIG. 10*i*: MRT images of rAAV.Tβ4-transduced hearts without (left) or with (right) rAAV.MRTF-shRNA co-administration. FIG. 10*j*: Regional myocardium function, measured by subendocardial segment shortening at rest and at atrial stimulation (130 and 150 bpm) shows increased functional reserve after rAAV.Tβ4 but not rAAV.Tβ4+MRTF-shRNA transduction (mean±standard deviation, n=5, * p<0.05, ** p<0.001).

Production and Cardial Phenotyping of INS$^{C94Y}$-Transgenic Pigs (Diabetes Mellitus Type 1)

Figure 11A:
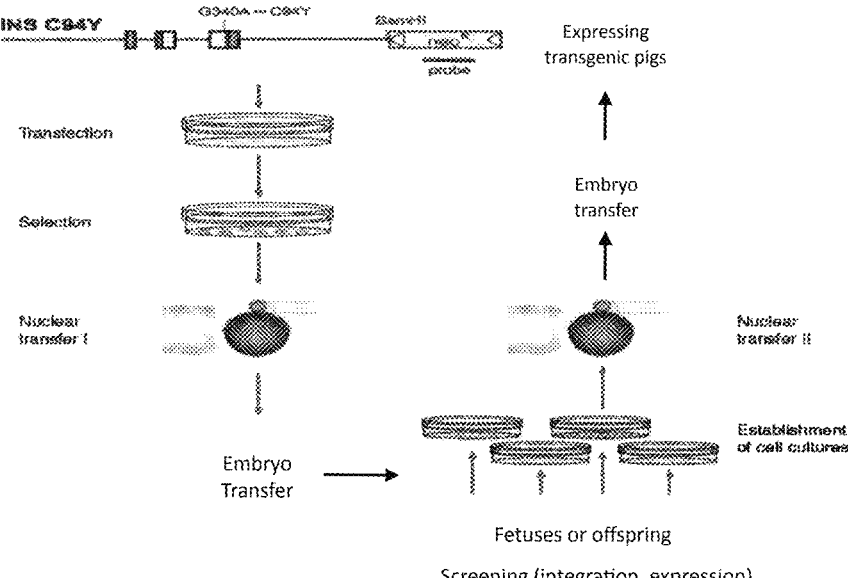
Figure 11A:
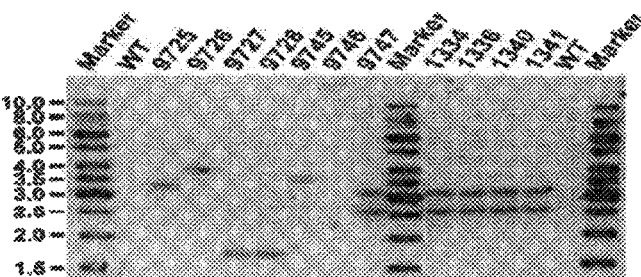

FIG. 11*a*: Process of producing the INS$^{C94Y}$-transgenic pigs. FIG. 11*b*: Blood glucose levels of wild type and diabetic pigs. FIG. 11*c*: Fluorescence staining of endothelial cells (PECAM-1-positive cells, red) and pericytes (NG-2-positive cells, green). FIG. 11*d*: Number of endothelial cells in the myocardium of wild type and diabetic pigs. FIG. 11*e*: Left ventricular end-diastolic pressure in animals with diabetes mellitus type I and wild type animals.

Figure 12A:
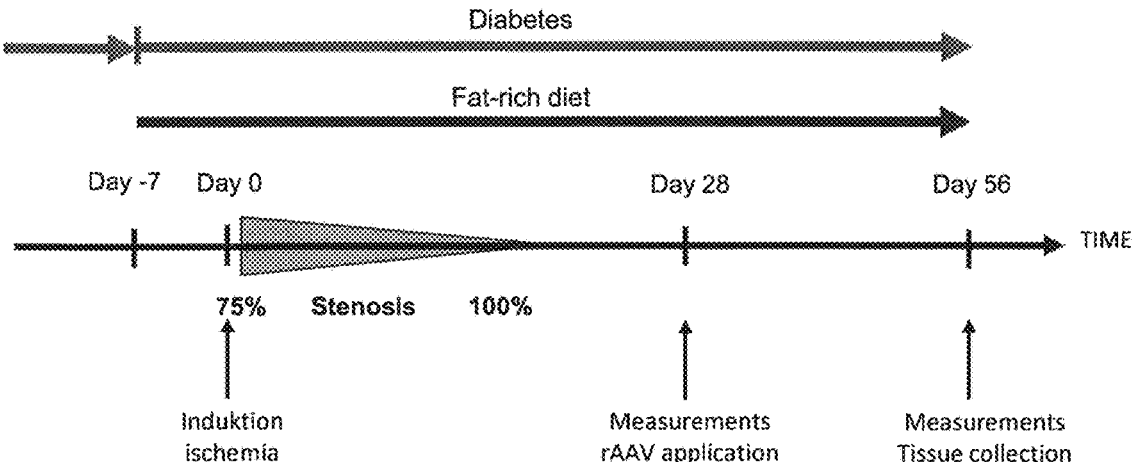
Figure 12B:
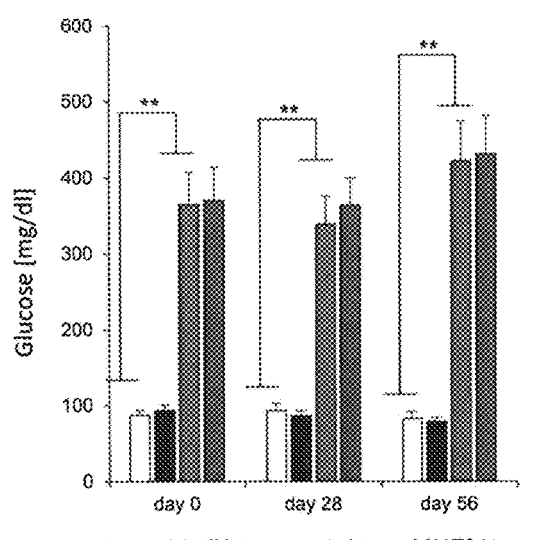
Figure 12C:
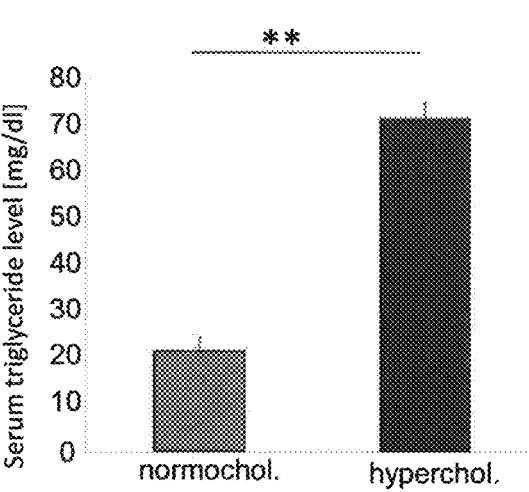
Figure 12D:
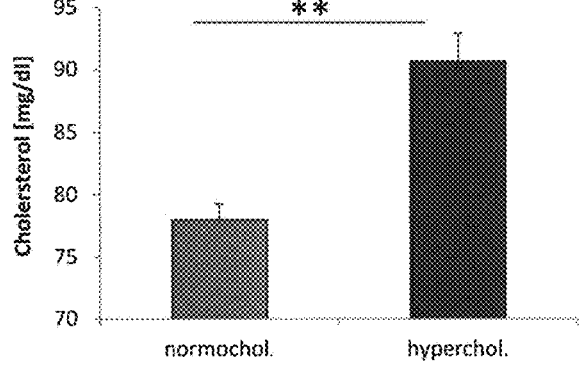

Characterization of the Chronically Ischemic Myocardium Model with Cardiovascular Risk Factors FIG. 12*a*: Protocol of the pig model for hibernating myocardium with diabetes mellitus type I or hypercholesterolemia. FIG. 12*b*: Blood glucose concentration of the specific groups of animals over the duration of the experiment: control wild type; wild type treated with rAAV.Tβ4; control with diabetes; diabetes treated with rAAV.Tβ4. FIG. 12*c* and FIG. 12*d*: Serum trigylceride and cholesterol levels in animals with hypercholesterolemia (fat rich diet) and normal diet.

Influence of rAAV.Tβ4 Application on Angio- and Arteriogenesis in Animals with Diabetes Mellitus Type 1

Figure 13A:
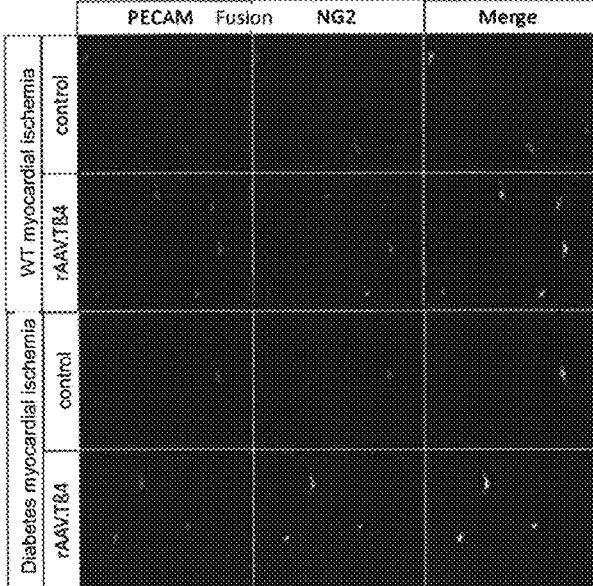
Figure 13B:
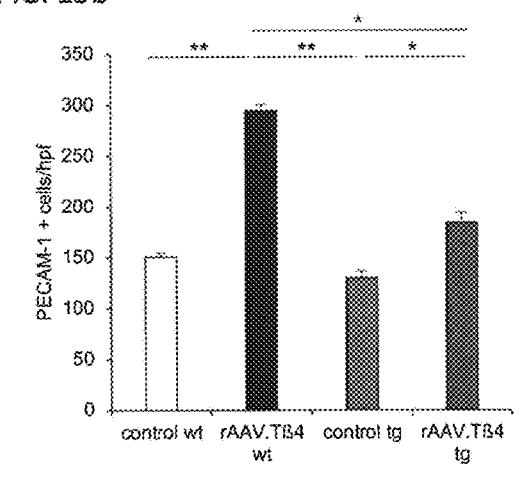
Figure 13C:
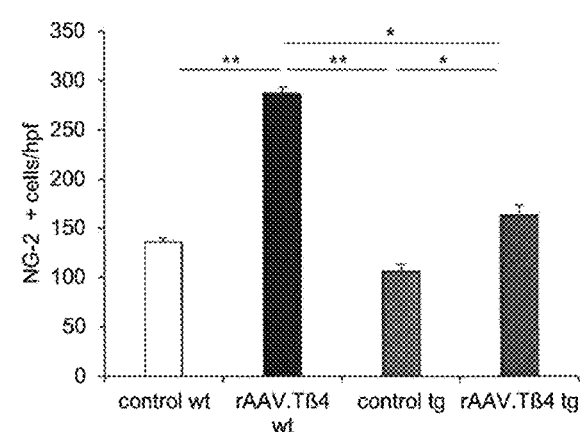
Figure 13D:
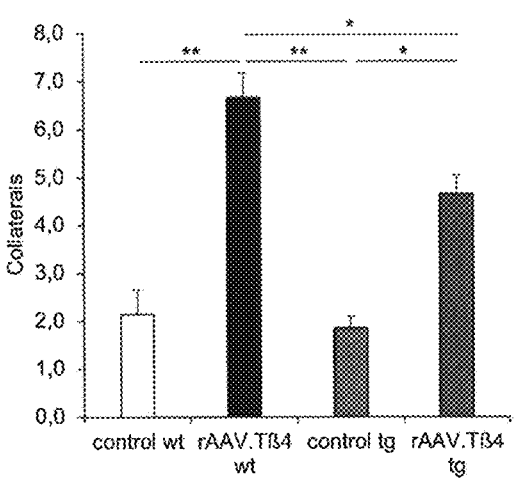
Figure 13E:
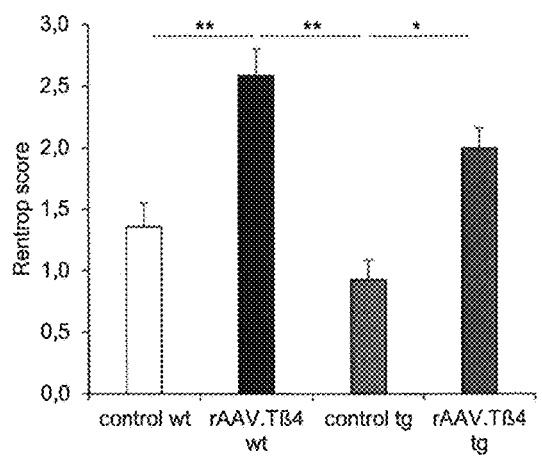

FIG. 13*a*: Fluorescence staining of endothelial cells (PECAM-1-positive cells, red) and pericytes (NG-2-positive cells, green) in hibernating pig myocardium of diabetic and wild type animals. FIG. 13*b* and FIG. 13*c*: Number of endothelial cells and pericytes. FIG. 13*d*: Number of collaterals formed. FIG. 13*e*: Rentrop score.

Figure 14A:
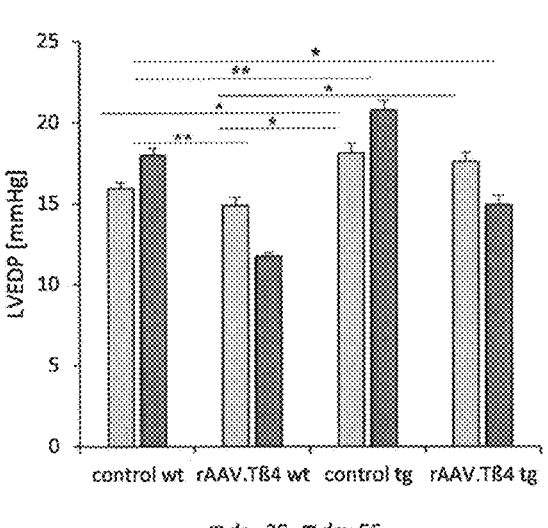
Figure 14B:
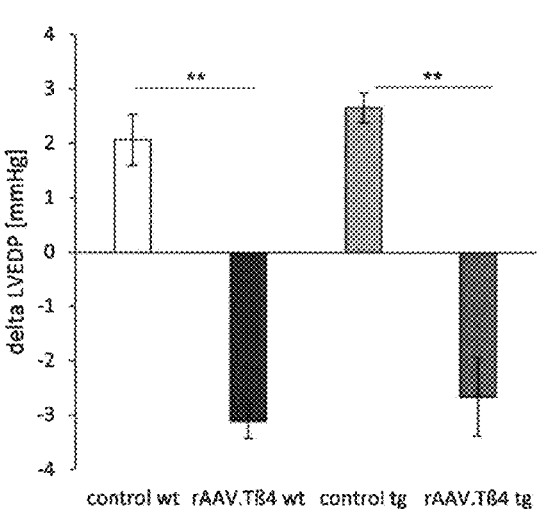
Figure 14C:
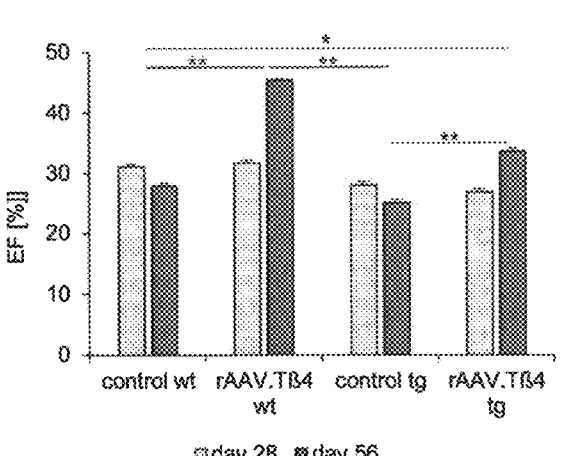
Figure 14D:
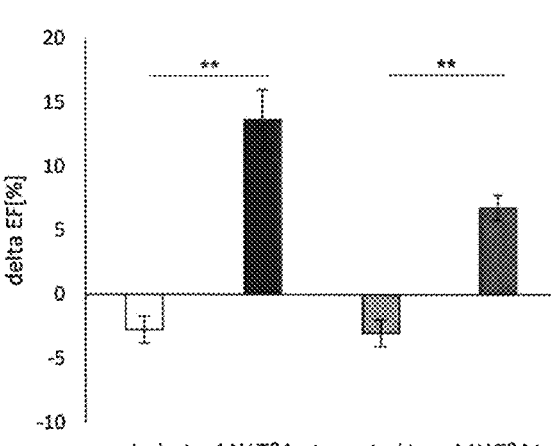

Functional Efficiency of rAAV.Tβ4 Application in Animals with Diabetes Mellitus Type I FIG. 14a and FIG. 14b: Left ventricular end-diastolic pressure on days 28 and 56 and its change between these time points. FIG. 14c and FIG. 14d: Ejection fraction on days 28 and 56 and its change between these time points. Influence of Elevated Cholesterol Levels on Tβ4-Mediated Angio- and Arteriogenesis Number of endothelial cells (FIG. 15a), collaterals (FIG. 15b), and Rentrop score (FIG. 15c) in the ischemic area of hypercholesterolemic control and rAAV-Tβ4-treated animals.

Figure 16A:
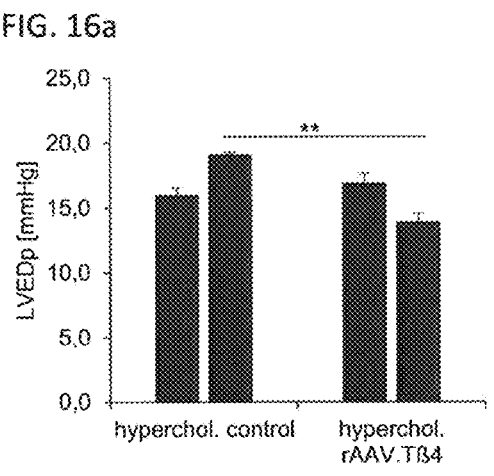
Figure 16B:
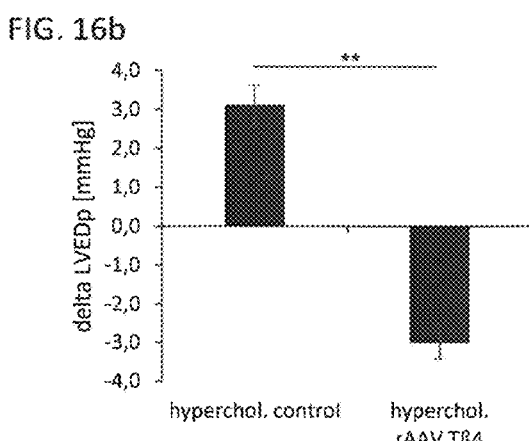
Figure 16C:
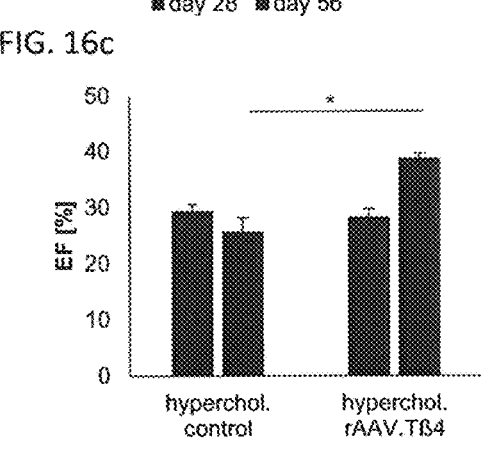
Figure 16D:
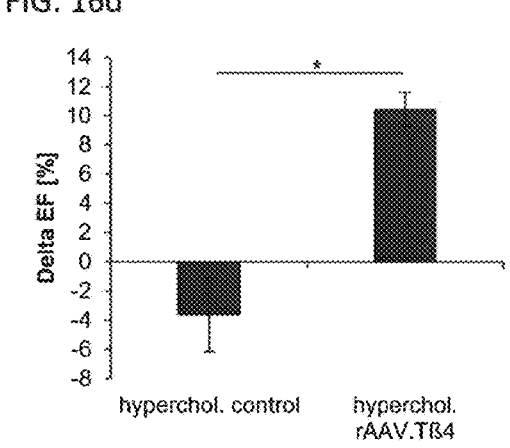
Figure 16E:
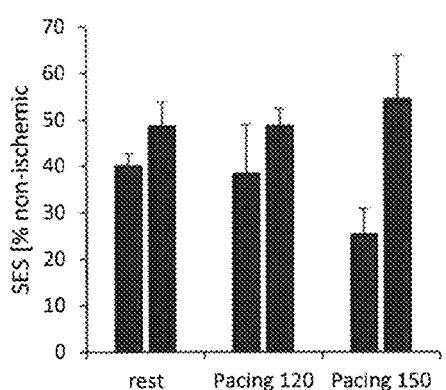

Functional Efficiency of rAAV.Tβ4 Application in Animals with Hypercholesterolemia FIG. 16a and FIG. 16b: Left ventricular end-diastolic pressure on days 28 and 56 and its change between these time points in hypercholesterolemic control and rAAV-Tβ4-treated animals. FIG. 16c and FIG. 16d: Ejection fraction on days 28 and 56 and its change between these time points in hypercholesterolemic control and rAAV-Tβ4-treated animals. FIG. 16e: Regional myocardium function, measured as subendocardial segment shortening at rest and with increased heart rate (130 and 150 beats per minute).

rAAV.Tβ4 and rAAV.MRTF-A Pretreatment in a Mouse Model of Sepsis

Figure 17D:
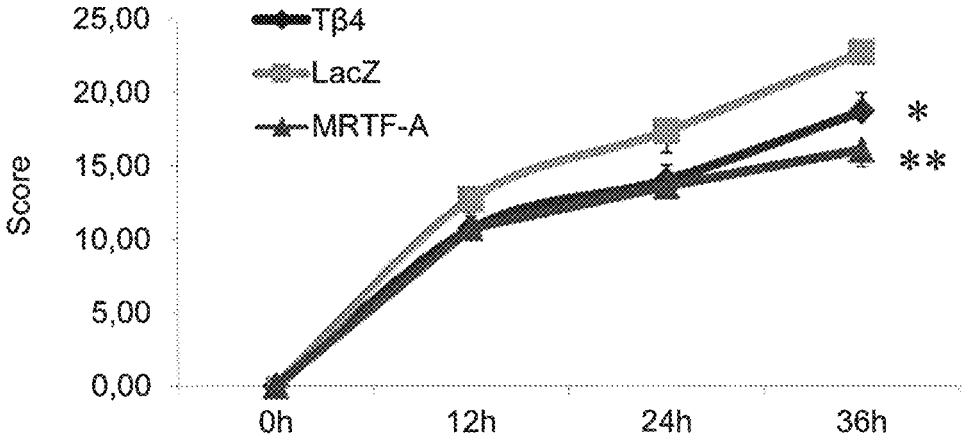
Figure 17E:
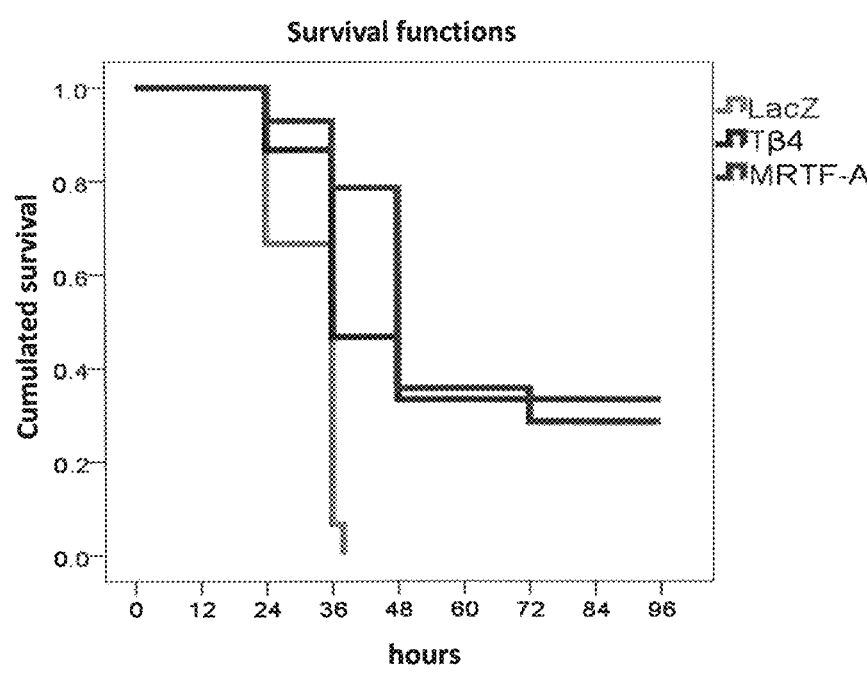

FIG. 17a: Protocol of the sepsis tests in mice. FIG. 17b: Scoring scheme for the assessment of sepsis symptoms in mice and determination of the stop criteria. FIG. 17c: Peripheral arterial blood pressure values after 12 and 24 hours in animals with sepsis treated with different rAAV. FIG. 17d: Symptom scores of the animals with sepsis in the treatment groups. FIG. 17e Cumulated survival after LPS-induced sepsis.

Role of MRTF-A and Tβ4 in Vascular Integrity During Sepsis

Figures 18A, 18B, 18C:
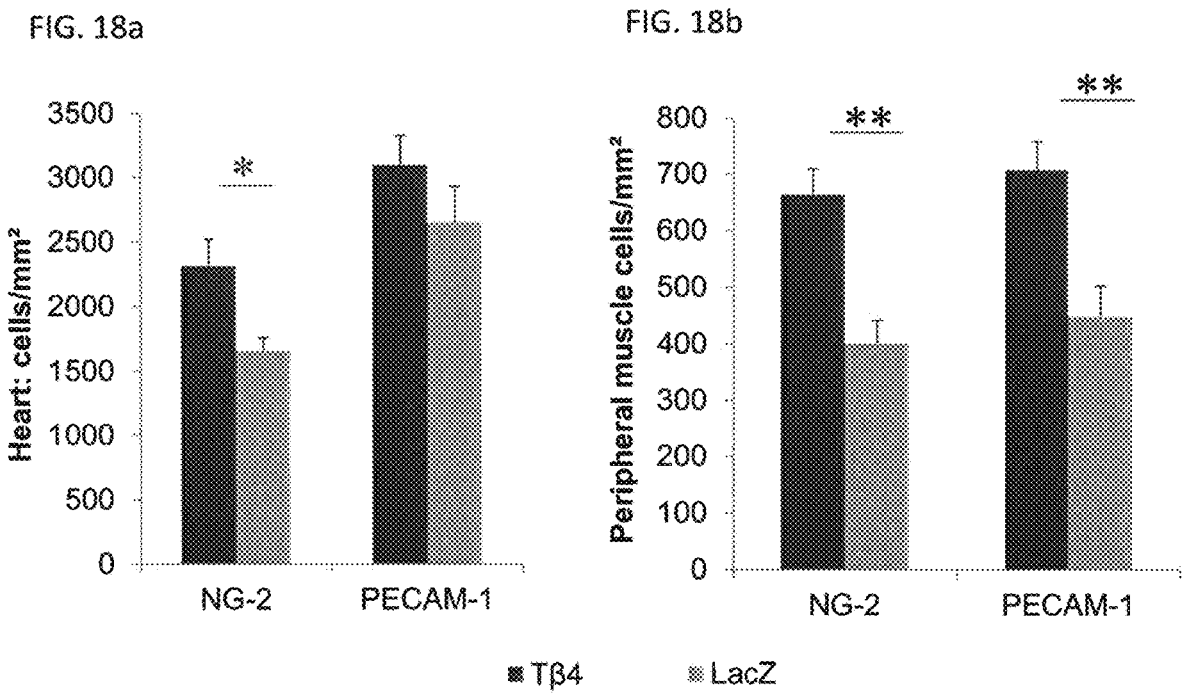
Figure 18D:
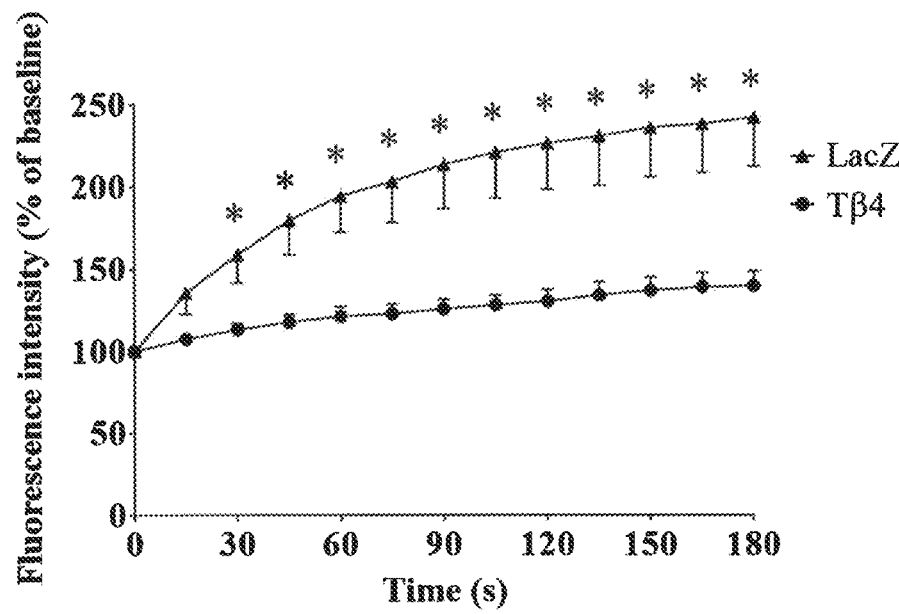

FIG. 18a and FIG. 18b: Histologic analyses of the endothelial cells (PECAM-1-positive cells) and the pericytes (NG-2-positive cells) in the hearts and the peripheral musculature of mice with sepsis. FIG. 18c and FIG. 18d: Exemplary images and quantitative analysis of a permeability measurement by means of fluorescently labeled high molecular dextran 6 hours after induction of sepsis.

DETAILED DESCRIPTION OF THE INVENTION

In our experiments (see Examples), we have found that the combination of a long-acting vector and the overexpression of an effective vasoactive growth factor represents a therapeutic option for patients with chronic ischemic diseases of skeletal or heart muscle tissue. The combination of an adeno-associated vector and thymosin β4 (Tβ4) or MRTF-A transgene, respectively, leads to robust therapeutic vessel reformation in three species (mouse, rabbit, and pig). This therapeutic neovascularization in turn leads to a notably improved perfusion in the models of peripheral arterial obstruction disease and chronic myocardial ischemia. In the model of chronic ischemic cardiomyopathy in pigs it leads additionally to increased heart function. This specific effect can be achieved even in large animals with additional cardiovascular risk factors (elevated sugar or lipid levels).

A key feature of MRTF-A activation is translocation into the nucleus after decrease of G actin levels and export from the nucleus when the amount of G actin increases (Miralles et al., *Cell* 2003, 113:329-42; Vartiainen et al., *Science* 2007, 316:1749-52). Enforced expression of MRTF-A or Tβ4, a peptide activating MRTF-A by G actin binding (FIG.

Figure 1I:
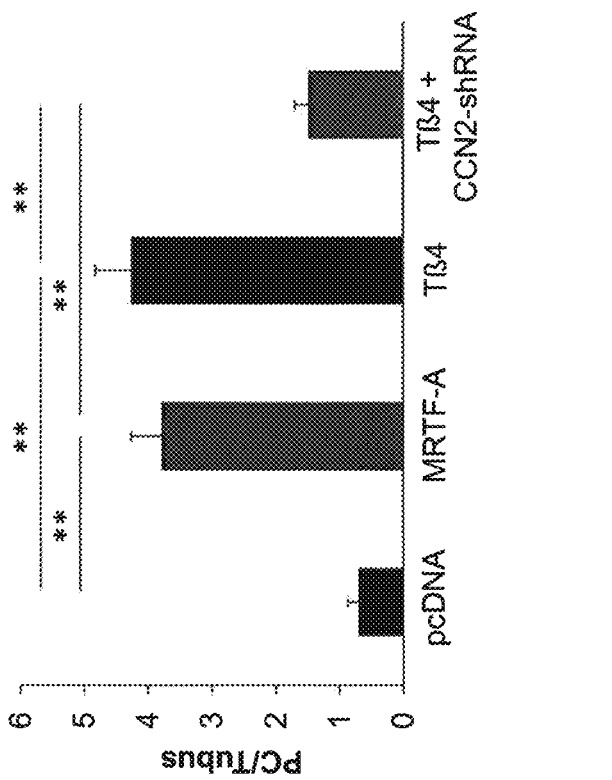

1a-FIG. 1i), initiates an orchestrated micro- and macrovascular growth response in the case of chronic ischemia of peripheral (FIG. 3a-FIG. 3l, FIG. 5a-FIG. 5g) and heart muscle cells (FIG. 7a-FIG. 7i). Consistent with these observations, chronic dysfunction of hibernating pig myocardium was resolved both by direct MRTF-A activation and MRTF-A activation via Tβ4 (shown in FIG. 7a to FIG. 7i). The idea that MRTF-A-SRF signaling provides myofilaments is of particular interest, since a loss of the actin cytoskeleton is a hallmark of hibernating myocardium caused by chronic coronary hypo-perfusion (Bito et al., *Circ Res* 2007, 100:229-37). Thus, MRTF-A is located at the interface of myocyte and vascular regeneration in hibernating myocardium. Tβ4, the most abundant G actin-binding peptide of the cytosol, can influence vascular growth by endothelial migration and sprouting (Grant et al., *J Cell Sci* 1995, 108:3685-94; Smart et al., *Nature* 2007, 445:177-82). A substantial role of MRTF-A in Tβ4 signaling has been shown in vitro and in vivo, since MRTF-A shRNA could suppress endothelial migration and sprouting (FIG. 1b, FIG. 1d) and micro- and macrovascular growth (FIG. 3d, FIG. 3f) and functional improvement of the heart (FIG. 10). Correspondingly, endothelium-specific deficiency in MRTFs caused incomplete formation of the primary vascular plexus in the developing retina (Weini et al., *J Clin Invest* 2013, 123:2193-206). Furthermore, MRF, the main target of MRTF-A, has recently been identified as essential for the behavior of apical cells in sprouting angiogenesis after VEGF-A stimulation (Franco et al., *Development* 2013, 2321-33; Andoh et al., *J Biochem* 2006, 140:483-9). Nevertheless, VEGF-A leads to the growth of immature and unstable capillaries (Dor et al., *EMBO J.* 2002, 21:1939-47), in contrast to Tβ4-MRTF-A, thus indicating a difference in the signaling mechanisms for these two vascular growth factors.

Collectively, our data demonstrate that activation of Tβ4-MRTF via CCN1/CCN2 augments collateral blood flow in the ischemic heart and hind limb via induction of CCN1/CCN2. At the cellular level this response involves endothelial sprouting via CCN-1 (CYR61) and maturation, i.e. pericyte investment, via CCN2 (CTGF), resulting in a stable and functional vascular network that can carry collateral blood flow and improve conductance. Pericyte investment is crucial here, since Ang-2, by virtue of disrupting pericyte investment (Ziegler et al., *J Clin Invest* 2013, 123:3436-45), abolished the positive effects exerted by Tβ4-MRTF signaling (shown in FIG. 3a to FIG. 3l). This finding supports a central role of vessel maturation and balanced vessel growth and paves the way for new therapeutic avenues towards functional neovascularization.

Therefore, the invention comprises in a first embodiment an adeno-associated viral vector (AAV vector) comprising a first gene encoding a myocardin-related transcription factor A (MRTF-A). AAV vectors herein are particles displaying the envelope of an adeno-associated virus while comprising in their interior a single-stranded DNA encoding a gene of interest. The gene of interest can be introduced into a target cell by infection of the target cell with an AAV vector.

The MRTF-A can be derived from a human, a mouse, a rabbit, a pig, or any other mammal.

Particularly preferred is the use of an AAV vector comprising envelope proteins, in particular the cap protein, of AAV9. AAV9 shows heart muscle tropism and thus provides for homogenous and stable expression in the heart muscle of a plurality of species. However, an AAV vector pseudotyped with AAV9 may also be used. By this a vector is meant comprising envelope proteins of AAV9, but otherwise expressing proteins of another strain and also containing genomic elements, for example internal terminal repeats (ITRs), from the other strain. For example, AAV2.9 is an AAV2 vector pseudotyped with envelope proteins of AAV9. For the present invention, AAV2.9, AAV1.9, and AAV6.9 are suitable as pseudotyped vectors. By using a heart muscle-tropic vector, it is ensured that expression of MRTF-A occurs in the heart muscle, where it can initiate therapeutic neovascularization.

Alternatively, an AAV vector with skeletal muscle tropism may also be used, in particular for the treatment of peripheral ischemia. Examples are AAV6, AAV1, AAV9, or vectors pseudotyped with these strains.

The vector of the invention can further comprise additional expressible genes, e.g. an expression cassette for a thymosin β4 (Tβ4) or an MRTF-B. The Tβ4 can be derived from a human, a mouse, a rabbit, a pig, or any other mammal. The MRTF-B can be derived from a human, a mouse, a rabbit, a pig, or any other mammal. Expression of these genes in the heart muscle also supports therapeutic neovascularization in myocardial ischemia.

The MRTF-A gene in the vector of the invention is preferably under the control of a cardio-specific promoter, i.e. a promoter enabling expression mainly in the heart muscle. Exemplary cardio-specific promoters are the MLC2 promoter, the α myosin heavy chain promoter (α-MHC promoter) and the troponin I promoter (TnI promoter). However, other constitutive or inducible promoters may be used, e.g. a CMV promoter or a MyoD promoter. The MRTF-A gene can also be under the control of several promoters.

Methods for the production of AAV vectors for the transfer of specific genes of interest are known in the state of the art (see e.g. Bell et al., *J Clin Invest* 2011, 121:2427-35). One method consists in the triple transfection of a suitable producer cell line, e.g. U293, and subsequent purification by cesium chloride gradient, as described in the section "Materials and methods" below. Here, the producer cells are transfected with three vectors: A first vector encodes the gene of interest, flanked by corresponding packaging signals; a second vector encodes the necessary AAV proteins, in particular rep and cap; and a third vector provides the adenoviral helper functions without which no AAV particle production is possible.

In a further embodiment, the invention relates also to a pharmaceutical composition comprising a vector of the invention and a pharmaceutically acceptable carrier. The pharmaceutical composition can be destined for every administration known in the art. Compositions for intravenous or intramuscular injection are preferred. The pharmaceutical composition can additionally comprise salts, buffers, stabilizers, coloring agents, thickeners, flavors, etc.

The invention also relates to the AAV vector described herein or the pharmaceutical composition of the invention for use as a medicament. In particular, such use can occur in a mammal for treatment of coronary heart diseases or peripheral ischemia. Preferred mammals are human, pig, rabbit and mouse.

The term "coronary heart disease" means a disease of the coronary vessels of the heart. The coronary heart disease can be myocardial ischemia, acute heart attack (myocardial infarction), stable angina pectoris and/or hibernating myocardium, but also cardiac arrhythmia and/or heart insufficiency. "Peripheral ischemia" is an insufficient perfusion or a complete loss of perfusion of a tissue or organ outside of the heart, while "myocardial ischemia" affects the heart muscle itself.

The vectors of the invention are particularly suitable for the treatment of "no option" patients. In such patients, all interventional and surgical therapeutic options are exhausted. Generally, slowing the progression of the disease by drug therapy is attempted. This however targets lipid reduction and platelet inhibition, but not neovascularization. Therapeutic neovascularization can overcome this hurdle, if molecular signaling pathways leading to balanced neovascularization are used. MRTF-A and also Tβ4 are two molecules that induce this type of balanced neovascularization (capillaries, microvascular maturation, and collateral formation) in ischemic tissue with concomitant lack of unwanted side effects.

Furthermore, vectors of the invention are particularly suitable for the treatment of subjects bearing additional cardiovascular risk factors. Such risk factors include diabetes mellitus, in particular diabetes mellitus type I or type II. The risk factor may also be an elevated concentration of cholesterol in the blood (hypercholesterolemia) that can be caused by a diet characterized as fat-rich. The elevated cholesterol concentration can be elevated LDL cholesterol concentration or elevated HDL cholesterol concentration.

EXAMPLES

Example 1: Induction of Hallmarks of Angiogenesis by MRTF-A In Vitro

We have found (FIG. 1*a* and FIG. 1*d*) that MRTF-A induced hallmarks of angiogenesis, i.e. migration and tubus formation of cultured human microvascular endothelial cells, to a comparable degree as Tβ4. The pro-angiogenic effect of MRTF-A was found to be dependent on the G actin binding motif of Tβ4, since mutation of this domain and abolition of G actin binding eliminated the effect of Tβ4 on vascular growth, similar to an shRNA shown to disrupt transcription of MRTF-A and -B (MRTF shRNA; Leitner et al., *J Cell Sci* 2011, 124:4318-31). Consistent therewith, Tβ4 increased MRTF-A translocation into the nucleus (FIG. 1*e*, FIG. 2*a* and FIG. 2*b*), similar to the transcription of an MRTF/SRF-dependent reporter gene containing three SRF binding sites of the c-fos promoter (p3DA.Luc, FIG. 1*f*; Geneste et al., *J Cell Biol* 2002, 157:831-8). Both MRTF-A and Tβ4 induced expression of genes involved in microvascular growth, in particular CCN1, mediating angiogenesis (Hanna et al., *J. Biol. Chem.* 2009, 284:23125-36), and CCN2, which is relevant for the attraction of 10T1/2 pericyte-like cells (FIG. 2*c*-FIG. 2*g*; Hall-Glenn et al., *PLoS ONE* 2012, 7:e30562). We observed that Tβ4 transfection did not affect the MRTF-A content (FIG. 2*h*), in contrast to MRTF-A transfection. Consistently with CCN1/2 being downstream of MRTFs and relevant for vessel formation, disruption by CCN1 shRNA prevented Tβ4-induced tubus formation (FIG. 1*g*), whereas CCN2 shRNA suspended the attachment of a murine pericyte-like cell line (C3H/10T1/2) to endothelial tubi in vitro (FIG. 1*i* and FIG. 1*j*).

Example 2: Treatment of Hind Limb Ischemia in the Mouse with AAV-Based MRTF-A Gene Therapy In order to further demonstrate the relevance of MRTF-A signaling in vivo, we employed a mouse model with hind limb ischemia. Intramuscular injection of recombinant AAV vectors (rAAV, FIG. 4*a* and FIG. 4*c*) increased tissue concentration of target proteins in the treated limb (FIG. 3*a*) and transcript levels of downstream mediators CCN1 and CCN2

(FIG. 3*b*; FIG. 4*d* and FIG. 4*f*). Consistent therewith, rAAV.MRTF-A induced capillary growth (FIG. 3*c* and FIG. 3*d*) and increased perfusion on day 7 (FIG. 3*e* and FIG. 3). As an upstream activator, Tβ4 had a similar effect on vascular growth and function (FIG. 2*c*-FIG. 2*f*), unless the G actin binding motif was missing (Tβ4m) or an rAAV.MRTF-shRNA was co-administered. This vector encodes an shRNA directed against both MRTF-A and MRTF-B and having the sequence 5'-GAUCCCCGCAUG-GAGCUGGUGGAGAAGAAUUCAAGAGAUUCUU-CUCCACCAGCUCCAUGUUUU UGGAAA-3' (SEQ ID NO:1). In order to further examine the relevance of Tβ4-induced vascular growth, rAAV.Cre was administered to Mrtfa$^{-/-}$/Mrtfb$^{flox/flox}$ hind limbs to generate MRTF-A/B double insufficiency. In Cre-induced MRTF-A/B knockout mice, Tβ4 was not capable of stimulating capillary growth (FIG. 3*g*) and pericyte recruitment (FIG. 4*g* and FIG. 4*h*) and of improving perfusion (FIG. 3*h*, FIG. 4*i*) on day 7 after induction of ischemia. Similarly, hind limbs did not show Tβ4-mediated increase of capillaries (FIG. 3*i* and FIG. 3*j*) or perfusion (FIG. 3*k* and FIG. 3*l*) on day 7, if rAAV.Cre was administered to CCN1$^{flox/flox}$ mice. Consequently, MRTF-A transduction or MRTF-A activation via Tβ4-mediated G actin sequestration stimulates transcription of CCN1 to mediate functional vascular regeneration.

Example 3: Treatment of Hind Limb Ischemia in the Rabbit with AAV-Based MRTF-A Gene Therapy The mutual dependence of microvascular growth and arteriogenesis for the mediation of regeneration of flow-through was studied in a rabbit model of ischemic hind limbs (FIG. 6*a*), which is compatible with topical separation of the microvascular growth area (lower limb) and the collateralization area (upper limb). Regional transduction of ischemic calf muscle with MRTF-A or Tβ4 (FIG. 5*a*, FIG. 6*b* and FIG. 6*d*) led to functional neovascularization, including CD31$^+$ capillary sprouting (FIG. 5*b* and FIG. 5*c*), NG2$^+$ pericyte investment (FIG. 5*b* and FIG. 5*d*) and collateral growth (FIG. 5*e* and FIG. 5*f*). In particular, MRTF activation via Tβ4 transduction of the hip region, though capable of inducing moderate collateral growth, did not increase perfusion, whereas limiting MRTF-A activation via Tβ4 to the calf region was sufficient to significantly stimulate micro- and macrovascular growth and perfusion (FIG. 6*e*-FIG. 6*i*). Detachment of microvascular pericytes by enforced angiopoietin 2 expression (FIG. 5*b* and FIG. 5*d*) abolished Tβ4-mediated collateralization and flowthrough improvement (FIG. 5*e* and FIG. 5*g*). Furthermore, blocking of flow-induced vasodilation by oral administration of L-NAME, a non-selective nitrogen oxide synthase inhibitor, did not affect capillary growth and maturation (FIG. 6*j*), but prevented formation of collaterals and increased perfusion (FIG. 6*k* and FIG. 6*l*). Thus, nitrogen oxide, subsequent to microvascular growth and maturation, appears to mediate collateral growth. This observation is supplemented by the finding that direct Tβ4 injection into the area of collateral growth (upper limb) did not improve perfusion to the same degree as distant injection of rAAV.Tβ4 into the lower limb, the area of microvascular growth (FIG. 6*e*-FIG. 6*i*). These findings indicate that microvascular maturation and nitrogen oxide signaling are processes that must take place in the sequence of MRTF-A-mediated vascular growth to achieve a functional neovascularization.

Example 4: Treatment of Hibernating Myocardium in the Pig with AAV-Based MRTF-A Gene Therapy Although both peripheral and coronary arteries perfuse muscle tissue, permanent contraction activity is a unique feature of the heart muscle, which requires a continuous oxygen supply. A chronic drop in oxygen supply changes the cellular composition of living cardiomyocytes in the ischemic area, leading to a regional loss of contraction force called hibernating myocardium (Heusch and Schulz, *J Mol Cell Cardiol* 1996, 28:2359-72; Nagueh et al., *Circulation* 1999, 100:490-6). Within cardiomyocytes, hallmarks of hibernating myocardium are reduced myofilament (Bito et al., *Circ Res* 2007, 100:229-37) and mitochondria content and increased glycogen content (St. Louis et al., *Ann Thoracic Surg* 2000, 69:1351-7). We examined the potential of MRTF-A to resolve dysfunction in hibernating myocardium induced by percutaneous implantation of a reduction stent in pig hearts (Kupatt et al., *J Am Coll Cardiol* 2007, 49:1575-84) leading to a gradual occlusion of the ramus circumflexus (RCx, FIG. 8*a*). On day 28, following rAAV.MRTF-A administration into the ischemic area that significantly increased MRTF-A content in the tissue (FIG. 8*b*), we detected a significantly higher degree of capillary density and pericyte investment (FIG. 7*a*-FIG. 7*c*). Collateral growth and perfusion under fast heart rate (130/min) were still impaired on day 28, i.e. before LacZ and MRTF-A transduction (FIG. 8*c*-FIG. 8*f*), but improved on day 56, i.e. 4 weeks after MRTF-A transduction, but not after LacZ transduction (FIG. 7*d*-FIG. 7*f*).

Increased collateral perfusion (FIG. 8*g*) generated an improved functional reserve of the ischemic area at fast heart rate (130 and 150 beats per minute, FIG. 7*g*). At the same time, we observed an improved ejection fraction as a marker of global systolic function (FIG. 7*h*) and a drop of the left ventricular end-diastolic pressure (FIG. 8*i*), a predictive marker of the beginning of heart failure.

Transgenic pigs that ubiquitously and constitutively express Tβ4 (FIG. 9) showed similar capillary growth and maturation (FIG. 7*a*-FIG. 7*c*). On day 56, the blood flow reserve in the ischemic area was increased (FIG. 7*f*) and the functional reserve in the ischemic region (FIG. 7*g*) or the entire heart (FIG. 7*h*) demonstrated an increase similar to rAAV.MRTF-A-treated hearts. In particular, due to the constitutive Tβ4 overexpression from day 0 to day 28, Tβ4tg animals did not experience a significant loss of perfusion or myocardial function at rest or at fast heart rate (FIG. 7*g*, FIG. 8*d*, FIG. 8*g*, FIG. 8*i*).

Furthermore, rAAV.Tβ4-induced micro- and macrovascular growth and subsequent increases in the perfusion reserve were suppressed when inhibiting MRTF-A shRNA was co-administered (FIG. 10*a*-FIG. 10*f*). The overall gain in global (FIG. 10*h*, examples in FIG. 10*i*) and regional myocardium function (FIG. 10*j*) was abolished when Tβ4 transduction was combined with MRTF-A inhibition by a suitable shRNA.

We therefore demonstrate, using a combined genetic and physiologic approach in each of a mouse, rabbit and pig model, that MRTFs stimulate the growth and maturation of microvessels as well as an increased collateral blood flow after arterial occlusion in hind limb and coronary networks. Mechanistically, we show that MRTF translocation downstream of thymosin β4 co-activates SRF and induces CCN1/CCN2, thereby leading to increased angiogenesis and recruitment of vascular smooth muscle cells and formation of functional vessels that can carry collateral flow (FIG. 7i).

Example 5: Treatment of Hibernating Myocardium in Diabetic Pigs with AAV-Based Tβ4 Gene Therapy Generation and Cardial Phenotyping of INS$^{C94Y}$-Transgenic Pigs (Diabetes Mellitus Type I)

The generation of transgenic pigs bearing the C94Y mutation in the insulin gene (INS$^{C94Y}$) is shown in FIG. 11a to FIG. 11e. This mutation is also depicted in Renner et al., *Diabetes* 2013, 62:1505-1511. The C94Y mutation leads to misfolding of the insulin protein in the β cells of the pancreas and an accumulation of the misfolded insulin in the endoplasmic reticulum (ER). ER stress leads to β cell apoptosis and thereby eventually to diabetes mellitus type I.

First, an INS$^{C94Y}$ expression vector was introduced into pig fibroblasts by means of nucleotransfection. After selection of the fibroblasts, a first round of somatic nucleus transfer into oocytes was performed. Subsequently, the offspring were analyzed by Southern blot and the animals with elevated blood glucose levels and delayed growth were used for renewed cloning (see Renner et al. 2013). These animals were then used for subsequent testing at 3-4 months of age.

Once insulin treatment was stopped, the animals showed a markedly elevated blood glucose level (FIG. 11c and FIG. 11d). Analyses of the heart tissue for endothelial cells (PECAM-1-positive cells, red) and for pericytes (NG-2-positive cells, green) revealed a marked reduction of the endothelial cell and pericyte number even without additional stress. The analysis of the left ventricular end-diastolic pressure shows a significant increase in animals with diabetes mellitus type I as a sign of reduced global heart function already at an early stage (FIG. 11e; mean±standard deviation; n=4, * p<0.05, **p<0.001).

FIG. 12a to FIG. 12d shows further effects of diabetes mellitus Type I or a fat-rich diet on the myocardium of pigs. FIG. 12a illustrates the experimental protocol of the pig model for hibernating myocardium with diabetes type I or hypercholesterolemia. Compared with the control groups (wt±rAAV.Tβ4), the INS$^{C94Y}$-transgenic animals with diabetes mellitus type I (labeled as control tg and rAAV.Tβ4 tg) showed elevated blood glucose levels for the entire assay period (FIG. 12b). However, no difference appeared between the rAAV.Tβ4-treated group and the control group either for the wild type group or for the transgenic animals (FIG. 12c and FIG. 12d). An influence of Tβ4 or MRTF-A on the blood glucose level is not to be expected. In the animals with hypercholesterolemia, considerably elevated triglyceride and cholesterol levels appeared in the serum after 9 weeks of ingesting a fat-rich diet (mean±standard deviation; n=4, **p<0.001).

Effect of rAAV.T64 Application in Animals with Diabetes Mellitus Type 1

In hibernating pig myocardium, rAAV.Tβ4 transduction induces capillary sprouting (PECAM-1 staining, red) and pericyte recruitment (NG-2 staining, green) in both groups (wild type and diabetes);] FIG. 13a-FIG. 13c. Moreover, considerable collateral growth was induced by overexpression of Tβ4 via rAAV (FIG. 13d), and a considerably better filling of the distal blood vessel could be measured by means of the Rentrop score (FIG. 13e). The effect could also be measured in both groups: wild type and diabetes (mean±standard deviation; n=4, * p<0.05, **p<0.001).

The left ventricular end-diastolic pressure, a parameter of global myocardium function, which showed an increase in the control animals of both groups from day 28 to day 56, was considerably reduced in the animals with rAAV.Tβ4 transduction (FIG. 14a and FIG. 14b). The ejection fraction, a further parameter of global myocardium function, showed a further decrease of values from day 28 to day 56 in control animals, whereas the value after Tβ4 overexpression considerably improved in both groups (wild type and diabetes) (FIG. 14c and FIG. 14d; mean±standard deviation; n=4, * p<0.05, **p<0.001).

Figure 15A:
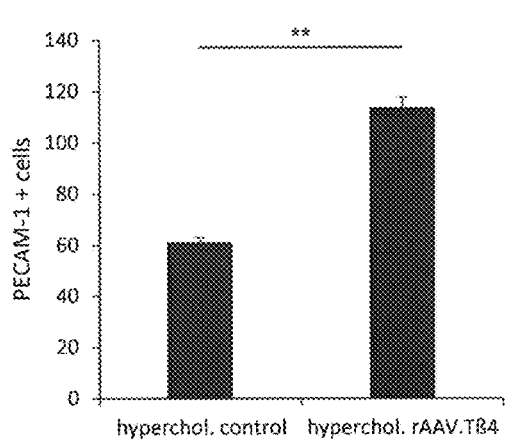
Figure 15B:
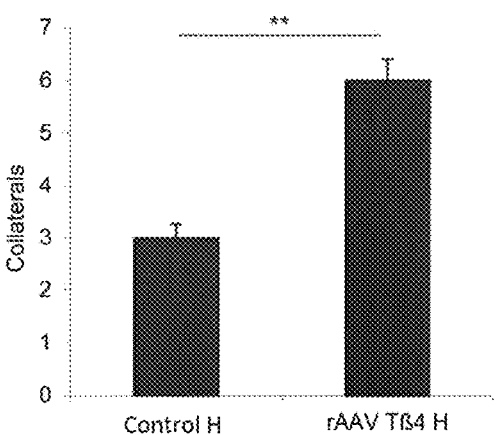
Figure 15C:
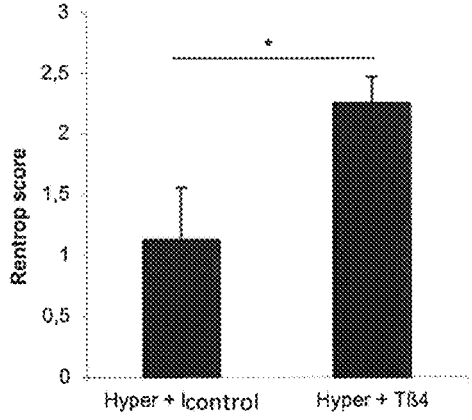

Example 6: Effects of Tβ4 Gene Therapy on the Myocardium of Pigs with Hypercholesterolemia In control animals receiving 9 weeks of a fat-rich feeding, a considerable reduction of capillaries (PECAM-1-positive cells) appeared in the ischemic area (FIG. 15a). With rAAV.Tβ4 application, the capillaries (PECAM-1-positive cells) in the ischemic area could be considerably increased. With rAAV.Tβ4 transduction, the collateral growth could be increased even in animals having elevated cholesterol levels (FIG. 15b). This also led to a better filling of the distal vessel section in the ischemic area, as shown by the Rentrop score (FIG. 15c; mean±standard deviation; n=4, * p<0.05, **p<0.001).

The left ventricular end-diastolic pressure, a parameter of global myocardium function, which was increasing in the control animals from day 28 to day 56, was considerably reduced in the animals with rAAV.Tβ4 transduction (FIG. 16a and FIG. 16b). The ejection fraction, a further parameter of global myocardium function, showed a further decrease of values from day 28 to day 56 in control animals, whereas the value after Tβ4 overexpression improved considerably (FIG. 16c and FIG. 16d). The regional myocardium function, measured as segment shortening at rest and under increased heart rate (130 and 150 beats per minute) showed an improved functional reserve in animals with rAAV.Tβ4 therapy (FIG. 16e; mean±standard deviation; n=4, * p<0.05, **p<0.001).

Example 7: Role of MRTF-A and Tβ4 in Vascular Integrity of Mice with Sepsis

FIG. 17a illustrates the protocol of the sepsis experiments conducted in mice. Sepsis was induced 14 days after rAAV treatment (rAAV.MRTF-A or rAAV.Tβ4) by injection of LPS. At seven time points after sepsis induction (12 h, 24 h, 36 h, 48 h, 72 h, 96 h, 120 h), an assessment of the symptoms was carried out by means of the table shown in FIG. 17b. The transduction of MRTF-A or Tβ4 via rAAV before induction of sepsis leads to increased peripheral arterial blood pressure values after 12 and 24 hours (FIG. 17c). In the course of up to 36 hours after sepsis, the rAAV.Tβ4- and rAAV.MRTF-A-treated animals show considerably lower symptom scores as compared with the rAAV.LacZ-treated control animals (FIG. 17d). The cumulative survival after LPS-induced sepsis is considerably improved by overexpression of Tβ4 and MRTF-A (FIG. 17e; mean±standard deviation; n=7-15, * p<0.05, **p<0.001).

Histological analyses of endothelial cells (PECAM-1-positive cells) and pericytes (NG-2-positive cells) showed an elevated cell number in the heart and the peripheral muscles of animals treated with Tβ4 (FIG. 18a and FIG. 18b) compared to control animals transduced with rAAV. LacZ. Exemplary images and a quantitative analysis of a permeability measurement by means of fluorescently labeled high molecular dextran 6 hours after sepsis induction are shown in FIG. 18c and FIG. 18d. Here a considerably reduced leakage of the indicator was observed after Tβ4 overexpression compared to the lacZ-transduced control animals (mean±standard deviation; n=4, * p<0.05, **p<0.001).

Materials and Methods

The experiments described in the examples were performed using the techniques described in the following.

Reagents

All cell culture media and chemicals were purchased from SIGMA (Deisenhofen), if not indicated to the contrary. Contrast agent Solutrast 370 was supplied by Byk Gulden (Konstanz).

Adeno-Associated Viral Vectors

Recombinant vectors rAAV.MRTF-A, rAAV.Tβ4, r.AAV.Tβ4m, rAAV.LacZ, rAAV.Cre, and rAAV.MRTF-shRNA were produced by means of triple transfection of U293 cells. One plasmid encoded the transgene under control of a CMV promoter flanked by cis-acting internal terminal repeats of AAV2. In the case of rAAV.MRTF-A, this was the plasmid pAAV-CMV-mMRTF-A (SEQ ID NO:16). However, a plasmid encoding human MRTF-A may also be used, e.g. pAAV-CMV-hMRTF-A (SEQ ID NO:17). A second plasmid provided AAV2 rep and AAV9 cap in trans (Bish et al., Hum. Gene Ther. 2008, 19:1359-68), while a third plasmid (delta F6) supplemented adenoviral helper functions. Cells were harvested 48 hours later and vectors purified using a cesium chloride gradient as described previously (Lehrke et al., Cell Metab 2005, 1:297-308). Viral titers were measured by real time PCR versus the polyA tail of the bGH of the vector (see primer sequences in Table 1). Trans and helper plasmids were supplied by courtesy of James M. Wilson, University of Pennsylvania.

Cell Culture

SatisFection (TPP AG, Trasadingen, Switzerland) was used for the transfection of human microvascular endothelial cells (HMECs), murine endothelial cells (bEnd.3), and the myocytic cell line HL-1 according to the manufacturer's instructions. 100 µl serum- and antibiotic-free DMEM medium were mixed with 3 µl of SatisFection transfection reagent.

In Vitro Tubus Formation and Co-Culturing Experiments

For the Matrigel experiments, HMECs were transfected with pcDNA, MRTF-A, Tβ4±MRTF-shRNA, Tβ4m (lacking the G actin binding motif KLKKTET; Bednarek et al., J. Biol. Chem. 2008, 283:1534-44), or Tβ4±CCN1-shRNA. Cells (8000 cells per well) were seeded on Matrigel (BD Matrigel™ Basement Membrane Matrix, BD Biosciences, San Jose, USA) in basal endothelium growth media with a supplement of 5% fetal calf serum and images were made after 18 h. The number of rings in the low power field was quantified.

In co-culturing experiments, HL-1 cells were transduced with r.AAV.Tβ4±CCN1-shRNA, rAAV.MRTF-shRNA, or rAAV.Tβ4m (1×10⁶ AAV6 particles per cell). HL-1 and HMECs embedded in Matrigel (8,000 per well) were physically separated by a semipermeable membrane. After 18 h, the HL-1 cells were removed and ring formation in the low power field was quantified.

CH3/10T1/2 pericyte cell attraction to murine endothelial cells (bEnd.3) was tested after transfection of the endothelial compartment with pcDNA, MRTF-A, or Tβ4±CCN2-shRNA by means of SatisFection (Agilent, Böblingen). Endothelial cells were stained with DiD (red, Vybrant®, Life Technologies) and seeded on Matrigel (12.000 cells per well). After 6 h, pericyte-like cells stained with DiO (Vybrant®, Life Technologies) (2,000 cells per well) were added and migration to the tubi was allowed for 2 h. The co-culturing images were made by means of confocal laser microscopy (Carl Zeiss, Jena).

Migration Assay

HMECs were transfected as above with the indicated transgenes. 60,000 cells were grown to confluence in wells with a strip-like insert (ibidi GmbH, Planegg). After 48 h, the nuclei were stained with Syto62. Then cells were fixed with 2% PFA, permeabilized, and incubated with an anti-MRTF-A antibody (Santa Cruz Biotech, Santa Cruz, USA) and a secondary antibody (Alexa 488-coupled, Invitrogen, Karlsruhe). Images were made by means of confocal laser microscopy (Carl Zeiss, Jena) and the mean fluorescence intensity of the area of 100 nuclei, identified with Syto62, were automatically evaluated using the LS5 image browser.

HPLC Analysis

Detection of Tβ4 was performed as described earlier (Huff et al., Ann. N. Y. Acad. Sci. 2007, 1112:451-7). Here, tissue samples were disrupted by adding 4 M perchloric acid with 1% thiodiethanol up to a final concentration of 0.4 M. Mixtures were homogenized, incubated for 30 min at 4° C. and centrifuged for 10 min at 20,000 g. The supernatant was analyzed using reverse phase chromatography. In rabbits, endogenous and exogenous Tβ4 were distinguished by detection of the rabbit-specific Tβ4-Ala.

Luciferase Assay

To determine MRTF-dependent luciferase activity, HMECs and HL-1 cells were transfected with p3DA.Luc (=a construct of a synthetic promoter having three copies of the c-fos SRF binding site and a Xenopus type 5 actin TATA box plus a transcription start site inserted in pGL3; Posern et al., Mol. Biol. Cell 2002, 13; 4167-78), an SRF reporter gene, and 930 ng of pcDNA, Tβ4 or Tβ4m. Comparable transfection efficiencies were ensured by co-transfection of 50 ng ptkRL (Renilla luciferase reporter). Pellets of cells were obtained and lysed, further purified by centrifugation for 10 min at 4° C. and 13.000 rpm and used for the determination of firefly luciferase activity and Renilla luciferase activity. The ratio of firefly/Renilla luciferase activity was calculated.

RNA Modulation and Detection

Real time PCR (RT-PCR) was conducted with SYBR Green dye (iQ SYBR Green Supermix, Bio-Rad, München) and measured on an iQ cycler (Bio-Rad, München). The primers are listed in Table 1. Expression levels were normalized to GAPDH and shown as multiples of the pcDNA control situation. The comparative 2 DDCt method was performed as described earlier (Pfosser et al., Cardiovasc Res 2005, 65:728-36).

Western Blot Analysis of MRTF-A

For the analysis of whole MRTF-A protein, cell culture and tissue samples were homogenized in 1 ml lysis buffer containing 20 mM Tris, 1 mM EDTA, 140 mM NaCl, 1% Nonidet P-40 (NP-40), 0.005 mg/ml leupeptin, 0.01 mg/ml aprotinin, 1 mM PMSF, pH7.5. 60 µg whole protein extract were separated by polyacrylamide gel electrophoresis with 10% sodium dodecyl sulfate (SDS-PAGE). After electrophoresis, the proteins were electrotransferred to a PVDF membrane (Millipore, Billerica, USA), blocked with 5% fat-free milk in PBS buffer containing 0.1% Tween 20 and incubated overnight at 4° C. with primary antibodies against MRTF-A (C-19; Santa Cruz Biotech, Santa Cruz, USA). After washing, the membrane was incubated with a secondary antibody (donkey anti-goat IgG, HRP-conjugated; Santa Cruz Biotech, Santa Cruz, USA) and developed with a chemiluminescence reagent (ECL; GE Healthcare, Buckinghamshire, England). For analysis of the MRTF-A protein content in the nucleus or the cytosol, respectively, a separation with the Ne-Per® reagents for cytoplasmic and nucleus extraction (Thermo Scientific, Rockford, USA) was conducted according to the manufacturer's guidelines. Then a Western blot analysis was carried out as described above. As a control protein, either α-tubulin (6A204; Santa Cruz Biotech, Santa Cruz, USA) or, for the nucleus fraction, lamin B1 (ZL-5; Santa Cruz Biotech, Santa Cruz, USA) was used.

Animal Experiments

Animal care and all experimental procedures were carried out under strict adherence to the German and NIH animal guidelines and have been approved by the Animal Protection Commission of the Government of Upper Bavaria (AZ 55.2-1-54-2531-26/09, 130/08, 140/07). All animal experiments were conducted at the Walter Brendel Center for Experimental Medicine in Munich.

Mouse Hind Limb Ischemia

Unilateral hind limb ischemia of the right leg was performed in male C56Bl mice of the same age (Charles River, Sulzfeld) and in MRTF-A$^{+/-}$/B$^{flox/flox}$, MRTF-A$^{-/-}$/B$^{flox/flox}$, MRTF-A$^{+/-}$/B$^{-/-}$-Vi (=MRTF-A-$^{+/-}$/B$^{flox/flox}$+3×10$^{12}$ rAAV.cre), MRTF-A$^{-/-}$/B$^{-/-}$-Vi (=MRTF-A-$^{-/-}$/B$^{flox/flox}$+3× 10$^{12}$ rAAV.cre) (Weinl et al., *J. Clin. Invest.* 2013, 123:2193-226) and CCN1-1-Vi mice (=Cyr61$^{flox/flox}$+3×10$^{12}$ rAAV.Cre; produced in the laboratory of Ralf Adams at the Max Planck Institute for Molecular Biomedicine in Münster) as previously described (Limbourg et al., *Nat. Protocols* 2009, 4:1737-48). Before induction of ischemia (day −14), 3×10$^{12}$ AAV9 virus particles were administered intramuscularly to the right leg as described (Qin et al., *PLoS ONE* 2013, 8:e61831). On day 0, the left leg underwent mock surgery, whereas in the right leg the femoral artery was ligated. The measurements of post-ischemic blood flow recovery were conducted by means of laser Doppler flow-through cytometry (Moor Instruments, Devon, England). Measurements were made directly before and after surgery, on day 3, and on day 7. The results are given as the ratio of right leg to left leg including subtraction of the background tissue value. RT-PCR and HPLC analysis were carried out on day 5 after induction of ischemia; tissue was collected from treated and non-treated legs. Analyses of capillary density and vascular maturation were carried out on day 7 in all groups by means of PECAM-1 (sc1506, Santa Cruz Biotech, Santa Cruz, USA) and NG2 staining (in MRTF-A$^{+/-}$/B$^{flox/flox}$ mice; Chemicon, Nürnberg) in frozen tissue samples of the *M. gastrocnemius* and *M. adductor.*

Rabbit Hind Limb Ischemia

On day 0, the complete femoral artery of the right leg in New Zealand rabbits was removed (Pfosser et al., *Cardiovasc. Res.* 2005, 65:728-736) and rAAV administration (5×10$^{12}$ virus particles) was performed by means of intramuscular injection into the right hind limb as indicated. On day 7 and day 35, angiography was performed by injection of contrast agent (Solutrast 370, Byk Gulden, Konstanz) into the ischemic leg with an automatic injector (Harvard Apparatus, Freiburg). Furthermore, fluorescent microbeads (15 μm, Molecular Probes®, Life Technologies, Carlsbad, USA) were used for blood flow measurements in ischemic and non-ischemic tissue. For blood flow analysis, tissue samples were digested as previously described (Thein et al., *Comput. Methods Programs Biomed.* 2000, 61:11-21; Kupatt et al., *J Am Coll Cardiol* 2010, 56:414-22). Fluorescence analysis was carried out with a Tecan Saphire 2 microtiter plate reader at the emission wavelengths 680 nm, 638 nm, 598 nm, 545 nm, 515 nm, 468 nm, and 424 nm, depending on the fluorescent dye employed. Calculations were carried out as described previously (Lebherz et al., *Endothelium* 2003, 10:257-65). Analysis of capillary density and vascular maturation was carried out by means of PECAM-1 (sc1506, Santa Cruz Biotech, Santa Cruz, USA) and NG2 staining (in MRTF-A$^{+/-}$/B$^{flox/flox}$ mice; Chemicon, Nürnberg) in frozen tissue samples of the ischemic and non-ischemic leg.

Chronic Myocardial Ischemia in Pigs

Pigs were anesthetized and treated as described previously (von Degenfeld et al., *J. Am. Coll. Cardiol.* 2003, 42:1120-8). To this end, a reduction stent coated with a PTFE membrane was implanted in the proximal RCx, leading to 75% reduction of blood flow. Correct localization of the stent and permissibility of the distal vessel were ensured by the injection of contrast agent. On day 28, the baseline measurements for global myocardium function (left ventricular end-diastolic pressure=LVEDP, ejection fraction=EF) and myocardial perfusion (fluorescent microbeads, 15 μm, Molecular Probes®) were conducted. Then selective pressure-regulated retroinfusion into the large cardiac vein draining the RCx-perfused myocardium was carried out for 5×10$^{12}$ virus particles of rAAV.MRTF-A and rAAV.Tβ4±rAAV.MRTFA-shRNA. On day 56, the measurements of global myocardium function and blood flow were repeated and the regional myocardium function of the ischemic and non-ischemic area were determined (at rest and under fast heart stimulation, 130 and 150 bpm). Post mortem angiography was carried out for the calculation of the collateral value and analysis by Rentrop score (0=no filling, 1=side branch filling; 2=partial main vessel filling; 3=complete main vessel filling). Tissue was collected for the analysis of regional myocardial blood flow and immunohistology.

Global Myocardial Function

On day 28 and day 56, the global myocardial function (LVEDP) was examined by a Millar pressure tip catheter (Sonometrics, Ontario, Canada). An angiogram of the left ventricle for global myocardial function was performed on day 28 and day 56. The ejection fraction was obtained by planimetry of the end-systolic and end-diastolic angiogram images (Image J 1.43u, National Institute of Health, USA).

Regional Myocardial Function

On day 56 after induction of ischemia, sternotomy was performed and ultrasound crystals were placed subendocardially in a standardized manner in the non-ischemic area (LAD control region) and the ischemic area (Cx perfused region). Subendocardial segment shortening (SES, Sonometrics, Ontario, Canada) was examined at rest and under elevated heart rate (functional reserve, rate 130 and 150) and evaluated off-line depending on ECG.

Regional Myocardial Blood Flow

The analysis of regional myocardial blood flow was performed on day 28 (before rAAV treatment) and day 56 (28 days after AAV treatment) by means of fluorescent microbeads (Molecular Probes®). The microbeads (15 μm, 5×10$^6$ particles per injection) were injected into the left ventricle with a pigtail catheter. Blood flow measurements were carried out at rest and at elevated heart rate (130 bpm). The fluorescence content was analyzed by means of a Tecan Sapphire 2 microtiter plate reader and a calculation of the regional myocardial blood flow was performed, either as ml/g tissue absolute or as the ratio to the non-ischemic region at rest (% non-ischemic blood flow; Kupatt et al., *J Am Coll Cardiol* 2010, 56:414-22).

Histology

Tissue samples of the ischemic and non-ischemic area were examined for capillary density (PECAM-1-positive cells, red) and pericyte investment (NG-2-positive cells, green). Staining of capillaries was carried out with an anti-CD31 antibody (SC1506, Santa Cruz Biotech, Santa Cruz, USA) and a rhodamine-labeled secondary antibody, while vascular maturation was quantified by pericyte co-staining (anti-NG2-antibody AB5320, Millipore, Billerica, USA). Images of the ischemic and non-ischemic region were made with high power field magnification (40 times), and 5 independent images per region (ischemic and non-ischemic) and animal were quantified.

rAAV Transduction Efficiency

For the evaluation of the rAAv transduction efficiency, control mice, rabbits and pigs were treated with rAAV.LacZ. Cryostatic sections of the LacZ-transduced animals were prepared and stained for β-galactosidase (blue staining). Furthermore, RT-PCR for the several transgenes was carried out using the primers described in Table 1 and analyzed as described above.

Tomato Reporter Gene Mice

These mice homozygously expressing mT/mG (Jackson Laboratory, Bar Harbor, USA) express loxP sites on both sides of a membrane-directed tdTomato (mT) and a membrane-directed eGFP (Muzumdar et al., *Genesis* 2007, 45:593-605). Cre expression via rAAV.Cre for the determination of virus transduction efficiency deleted mT (red fluorescence) in the cells and enabled eGFP expression (green fluorescence) in the same cells (FIG. 4*b*).

Statistical Methods

The results are shown as means±standard deviation. Statistical analyses were performed using one-way variance analysis (ANOVA). Every time a significant effect was found ($p < 0.05$), we conducted multiple comparative tests between groups with the Student Newman Keul method (IBM SPSS 19.0; IBM, Chicago, USA). Differences between groups were regarded as significant at $p < 0.05$.

TABLE 1

| Primer sequences used for PCR: | | |
|---|---|---|
| BGH forward | 5'-TCT AGT TGC CAG CCA TCT GTT GT-3' | SEQ ID NO: 2 |
| BGH reverse | 5'-TGG GAG TGG CAC CTT CCA-3' | SEQ ID NO: 3 |
| GAPDH forward | 5'-AAT TCA ACG GCA CAG TCA AG-3' | SEQ ID NO: 4 |
| GAPDH reverse | 5'-ATG GTG GTG AAG ACA CCA GT-3' | SEQ ID NO: 5 |
| Tβ4 forward | 5'-TCA TCG ATA TGT CTG ACA AAC-3' | SEQ ID NO: 6 |
| Tβ4 reverse | 5'-CAG CTT GCT TCT CTT GTT CAA-3' | SEQ ID NO: 7 |
| MRTF-A forward | 5'-AAT CCA TGG GTC GAC GGT ATC GAT-3' | SEQ ID NO: 8 |
| MRTF-A reverse | 5'-ATA CCA TGG TCA GGC ACC GGG CTT-3' | SEQ ID NO: 9 |
| CCN1 (CYR61) forward | 5'-GCT AAA CAA CTC AAC GAG GA-3' | SEQ ID NO: 10 |
| CCN1 (CYR61) reverse | 5'-GGC TGC AAC TGC GCT CCT CTG-3' | SEQ ID NO: 11 |
| CCN2 (CTGF) forward | 5'-CCC TAG CTG CCT ACC GAC T-3' | SEQ ID NO: 12 |
| CCN2 (CTGF) reverse | 5'-CAT TCC ACA GGT CTT AGA ACA GG-3' | SEQ ID NO: 13 |
| Ang2 forward | 5'-TCG AAT ACG ATG ACT CGG TG-3' | SEQ ID NO: 14 |
| Ang2 reverse | 5'-GTT TGT CCC TAT TTC TAT C-3' | SEQ ID NO: 15 |

We claim:

1. A method for inducing neovascularization in ischemic tissue of a mammal diagnosed with coronary heart disease or peripheral ischemia, comprising:
   injection an injecting a recombinant adeno-associated viral (AAV) vector comprising a nucleic acid sequence encoding myocardin-related transcription factor A (MRTF-A) into the ischemic tissue such that neovascularization occurs in the ischemic tissue.

2. The method of claim 1, wherein the neovascularization in the ischemic tissue comprises increased capillary density and microvascular growth, wherein the microvascular growth occurs concurrently with an increase in pericyte cell recruitment.

3. The method of claim 1, wherein the AAV vector is an AAV2/9 vector.

4. The method of claim 1, wherein the nucleic acid sequence encoding MRTF-A is operably linked to a myosin light chain 2 (MLC2) promoter, an a myosin heavy chain ($\alpha$-MHC) promoter, or a troponin (TnI) promoter.

5. The method of claim 1, wherein the coronary heart disease is myocardial ischemia or hibernating myocardium.

6. The method of claim 1, wherein the nucleic acid sequence encoding MRTF-A is operably linked to a CMV promoter or a myoblast determination protein 1 (MyoD) promoter.

7. The method of claim 1, wherein the expression of MRTF-A in the injected ischemic tissue increases the capillary-to-muscle fiber ratio (c/mf).

8. The method of claim 1, wherein the nucleic acid sequence encoding MRTF-A is a human, mouse, rabbit, or pig nucleic acid sequence encoding MRTF-A.

9. The method of claim 1, wherein the MRTF-A is a human, mouse, rabbit, or pig MRTF-A.

10. The method of claim 1, wherein the injecting the AAV vector is by intravenous injection or intramuscular injection.

11. A pharmaceutical composition comprising:

a) a pharmaceutically acceptable carrier; and b) a recombinant adeno-associated virus 2/9 (AAV2/9) vector comprising a nucleic acid sequence encoding MRTF-A operably linked to a promoter.

12. The pharmaceutical composition of claim 11, wherein the promoter is a myosin light chain 2 (MLC2) promoter, an a myosin heavy chain (α-MHC) promoter, or a troponin (TnI) promoter.

13. The pharmaceutical composition of claim 11, wherein the promoter is a CMV promoter or a myoblast determination protein 1 (MyoD) promoter.

14. The pharmaceutical composition of claim 11, wherein the nucleic acid sequence encoding MRTF-A is a human, mouse, rabbit, or pig nucleic acid sequence encoding MRTF-A.

* * * * *